United States Patent
Ford

(10) Patent No.: US 8,759,584 B2
(45) Date of Patent: Jun. 24, 2014

(54) SYNTHESIS OF BIGUANIDINES AND TRIAZINES, AND BIGUANIDINO-ALUMINIUM COMPLEXES AS INTERMEDIATES

(75) Inventor: Mark James Ford, Schmitten (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 12/808,060

(22) PCT Filed: Nov. 25, 2008

(86) PCT No.: PCT/EP2008/009962
§ 371 (c)(1),
(2), (4) Date: Jun. 14, 2010

(87) PCT Pub. No.: WO2009/077059
PCT Pub. Date: Jun. 25, 2009

(65) Prior Publication Data
US 2010/0305317 A1    Dec. 2, 2010

(30) Foreign Application Priority Data
Dec. 14, 2007 (EP) .................................. 07024256

(51) Int. Cl.
C07F 5/06 (2006.01)
C07D 251/54 (2006.01)

(52) U.S. Cl.
CPC ..................................... C07F 5/069 (2013.01)
USPC ........... 564/233; 564/234; 564/235; 544/196; 544/204

(58) Field of Classification Search
USPC .......................................... 564/233, 234, 235
See application file for complete search history.

(56) References Cited

U.S. PATENT DOCUMENTS

2009/0123513 A1 * 5/2009 Greener ........................ 424/423

OTHER PUBLICATIONS

Nandi, S.D. et al. "Complexes of aluminum (III) and beryllium (II) with biguanide". Zeitschrift fuer naturforschung, Teil B: Anorganische Chemie, Biochemie, Biophysik, Biologie, 29 (5-6), 347-348, Coden: Zenbax, 0044-3174, 1974.

* cited by examiner

*Primary Examiner* — Venkataraman Balasubramanian
(74) *Attorney, Agent, or Firm* — Frommer Lawrence & Haug LLP

(57) ABSTRACT

Compounds of formula (I) or salts thereof,

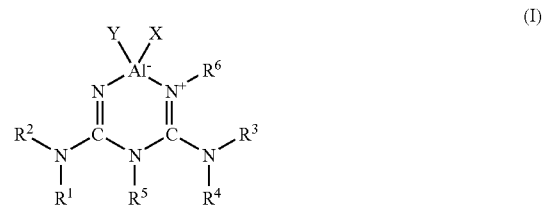

in which $R^1$, $R^2$, $R^3$, $R^4$, $R^5$, $R^6$, X and Y are defined as in claim 1, can be prepared by a process characterized in that a compound of the formula (II) or a salt thereof,

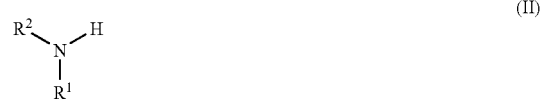

is reacted to a compound of the formula (III) or a salt thereof,

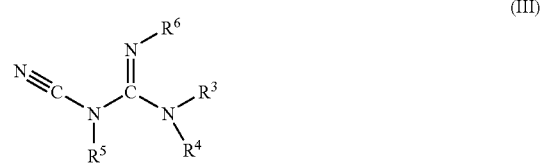

and an aluminium(III) source, optionally, in the presence of a protic additive or solvent selected from the group consisting of alcohols or amines.
The compounds (I) are suitable to be used for the preparation of heterocyclic compounds corresponding to (I) where the group Al(X)(Y) is replaced with an optionally substituted carbon atom, or s-triazine derivatives thereof.

2 Claims, No Drawings

SYNTHESIS OF BIGUANIDINES AND TRIAZINES, AND BIGUANIDINO-ALUMINIUM COMPLEXES AS INTERMEDIATES

The invention is related to the technical field of chemical processes for the preparation of heterocyclic compounds, particularly to the preparation of symmetrical triazines (s-triazines), and intermediates therefor, by ring-formation of the triazine ring. The s-triazines preferably are active ingredients in the pharmaceutical, agrochemical or fine chemicals field or are intermediates thereof.

It is well documented in the literature that biguanidine salts may be prepared from the reaction of cyanamide and guanidine salts or cyanoguanidine and ammonium salts at high temperatures in solution or as a melt. Even in the simplest of cases these syntheses are however often unspecific, lead to low yield and give mixtures from which the product is difficult to obtain. This is primarily due to the fact that the temperature required for reaction, often very much in excess of 120° C., is such that the biguanidine product itself reversibly decomposes to give the related guanidine and cyanamide derivatives which may themselves further take part in the reaction. In addition from the side products produced these decompositions may be extremely exothermic and as such preclude operating such a reaction on a technical scale. An example of which is that, in some cases it has been documented that under virtually identical reaction conditions some amines yield unpredictably only the mono-guanidine product in low yield (J. Amer. Chem. Soc. 81, 3728, 1959, see example on page 3735 with 2-cyclohexylethylamine). Alternatively, for those cases where fusion or boiling in strong acid are not appropriate the use of copper salts (e.g. copper sulfate) is known to promote the formation of the biguanidine as the bisguanidino copper complex, albeit in only poor to modest yields (Ber. 62B, 1398 (1929) and J. Amer. Chem. Soc. 81, 3728, example on page 3735 with 2-pyrid-2-ylethylamine). Furthermore such complexes, including those, for example, of nickel, cobalt and chromium, are so stable that they have been considered to be pseudoaromatic in character (J. Indian Chem. Soc. 54, 127 (1977)). As such, expectedly and unfortunately, excess $H_2S$ gas or related sulfur derivates must be used in order to liberate the biguanidine from the strongly bound biguanidino heavy metal complex such as the copper complex (Inorg. Synth. 7, 56 (1963)). Such syntheses are therefore of little technical value.

Nevertheless, substituted biguanidines and the triazines derived from them have found widespread application as pharmaceuticals, biocides and agrochemicals. Thus the formation and reaction of biguanidines under mild, clean, high yielding conditions is of great importance and a remaining technical challenge.

Remarkably and surprisingly it has been found that aluminium derivatives are particularly suitable for the formation of biguanidines from amines and cyanoguanidines. The reaction is mild, proceeds cleanly, most often under conditions which would not have been expected, based on literature precedent, to lead to addition products, and is of a general nature with respect to the amine (Scheme 1).

Scheme 1:

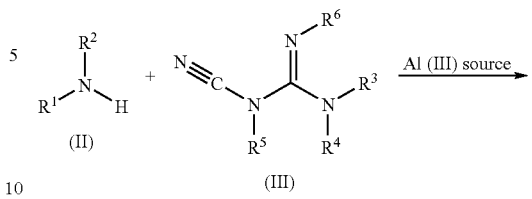

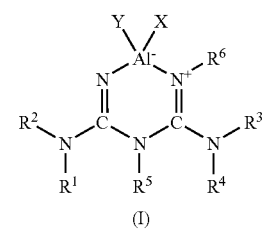

The ligands X and Y of the aluminium complex shown in formula (I) may be furnished from the aluminium source, the solvent or other added components of the reaction mixture. Formula (I) shows only one of the possible resonance structures of the aluminium complex. For instance, the positive charge can also be located at the N-atom linked to the group $R^5$ or at the N-atom of the group $NR^3R^4$. The formula (I) shall represent all resonance structures or tautomers of the aluminium complex, which are in equilibrium with the one shown in formula (I) explicitly or can easily be formed therefrom in the reaction mixture. The same shall be valid also for other chemical formulae considered below.

In case of $R^6$ or $R^5$ or both being hydrogen atoms in formula (III) the starting material is represented by formulae (IIIA) or (IIIB) or (IIIC), respectively, and the reaction can proceed to compounds of formula (I) which are not in a salt form; see compounds of formula (IA), (IB) or (IC) in Schemes 1a, 1b or 1c, respectively (in each case only one of the resonance or tautomeric structures for the aluminium complexes is shown).

Scheme 1a:

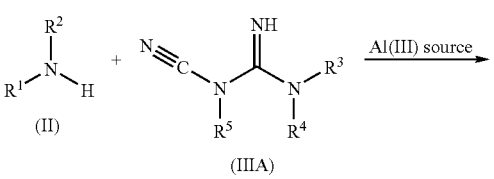

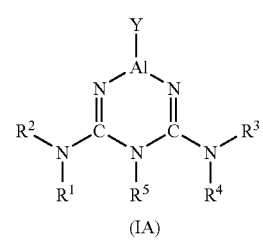

Scheme 1b:

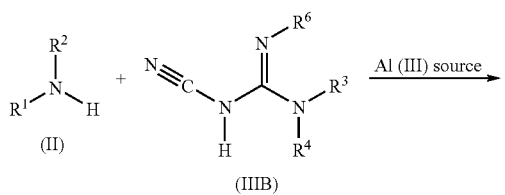

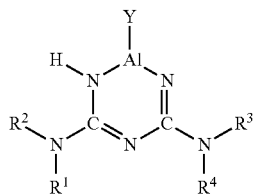

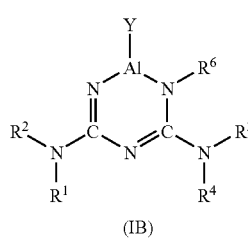
(IB)

Scheme 1c:

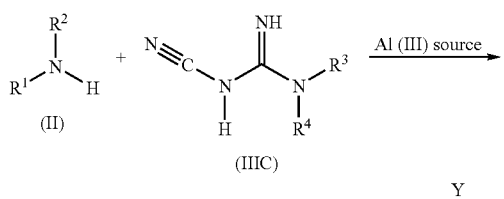

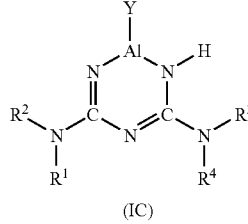
(IC)

Especially, in case of formula (IC) the hydrogen atom in the complex formed can move and then forms tautomers where the saturated hydrogen atom is linked to any of the N-atoms in the compound, mainly to the N-atoms in the ring. The main tautomers in case of $R^5$ and $R^6$ both being hydrogen atoms are the following:

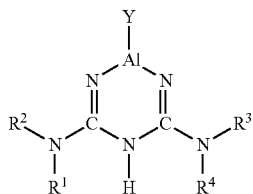
(I-1)

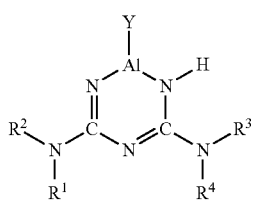
(I-2)

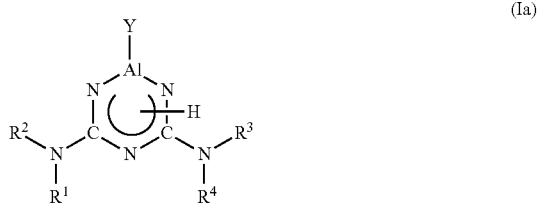
(I-3)

The tautomers together and addition salts thereof (HX added) are also represented by formula (Ia) (non-salt form) or (Ib) (salt form, aluminium complex as anion) or (Ic) (salt form=HX addition salt=aluminium complex as internal salt with higher coordination having four ligands at the Al-atom):

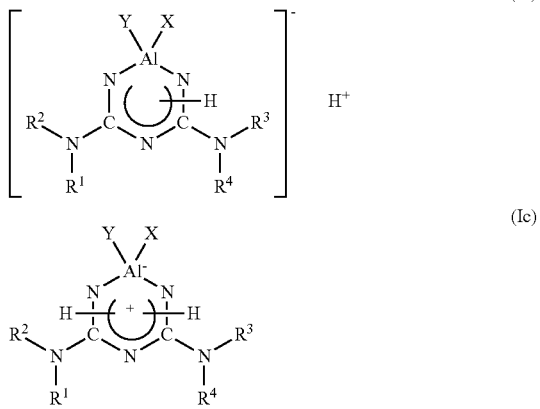

The compounds of the general formula (I) in which $R^5$ and $R^6$ are both hydrogen shall also represent tautomers (Ia) in the non-salt form and salt forms (Ib) and (Ic) and respective resonance structures, and addition complexes of higher coordination (see e.g. complexes with 5 ligands further below), unless specific tautomers or complex structures are specifically considered. The same applies in cases when $R^5$ or $R^6$ or both being different from hydrogen, accordingly.

The invention is thus directed or related to novel aluminium complexes of formula (I), or salts, dimers or polymers thereof (in short "salts thereof"),

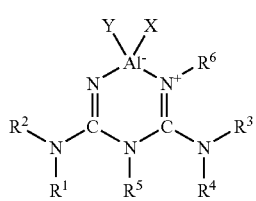
(I)

in which
$R^1$ is $(C_1-C_{18})$alkyl, $(C_2-C_{18})$alkenyl or $(C_2-C_{18})$alkynyl,
  wherein each of the last-mentioned three radicals is unsubstituted or substituted, preferably unsubstituted or substituted by one or more radicals selected from the group consisting of halogen, hydroxy, nitro, carbamoyl, sulfo and radicals of the formulae —O—$R^{1a}$, —S—$R^{1b}$, —S(=O)—$R^{1c}$, —S(=O)$_2$—$R^{1d}$, —N$R^{1e}R^{1f}$, —C(=O)—NH$R^{1g}$, —C(=O)—N$R^{1h}R^{1i}$, —NHC(=O)—N$R^{1j}R^{1k}$ and $A^{1a}$,
  wherein $R^{1a}$, $R^{1b}$, $R^{1c}$, $R^{1d}$, $R^{1e}$, $R^{1f}$, $R^{1g}$, $R^{1h}$, $R^{1i}$, $R^{1j}$, and $R^{1k}$, independently of one another, are $(C_1-C_6)$alkyl, $(C_1-C_6)$haloalkyl, $(C_1-C_6)$alkoxy-$(C_1-C_6)$alkyl or a radical of the formula $A^{1b}$,
  or is a group of the formula $A^1$ or $B^1$,
$R^2$ is H, $(C_1-C_{18})$alkyl, $(C_2-C_{18})$alkenyl or $(C_2-C_{18})$alkynyl,
  wherein each of the last-mentioned three radicals is unsubstituted or substituted, preferably unsubstituted or substituted by one or more radicals selected from the group consisting of halogen, hydroxy, nitro, carbamoyl, sulfo and radicals of the formulae —O—$R^{2a}$, —S—$R^{2b}$, —S(=O)—$R^{2c}$, —S(=O)$_2$—$R^{2d}$, —N$R^{2e}R^{2f}$, —C(=O)—NH$R^{2g}$, —C(=O)—N$R^{2h}R^{2i}$, —NHC(=O)—N$R^{2j}R^{2k}$ and $A^{2a}$,
  wherein $R^{2a}$, $R^{2b}$, $R^{2c}$, $R^{2d}$, $R^{2e}$, $R^{2f}$, $R^{2g}$, $R^{2h}$, $R^{2i}$, $R^{2j}$, and $R^{2k}$, independently of one another, are $(C_1-C_6)$alkyl, $(C_1-C_6)$haloalkyl, $(C_1-C_6)$alkoxy-$(C_1-C_6)$alkyl or a radical of the formula $A^{2b}$,
  or is a group of the formula $A^2$,
$R^3$ is H, $(C_1-C_{18})$alkyl, $(C_2-C_{18})$alkenyl or $(C_2-C_{18})$alkynyl,
  wherein each of the last-mentioned three radicals is unsubstituted or substituted, preferably unsubstituted or substituted by one or more radicals selected from the group consisting of halogen, hydroxy, nitro, carbamoyl, sulfo and radicals of the formulae —O—$R^{3a}$, —S—$R^{3b}$, —S(=O)—$R^{3c}$, —S(=O)$_2$—$R^{3d}$, —N$R^{3e}R^{3f}$, —C(=O)—NH$R^{3g}$, —C(=O)—N$R^{3h}R^{3i}$, —NHC(=O)—N$R^{3j}R^{3k}$ and $A^{3b}$,
  wherein $R^{3a}$, $R^{3b}$, $R^{3c}$, $R^{3d}$, $R^{3e}$, $R^{3f}$, $R^{3g}$, $R^{3h}$, $R^{3i}$, $R^{3j}$, and $R^{3k}$, independently of one another, are $(C_1-C_6)$alkyl, $(C_1-C_6)$haloalkyl, $(C_1-C_6)$alkoxy-$(C_1-C_6)$alkyl or a radical of the formula $A^{3b}$,
  or is a group of the formula $A^3$,
$R^4$ is H, $(C_1-C_{18})$alkyl, $(C_2-C_{18})$alkenyl or $(C_2-C_{18})$alkynyl,
  wherein each of the last-mentioned three radicals is unsubstituted or substituted, preferably unsubstituted or substituted by one or more radicals selected from the group consisting of halogen, hydroxy, nitro, carbamoyl, sulfo and radicals of the formulae —O—$R^{4a}$, —S—$R^{4b}$, —S(=O)—$R^{4c}$, —S(=O)$_2$—$R^{4d}$, —N$R^{4e}R^{4f}$, —C(=O)—NH$R^{4g}$, —C(=O)—N$R^{4h}R^{4i}$, —NHC(=O)—N$R^{4j}R^{4k}$ and $A^{4a}$,
  wherein $R^{4a}$, $R^{4b}$, $R^{4c}$, $R^{4d}$, $R^{4e}$, $R^{4f}$, $R^{4g}$, $R^{4h}$, $R^{4i}$, $R^{4j}$, and $R^{4k}$, independently of one another, are $(C_1-C_6)$alkyl, $(C_1-C_6)$haloalkyl, $(C_1-C_6)$alkoxy-$(C_1-C_6)$alkyl or a radical of the formula $A^{4b}$,
  or is a group of the formula $A^4$,
$R^5$ is H, $(C_1-C_{18})$alkyl, $(C_2-C_{18})$alkenyl or $(C_2-C_{18})$alkynyl,
  wherein each of the last-mentioned three radicals is unsubstituted or substituted, preferably unsubstituted or substituted by one or more radicals selected from the group consisting of halogen, hydroxy, nitro, carbamoyl, sulfo and radicals of the formulae —O—$R^{5a}$, —S—$R^{5b}$, —S(=O)—$R^{5c}$, —S(=O)$_2$—$R^{5d}$, —N$R^{5e}R^{5f}$, —C(=O)—NH$R^{5g}$, —C(=O)—N$R^{5h}R^{5i}$, —NHC(=O)—N$R^{5j}R^{5k}$ and $A^{5a}$,
  wherein $R^{5a}$, $R^{5b}$, $R^{5c}$, $R^{5d}$, $R^{5e}$, $R^{5f}$, $R^{5g}$, $R^{5h}$, $R^{5i}$, $R^{5j}$, and $R^{5k}$, independently of one another, are $(C_1-C_6)$alkyl, $(C_1-C_6)$haloalkyl, $(C_1-C_6)$alkoxy-$(C_1-C_6)$alkyl or a radical of the formula $A^{5b}$,
  or is a group of the formula $A^5$,
$R^6$ is H, $(C_1-C_{18})$alkyl, $(C_2-C_{18})$alkenyl or $(C_2-C_{18})$alkynyl,
  wherein each of the last-mentioned three radicals is unsubstituted or substituted, preferably unsubstituted or substituted by one or more radicals selected from the group consisting of halogen, hydroxy, nitro, carbamoyl, sulfo and radicals of the formulae —O—$R^{6a}$, —S—$R^{6b}$, —S(=O)—$R^{6c}$, —S(=O)$_2$—$R^{6d}$, —N$R^{6e}R^{6f}$, —C(=O)—NH$R^{6g}$, —C(=O)—N$R^{6h}R^{6i}$, —NHC(=O)—N$R^{6j}R^{6k}$ and $A^{6a}$,
  wherein $R^{6a}$, $R^{6b}$, $R^{6c}$, $R^{6d}$, $R^{6e}$, $R^{6f}$, $R^{6g}$, $R^{6h}$, $R^{6i}$, $R^{6j}$, and $R^{6k}$, independently of one another, are $(C_1-C_6)$alkyl, $(C_1-C_6)$haloalkyl, $(C_1-C_6)$alkoxy-$(C_1-C_6)$alkyl or a radical of the formula $A^{6b}$,
  or is a group of the formula $A^6$, or
$R^1$ and $R^2$ or $R^3$ and $R^4$ together with the N-atom linked to each other form a N-heterocyclic ring having 3 to 7 ring atoms and optionally having one or more additional hetero atoms selected from the group consisting of N, O and S and which is unsubstituted or substituted, preferably unsubstituted or substituted by one or more radicals selected from the group consisting of halogen, hydroxy, nitro, carbamoyl, sulfo, $(C_1-C_6)$alkyl, $(C_1-C_6)$haloalkyl, $(C_1-C_6)$alkoxy-$(C_1-C_6)$alkyl, $(C_1-C_6)$alkoxy, $(C_1-C_6)$haloalkoxy, $(C_1-C_6)$alkoxy-$(C_1-C_6)$alkoxy, $(C_1-C_6)$alkylthio, $(C_1-C_6)$alkylsulfinyl, $(C_1-C_6)$haloalkylsulfinyl, $(C_1-C_6)$alkylsulfonyl, $(C_1-C_6)$haloalkylsulfonyl, di-[$(C_1-C_4)$alkyl]-amino, $(C_1-C_4)$alkylamino-carbonyl, di-[$(C_1-C_4)$alkyl]-amino-carbonyl, $(C_1-C_4)$alkylamino-carbonylamino, di-[$(C_1-C_4)$alkyl]-aminocarbonylamino and oxo,
$A^1, A^{1a}, A^{1b}, A^2, A^{2a}, A^{2b}, A^3, A^{3a}, A^{3b}, A^4, A^{4a}, A^{4b}, A^5, A^{5a}, A^{5b}, A^6, A^{6a}$, and $A^{6b}$, independently of one another, are $(C_3-C_9)$cycloalkyl, $(C_4-C_9)$cycloalkenyl, $(C_5-C_9)$cycloalkinyl, aryl or heterocyclyl as a basic cyclic moiety, wherein the basic cyclic moiety is unsubstituted or substituted, preferably
  (a) is unsubstituted or substituted by one or more radicals selected from the group consisting of halogen, hydroxy, nitro, carbamoyl, sulfo, $(C_1-C_6)$alkyl, $(C_1-C_6)$haloalkyl, $(C_1-C_6)$alkoxy-$(C_1-C_6)$alkyl, $(C_1-C_6)$alkoxy, $(C_1-C_6)$haloalkoxy, $(C_1-C_6)$alkoxy-$(C_1-C_6)$alkoxy, $(C_1-C_6)$alkylthio, $(C_1-C_6)$alkylsulfinyl, $(C_1-C_6)$haloalkylsulfinyl, $(C_1-C_6)$alkylsulfonyl, $(C_1-C_6)$haloalkylsulfonyl, di-[$(C_1-C_4)$alkyl]-amino, $(C_1-C_4)$alkylamino-carbonyl, di-[$(C_1-C_4)$alkyl]-amino-carbonyl, $(C_1-C_4)$alkylaminocarbonylamino and di-[$(C_1-C_4)$alkyl]-amino-carbonylamino and, in case of heterocyclyl, also oxo attached to heteroring atoms N or S or in alpha-position of an N-atom as heteroring atom,
  or
  (b) is substituted by or substituted additionally to one or more of the substituents mentioned in (a) by a bridge linked geminal (a 1,1-position), vicinal (a 1,2-position) or in a 1,3-position at the basic cyclic moiety thus forming another carbocyclic or heterocyclic ring together with the part of the basic cyclic moiety between the atoms linked to the bridge,
    preferably by a bridge linked in a vicinal position of the basic cyclic moiety thus forming a carbocyclic or heterocyclic ring condensed with the basic cyclic moiety, wherein the carbocyclic or heterocyclic ring formed is saturated, partly unsaturated, unsaturated, aromatic or heteroaromatic and wherein the bridge is further unsubstituted or substituted,
preferably is further unsubstituted or substituted by one or more radicals selected from the group consisting of halogen, hydroxy, nitro, carbamoyl, sulfo, $(C_1\text{-}C_6)$alkyl, $(C_1\text{-}C_6)$haloalkyl, $(C_1\text{-}C_6)$alkoxy-$(C_1\text{-}C_6)$alkyl, $(C_1\text{-}C_6)$alkoxy, $(C_1\text{-}C_6)$haloalkoxy, $(C_1\text{-}C_6)$alkoxy-$(C_1\text{-}C_6)$alkoxy, $(C_1\text{-}C_6)$alkylthio, $(C_1\text{-}C_6)$alkylsulfinyl, $(C_1\text{-}C_6)$haloalkylsulfinyl, $(C_1\text{-}C_6)$alkylsulfonyl, $(C_1\text{-}C_6)$haloalkylsulfonyl, di-[$(C_1\text{-}C_4)$alkyl]-amino, $(C_1\text{-}C_4)$alkylamino-carbonyl, di-[$(C_1\text{-}C_4)$alkyl]-amino-carbonyl, $(C_1\text{-}C_4)$alkylamino-carbonylamino and di-[$(C_1\text{-}C_4)$alkyl]-aminocarbonylamino, $B^1$ is a group as defined for $R^1$ further linked to the amino group of the group of the formula (I*)

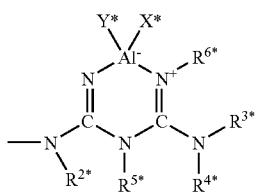

(I*)

wherein $R^{2*}$, $R^{3*}$, $R^{4*}$, $R^{5*}$, $X^*$ and $Y^*$ are independently as defined in formula (I) for $R^2$, $R^3$, $R^4$, $R^5$, X and Y, respectively, X and Y each, independently of one another, are selected from the group consisting of
(i) amino,
(ii) a group of the formula $NR^7R^8$ in which $R^7$ is a radical selected from the group consisting of radicals as defined for and independently of $R^1$, and in which $R^8$ is a radical selected from the group consisting of radicals as defined for and independently of $R^2$, preferably a group of the formula $NR^7R^8$ which is defined as the group $NR^1R^2$ in formula (I),
(iii) hydroxy,
(iv) $(C_1\text{-}C_6)$alkoxy, $(C_1\text{-}C_6)$haloalkoxy, $(C_1\text{-}C_6)$alkoxy-$(C_1\text{-}C_6)$alkoxy and $(C_1\text{-}C_6)$alkylthio,
(v) $(C_1\text{-}C_6)$alkoxy, $(C_1\text{-}C_6)$haloalkoxy, $(C_1\text{-}C_6)$alkoxy-$(C_1\text{-}C_6)$alkoxy and $(C_1\text{-}C_6)$alkylthio, wherein each of the latter 4 radicals is substituted by one or more radicals selected from the group consisting of $(C_3\text{-}C_6)$cycloalkyl, $(C_3\text{-}C_6)$cycloalkoxy,
wherein each of the last-mentioned 2 radicals is unsubstituted or substituted by one or more radicals selected from the group consisting of halogen, hydroxy; carbamoyl, $(C_1\text{-}C_6)$alkyl, $(C_1\text{-}C_6)$haloalkyl, $(C_1\text{-}C_6)$alkoxy-$(C_1\text{-}C_6)$alkyl, $(C_1\text{-}C_6)$alkoxy, $(C_1\text{-}C_6)$haloalkoxy and $(C_1\text{-}C_6)$alkoxy-$(C_1\text{-}C_6)$alkoxy, aryl and aryloxy,
wherein each of the last-mentioned 2 radicals is unsubstituted or substituted by one or more radicals selected from the group consisting of halogen, hydroxy, nitro, carbamoyl, sulfo, $(C_1\text{-}C_6)$alkyl, $(C_1\text{-}C_6)$haloalkyl, $(C_1\text{-}C_6)$alkoxy-$(C_1\text{-}C_6)$alkyl, $(C_1\text{-}C_6)$alkoxy, $(C_1\text{-}C_6)$haloalkoxy, $(C_1\text{-}C_6)$alkoxy-$(C_1\text{-}C_6)$alkoxy, $(C_1\text{-}C_6)$alkylthio, $(C_1\text{-}C_6)$alkylsulfinyl, $(C_1\text{-}C_6)$haloalkylsulfinyl, $(C_1\text{-}C_6)$alkylsulfonyl, $(C_1\text{-}C_6)$haloalkylsulfonyl, di-[$(C_1\text{-}C_4)$alkyl]-amino, $(C_1\text{-}C_4)$alkylamino-carbonyl, di-[$(C_1\text{-}C_4)$alkyl]-amino-carbonyl, $(C_1\text{-}C_4)$alkylamino-carbonylamino and di-[$(C_1\text{-}C_4)$alkyl]-aminocarbonylamino,
(vi) $(C_3\text{-}C_6)$ cycloalkoxy which is unsubstituted or substituted by one or more radicals selected from the group consisting of halogen, hydroxy, carbamoyl, $(C_1\text{-}C_6)$alkyl, $(C_1\text{-}C_6)$haloalkyl, $(C_1\text{-}C_6)$alkoxy-$(C_1\text{-}C_6)$alkyl, $(C_1\text{-}C_6)$alkoxy, $(C_1\text{-}C_6)$haloalkoxy and $(C_1\text{-}C_6)$alkoxy-$(C_1\text{-}C_6)$alkoxy,
(vii) aryloxy which is unsubstituted or substituted,
preferably unsubstituted or substituted by one or more radicals selected from the group consisting of halogen, hydroxy, nitro, carbamoyl, sulfo, $(C_1\text{-}C_6)$alkyl, $(C_1\text{-}C_6)$haloalkyl, $(C_1\text{-}C_6)$alkoxy-$(C_1\text{-}C_6)$alkyl, $(C_1\text{-}C_6)$alkoxy, $(C_1\text{-}C_6)$haloalkoxy, $(C_1\text{-}C_6)$alkoxy-$(C_1\text{-}C_6)$alkoxy, $(C_1\text{-}C_6)$alkylthio, $(C_1\text{-}C_6)$alkylsulfinyl, $(C_1\text{-}C_6)$haloalkylsulfinyl, $(C_1\text{-}C_6)$alkylsulfonyl, $(C_1\text{-}C_6)$haloalkylsulfonyl, di-[$(C_1\text{-}C_4)$alkyl]-amino, $(C_1\text{-}C_4)$alkylamino-carbonyl, di-[$(C_1\text{-}C_4)$alkyl]-amino-carbonyl, $(C_1\text{-}C_4)$alkylamino-carbonylamino and di-[$(C_1\text{-}C_4)$alkyl]-aminocarbonylamino,
and
(viii) acyloxy, acylthio or acylamino, preferably acyloxy, more preferably are each selected from the above groups (ii), (iv), (v), (vi), (vii) and (viii), more preferably from the above groups (ii), (iv) and (v),
or
X and Y together are a divalent group of the formula $-U^1\text{-}D^*\text{-}U^2-$ in which
D* is a hydrocarbon bridge, optionally interrupted by one or more divalent groups of the formula $U^3$ defined below, or, preferably,
is a linear alkylene bridge, a linear $(C_2\text{-}C_{10})$alkenylene bridge, a linear $(C_2\text{-}C_{10})$alkynylene bridge, a $(C_3\text{-}C_9)$cycloalkylene bridge, a phenylene bridge or a bridge consisting of a combination of two or more of said linear acyclic and cyclic moieties having in total 4 to 24 carbon atoms, wherein the bridge in each case is unsubstituted or substituted, preferably unsubstituted or substituted by one or more radicals selected from the group consisting of halogen, hydroxy, nitro, carbamoyl, sulfo, $(C_1\text{-}C_6)$alkyl, $(C_1\text{-}C_6)$haloalkyl, $(C_1\text{-}C_6)$alkoxy-$(C_1\text{-}C_6)$alkyl, $(C_1\text{-}C_6)$alkoxy, $(C_1\text{-}C_6)$haloalkoxy, $(C_1\text{-}C_6)$alkoxy-$(C_1\text{-}C_6)$alkoxy, $(C_1\text{-}C_6)$alkylthio, $(C_1\text{-}C_6)$alkylsulfinyl, $(C_1\text{-}C_6)$haloalkylsulfinyl, $(C_1\text{-}C_6)$alkylsulfonyl, $(C_1\text{-}C_6)$haloalkylsulfonyl, di-[$(C_1\text{-}C_4)$alkyl]-amino, $(C_1\text{-}C_4)$alkylamino-carbonyl, di-[$(C_1\text{-}C_4)$alkyl]-amino-carbonyl, $(C_1\text{-}C_4)$alkylamino-carbonylamino and di-[$(C_1\text{-}C_4)$alkyl]-aminocarbonylamino, and
$U^1$, $U^2$ and $U^3$, independently of each other are selected from the group consisting of NH, NR', O and S, wherein R' is $(C_1\text{-}C_6)$alkyl, hydroxy-$(C_1\text{-}C_6)$alkyl or $(C_1\text{-}C_6)$alkoxy-$(C_1\text{-}C_6)$alkyl,
or
X is a radical as defined above and Y is an organic ligand based on a compound of the formula Y'—H, Y'—$R^L$ or $R^L$—$U^3$-$D^{}$-$U^4$—$R^{LL}$ wherein $D^{}$ is a divalent group as defined for the group D* above, Y' is a radical as defined for Y, $U^3$ is a divalent group as defined for $U^1$ above, $U^4$ is a divalent group as defined for $U^2$ above, each of $R^L$ and $R^{LL}$ is a radical group selected from the group consisting of $(C_1\text{-}C_6)$alkyl, hydroxy-$(C_1\text{-}C_6)$alkyl or $(C_1\text{-}C_6)$alkoxy-$(C_1\text{-}C_6)$alkyl, and wherein the organic ligand is coordinated to the aluminium atom of the complex by a free electron pair of a hetero atom contained therein and selected from the group consisting of N, O and S, or X and Y together are a radical of the formula —U'-D*-U²—$R^{LLL}$ in which $U^1$, $U^2$ and D* are as defined above, and $R^{LLL}$ is a radical selected from the group consisting of $(C_1-C_6)$alkyl, hydroxy-$(C_1-C_6)$alkyl or $(C_1-C_6)$alkoxy-$(C_1-C_6)$alkyl, and wherein the radical —U'-D*-U²—$R^{LLL}$ is additionally coordinated to the aluminium atom of the complex by a free electron pair located at a hetero atom contained in the radical (position represented by Y), preferably located at the heteroatom of the divalent group $U^2$.

In the present patent specification, including the accompanying claims, the aforementioned substituents have the following meanings:

Halogen means fluorine, chlorine, bromine or iodine. In case of a radical "halogen" means a fluorine, chlorine, bromine or iodine atom.

The term "halo" before the name of a radical means that this radical is partially or completely halogenated, that is to say substituted by F, Cl, Br or I in any combination. The expression "$(C_1-C_6)$alkyl" means an unbranched or branched non-cyclic saturated hydrocarbon radical having 1, 2, 3, 4, 5 or 6 carbon atoms (indicated by a range of C-atoms in the parenthesis), such as, for example a methyl, ethyl, propyl, isopropyl, 1-butyl, 2-butyl, 2-methylpropyl or tert-butyl radical. The same applies to alkyl groups in composite radicals such as "alkoxyalkyl".

Alkyl radicals and also in composite groups, unless otherwise defined, preferably have 1 to 4 carbon atoms.

"$(C_1-C_6)$Haloalkyl" means an alkyl group mentioned under the expression "$(C_1-C_6)$alkyl" in which one or more hydrogen atoms are replaced by the same number of identical or different halogen atoms, such as monohaloalkyl, perhaloalkyl, $CF_3$, $CHF_2$, $CH_2F$, $CHFCH_3$, $CF_3CH_2$, $CF_3CF_2$, $CHF_2CF_2$, $CH_2FCHCl$, $CH_2Cl$, $CCl_3$, $CHCl_2$ or $CH_2CH_2Cl$.

"$[(C_1-C_4)alkoxy](C_1-C_6)alkyl$" means $(C_1-C_6)$alkyl which is substituted by $(C_1-C_4)$alkoxy.

"$(C_1-C_6)$Alkoxy" means an alkoxy group whose carbon chain has the meaning given under the expression "$(C_1-C_6)$alkyl". "Haloalkoxy" is, for example, $OCF_3$, $OCHF_2$, $OCH_2F$, $CF_3CF_2O$, $OCH_2CF_3$ or $OCH_2CH_2Cl$.

"$(C_2-C_6)$Alkenyl" means an unbranched or branched non-cyclic carbon chain having a number of carbon atoms which corresponds to this stated range and which contains at least one double bond which can be located in any position of the respective unsaturated radical. "$(C_2-C_6)$alkenyl" accordingly denotes, for example, the vinyl, allyl, 2-methyl-2-propenyl, 2-butenyl, pentenyl, 2-methylpentenyl or the hexenyl group.

"$(C_2-C_6)$alkynyl" means an unbranched or branched non-cyclic carbon chain having a number of carbon atoms which corresponds to this stated range and which contains one triple bond which can be located in any position of the respective unsaturated radical. "$(C_2-C_6)$alkynyl" accordingly denotes, for example, the propargyl, 1-methyl-2-propynyl, 2-butynyl or 3-butynyl group.

yclohexadienyl.

A hydrocarbon radical or bridge is a monovalent or divalent group, respectively, which consists of carbon and hydrogen atoms and which is a linear or branched acyclic or a cyclic group or a group consisting of acyclic and cyclic moieties, and which group is saturated, partly unsaturated, fully unsaturated or aromatic or which group consists of two or more of said structural moieties linked to each other.

Cycloalkyl is a carbocyclic saturated ring system having preferably 3-8 carbon atoms, for example cyclopropyl, cyclobutyl, cyclopentyl or cyclohexyl. In the case of substituted cycloalkyl, cyclic systems with substituents are included, where the substituents are bonded by a double bond on the cycloalkyl radical, for example an alkylidene group such as methylidene. In the case of substituted cycloalkyl, polycyclic aliphatic systems are also included, for example bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, adamantan-1-yl and adamantan-2-yl.

Cycloalkenyl is a carbocyclic, nonaromatic, partially unsaturated ring system having preferably 4-8 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl. In the case of substituted cycloalkenyl, the explanations for substituted cycloalkyl apply correspondingly.

Haloalkyl, -alkenyl and -alkynyl are, respectively, alkyl, alkenyl and alkynyl substituted partly or fully by identical or different halogen atoms, preferably from the group of fluorine, chlorine and bromine, in particular from the group of fluorine and chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example $OCF_3$, $OCHF_2$, $OCH_2F$, $CF_3CF_2O$, $OCH_2CF_3$ and $OCH_2CH_2Cl$; the same applies to haloalkenyl and other halogen-substituted radicals.

Aryl is a mono-, bi- or polycyclic aromatic system, for example phenyl, naphthyl, tetrahydronaphthyl, indenyl, indanyl, pentalenyl, fluorenyl and the like, preferably phenyl.

A heterocyclic radical or ring (heterocyclyl) can be saturated, partially unsaturated, unsaturated or heteroaromatic; unless defined otherwise, it preferably contains one or more, in particular 1, 2 or 3, heteroatoms in the heterocyclic ring, preferably from the group of N, O and S; it is preferably an aliphatic heterocyclyl radical having from 3 to 7 ring atoms or a heteroaromatic radical having 5 or 6 ring atoms. The heterocyclic radical may, for example, be a heteroaromatic radical or ring (heteroaryl), for example a mono-, bi- or polycyclic aromatic system in which at least one ring contains one or more heteroatoms. It is preferably a heteroaromatic ring having a heteroatom from the group of N, O and S, for example pyridyl, pyrrolyl, thienyl or furyl; it is also preferably a corresponding heteroaromatic ring having 2 or 3 heteroatoms, for example pyrimidinyl, pyridazinyl, pyrazinyl, triazinyl, thiazolyl, thiadiazolyl, oxazolyl, isoxazolyl, pyrazolyl, imidazolyl and triazolyl. It is also preferably a partially or fully hydrogenated heterocyclic radical having one heteroatom from the group of N, O and S, for example oxiranyl, oxetanyl, oxolanyl (=tetrahydrofuryl), oxanyl, pyrrolinyl, pyrrolidyl or piperidyl.

It is also preferably a partially or fully hydrogenated heterocyclic radical having 2 heteroatoms from the group of N, O and S, for example piperazinyl, dioxolanyl, oxazolinyl, isoxazolinyl, oxazolidinyl, isoxazolidinyl and morpholinyl.

Possible substituents for a substituted heterocyclic radical include the substituents specified below, and additionally also oxo. The oxo group may also occur on the ring heteroatoms which may exist in various oxidation states, for example in the case of N and S.

Preferred examples of heterocyclyl are a heterocyclic radical having from 3 to 6 ring atoms from the group of pyridyl, thienyl, furyl, pyrrolyl, oxiranyl, 2-oxetanyl, 3-oxetanyl, oxolanyl (=tetrahydrofuryl), pyrrolidyl, piperidyl, especially oxiranyl, 2-oxetanyl, 3-oxetanyl or oxolanyl, or is a heterocyclic radical having two or three heteroatoms, for example pyrimidinyl, pyridazinyl, pyrazinyl, triazinyl, thienyl, thiazolyl, thiadiazolyl, oxazolyl, isoxazolyl, pyrazolyl, triazolyl, piperazinyl, dioxolanyl, oxazolinyl, isoxazolinyl, oxazolidinyl, isoxazolidinyl or morpholinyl.

When a base structure is substituted "by one or more radicals" from a list of radicals (=group) or a generically defined group of radicals, this in each case includes simultaneous substitution by a plurality of identical and/or structurally different radicals.

Substituted radicals, such as a substituted alkyl, alkenyl, alkynyl, aryl, phenyl, benzyl, heterocyclyl and heteroaryl radical, are, for example, a substituted radical derived from the unsubstituted base structure, where the substituents are, for example, one or more, preferably 1, 2 or 3, radicals from the group of halogen, alkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, alkylsulfinyl, alkylsulfonyl and, in the case of cyclic radicals, also alkyl, haloalkyl, alkylthioalkyl, alkoxyalkyl, optionally substituted mono- and dialkylaminoalkyl and hydroxyalkyl; in the term "substituted radicals", such as substituted alkyl, etc., substituents include, in addition to the saturated hydrocarbon radicals mentioned, corresponding unsaturated and aromatic radicals, such as optionally substituted alkenyl, alkynyl, alkenyloxy, alkynyloxy, phenyl, phenoxy, etc. In the case of substituted cylic radicals having aliphatic moieties in the ring, cyclic systems with those substituents which are bonded on the ring by a double bond are also included, for example substituted by an alkylidene group such as methylidene or ethylidene.

It should be noted that in the present case those of the above groups which can easily react under the reaction conditions with the cyanoguanidine of formula (III) or with the amino group of the compound (II) in the process for preparing a compound of the formula (I) are not preferred or need to be masked by a "protective group" if such a functional group shall be implemented.

The substituents mentioned by way of example ("first substituent level") may, when they contain hydrocarbon moieties, optionally be further substituted there ("second substituent level"), for example by one of the substituents as defined for the first substituent level. Corresponding further substituent levels are possible. The term "substituted radical" preferably includes only one or two substituent levels.

Preferred substituents for the substituent levels are, for example, amino, hydroxyl, halogen, nitro, cyano, mercapto, carboxyl, carbonamide, $SF_5$, aminosulfonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulfinyl, alkylsulfonyl, monoalkylaminosulfonyl, dialkylaminosulfonyl, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino and benzylamino.

In the case of radicals with carbon atoms, preference is given to those having from 1 to 6 carbon atoms, preferably from 1 to 4 carbon atoms, in particular 1 or 2 carbon atoms. In general, preferred substituents are those from the group of halogen, e.g. fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Preference is given to the substituents methyl, methoxy, fluorine and chlorine.

Substituted amino, such as mono- or disubstituted amino, is a radical from the group of the substituted amino radicals which are N-substituted, for example, by one or two identical or different radicals from the group of alkyl, alkoxy, acyl and aryl; preferably mono- and dialkylamino, mono- and diarylamino, acylamino, N,N-diacylamino, N-alkyl-N-arylamino, N-alkyl-N-acylamino and N-heterocycles; preference is given to alkyl radicals having from 1 to 4 carbon atoms; aryl is preferably phenyl or substituted phenyl; acyl is as defined below, preferably $(C_1-C_4)$alkanoyl. The same applies to substituted hydroxylamino or hydrazino.

Optionally substituted phenyl is preferably phenyl which is unsubstituted or mono- or polysubstituted, preferably up to trisubstituted, by identical or different radicals from the group of halogen, $(C_1-C_4)$alkyl, $(C_1-C_4)$alkoxy, $(C_1-C_4)$haloalkyl, $(C_1-C_4)$haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

The invention also provides all stereoisomers which are encompassed by formula (I) and mixtures thereof. Such compounds of the formula (I) contain one or more asymmetric carbon atoms or else double bonds which are not stated specifically in the general formulae (I). The possible stereoisomers defined by their specific three-dimensional shape, such as enantiomers, diastereomers, Z- and E-isomers, are all encompassed by the formula (I) and can be obtained from mixtures of the stereoisomers by customary methods or else prepared by stereoselective reactions in combination with the use of stereochemically pure starting materials.

The expression "one or more radicals selected from the group consisting of" in the definition is to be understood as meaning in each case one or more identical or different radicals selected from the stated group of radicals, unless specific limitations are defined expressly.

Acyl is a radical of an organic acid which arises in a formal sense by removal of a hydroxyl group on the acid function, and the organic radical in the acid may also be bonded to the acid function via a heteroatom. Examples of acyl are the —CO—R radical of a carboxylic acid HO—CO—R and radicals of acids derived therefrom, such as those of thiocarboxylic acid, optionally N-substituted iminocarboxylic acids or the radical of carbonic monoesters, N-substituted carbamic acid, sulfonic acids, sulfinic acids, N-substituted sulfonamide acids, phosphonic acids or phosphinic acids.

Acyl is, for example, formyl, alkylcarbonyl such as [($C_1$-$C_4$)alkyl]carbonyl, phenylcarbonyl, alkyloxycarbonyl, phenyloxycarbonyl, benzyloxycarbonyl, alkylsulfonyl, alkylsulfinyl, N-alkyl-1-iminoalkyl and other radicals of organic acids. The radicals may each be substituted further in the alkyl or phenyl moiety, for example in the alkyl moiety by one or more radicals from the group of halogen, alkoxy, phenyl and phenoxy; examples of substituents in the phenyl moiety are the substituents already mentioned above in general for substituted phenyl.

Acyl is preferably an acyl radical in the narrower sense, i.e. a radical of an organic acid in which the acid group is bonded directly to the carbon atom of an organic radical, for example formyl, alkylcarbonyl such as acetyl or [($C_1$-$C_4$)alkyl]carbonyl, optionally substituted phenylcarbonyl, such as benzoyl, alkylsulfonyl, such as methylsulfonyl, alkylsulfinyl, optionally substituted arylsulfonyl, such as phenylsulfonyl or p-tolylsulfonyl and other radicals of organic acids.

The invention also provides all stereoisomers which are encompassed by formula (I) and mixtures thereof. Such compounds of the formula (I) contain one or more asymmetric carbon atoms or else double bonds which are not stated specifically in the general formulae (I). The possible stereoisomers defined by their specific three-dimensional shape, such as enantiomers, diastereomers, Z- and E-isomers, are all encompassed by the formula (I) and can be obtained from mixtures of the stereoisomers by customary methods or else prepared by stereoselective reactions in combination with the use of stereochemically pure starting materials.

Compounds of the stated formula (I) according to the invention in which individual radicals have one of the preferred meanings which have already been stated or are stated hereinbelow and particularly those shown in the Table examples, or in particular those in which two or more of the preferred meanings which have already been stated or which are stated hereinbelow are combined, are of particular interest, mainly because of the ease of preparation or efficacy in the process of forming the aluminium complexes or in the process of forming triazines from the aluminium complexes.

Of particular interest are compounds of formula (I) where a radical selected from the group of radicals $R^1$, $R^2$, $R^3$, $R^4$, $R^5$, $R^6$, X and Y is preferably defined as set forth below.

In the following preferred definitions it is generally to be understood that where symbols are not specifically defined for a specific group of compounds they are to be defined as defined for the compounds in formula (I) or the respective generic formula or for preferred compounds of formula (I) or the respective preferred formula in the description.

$R^1$ preferably is $(C_1-C_{12})$alkyl, $(C_2-C_{12})$alkenyl or $(C_2-C_{12})$alkynyl, more preferably $(C_1-C_6)$alkyl, $(C_2-C_6)$alkenyl or $(C_2-C_6)$alkynyl, wherein each of the last-mentioned six radicals is unsubstituted or substituted, preferably unsubstituted or substituted by one or more radicals selected from the group consisting of halogen, hydroxy, nitro, carbamoyl, sulfo and radicals of the formulae —O—$R^{1a}$, —S—$R^{1b}$, —S(=O)—$R^{1c}$, —S(=O)$_2$—$R^{1d}$, —$NR^{1e}R^{1f}$, —C(=O)—$NHR^{1g}$, more preferably by one or more radicals selected from the group consisting of halogen, hydroxy and radicals of the formulae —O—$R^{1a}$, —S—$R^{1b}$, —S(=O)—$R^{1c}$, —S(=O)$_2$—$R^{1d}$, —$NR^{1e}R^{1f}$ and $A^{1a}$, more preferably by one or more radicals selected from the group consisting of halogen, hydroxy and radicals of the formula —O—$R^{1a}$ and $A^{1a}$, wherein $R^{1a}$, $R^{1b}$, $R^{1c}$, $R^{1d}$, $R^{1e}$, $R^{1f}$, $R^{1g}$, $R^{1h}$, $R^{1i}$, $R^{1j}$, and $R^{1k}$, independently of one another, are $(C_1-C_6)$alkyl, $(C_1-C_6)$haloalkyl, $(C_1-C_6)$alkoxy-$(C_1-C_6)$alkyl or a radical of the formula $A^{1b}$, preferably are $(C_1-C_4)$alkyl, $(C_1-C_4)$haloalkyl, $(C_1-C_4)$alkoxy-$(C_1-C_4)$alkyl or a radical of the formula $A^{1b}$, more preferably are $(C_1-C_4)$alkyl or a radical of the formula $A^{1b}$, or is a group of the formula $A^1$ or $B^1$, preferably of the formula $A^1$, or $R^1$ and $R^2$ together with the N-atom linked to each other form a N-heterocyclic ring having 5 or 6 ring atoms and optionally having 1, 2 or 3 additional hetero atoms selected from the group consisting of N, O and S and which is unsubstituted or substituted by one or more radicals selected from the group consisting of halogen, hydroxy, nitro, carbamoyl, sulfo, $(C_1-C_6)$alkyl, $(C_1-C_6)$haloalkyl, $(C_1-C_6)$alkoxy-$(C_1-C_6)$alkyl, $(C_1-C_6)$alkoxy, $(C_1-C_6)$haloalkoxy, $(C_1-C_6)$alkoxy-$(C_1-C_6)$alkoxy, $(C_1-C_6)$alkylthio, $(C_1-C_6)$alkylsulfinyl, $(C_1-C_6)$haloalkylsulfinyl, $(C_1-C_6)$alkylsulfonyl, $(C_1-C_6)$haloalkylsulfonyl, di-[$(C_1-C_4)$alkyl]-amino, $(C_1-C_4)$alkylamino-carbonyl di-[$(C_1-C_4)$alkyl]-amino-carbonyl, $(C_1-C_4)$alkylaminocarbonylamino, di-[$(C_1-C_4)$alkyl]-aminocarbonylamino and oxo, preferably unsubstituted or substituted by one or more radicals selected from the group consisting of halogen, hydroxy, nitro, $(C_1-C_4)$alkyl, $(C_1-C_4)$haloalkyl, $(C_1-C_4)$alkoxy-$(C_1-C_4)$alkyl, $(C_1-C_4)$alkoxy, $(C_1-C_4)$haloalkoxy, $(C_1-C_4)$alkoxy-$(C_1-C_4)$alkoxy, $(C_1-C_4)$alkylthio, $(C_1-C_4)$alkylsulfonyl, $(C_1-C_4)$haloalkylsulfonyl and oxo, more preferably unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$alkylsulfonyl, $(C_1-C_4)$haloalkylsulfonyl and oxo, $A^1$, $A^{1a}$ and $A^{1b}$, independently of one another, are $(C_3-C_9)$cycloalkyl, $(C_4-C_9)$cycloalkenyl, $(C_5-C_9)$cycloalkinyl, aryl or heterocyclyl as a basic cyclic moiety, wherein the basic cyclic moiety is unsubstituted or substituted, preferably (a) is unsubstituted or substituted by one or more radicals selected from the group consisting of halogen, hydroxy, nitro, carbamoyl, sulfo, $(C_1-C_6)$alkyl, $(C_1-C_6)$haloalkyl, $(C_1-C_6)$alkoxy-$(C_1-C_6)$alkyl, $(C_1-C_6)$alkoxy, $(C_1-C_6)$haloalkoxy, $(C_1-C_6)$alkoxy-$(C_1-C_6)$alkoxy, $(C_1-C_6)$alkylthio, $(C_1-C_6)$alkylsulfinyl, $(C_1-C_6)$haloalkylsulfinyl, $(C_1-C_6)$alkylsulfonyl, $(C_1-C_6)$haloalkylsulfonyl, di-[$(C_1-C_4)$alkyl]-amino, $(C_1-C_4)$alkylamino-carbonyl di-[$(C_1-C_4)$alkyl]-amino-carbonyl, $(C_1-C_4)$alkylaminocarbonylamino and di-[$(C_1-C_4)$alkyl]-amino-carbonylamino and, in case of heterocyclyl, also oxo attached to heteroring atoms N or S or in alpha-position of an N-atom as heteroring atom, more preferably is unsubstituted or substituted in the cyclic moiety by one or more radicals selected from the group consisting of halogen, hydroxy, nitro, sulfo, $(C_1-C_4)$alkyl, $(C_1-C_4)$haloalkyl, $(C_1-C_4)$alkoxy-$(C_1-C_4)$alkyl, $(C_1-C_4)$alkoxy, $(C_1-C_4)$haloalkoxy, $(C_1-C_4)$alkoxy-$(C_1-C_4)$alkoxy, $(C_1-C_4)$alkylthio, $(C_1-C_4)$alkylsulfinyl, $(C_1-C_4)$haloalkyl-sulfinyl, $(C_1-C_4)$alkylsulfonyl and $(C_1-C_4)$haloalkylsulfonyl, more preferably is unsubstituted or substituted in the cyclic moiety by one or radicals selected from the group consisting of halogen, hydroxy, nitro, $(C_1-C_4)$alkyl, $(C_1-C_4)$haloalkyl, $(C_1-C_4)$alkoxy-$(C_1-C_4)$alkyl, $(C_1-C_4)$alkoxy, $(C_1-C_4)$haloalkoxy, $(C_1-C_4)$alkoxy-$(C_1-C_4)$alkoxy, $(C_1-C_4)$alkylthio, $(C_1-C_4)$alkylsulfonyl and $(C_1-C_4)$haloalkylsulfonyl, more preferably is unsubstituted or substituted in the cyclic moiety by one or more radicals selected from the group consisting of halogen, $(C_1-C_4)$alkyl, $(C_1-C_4)$haloalkyl, $(C_1-C_4)$alkoxy, $(C_1-C_4)$haloalkoxy, $(C_1-C_4)$alkylthio and $(C_1-C_4)$alkylsulfonyl, or (b) is substituted by or substituted additionally to one or more of the substituents mentioned in (a) by a bridge linked geminal (a 1,1-position), vicinal (a 1,2-position) or in a 1,3-position at the basic cyclic moiety thus forming another carbocyclic or heterocyclic ring together with the part of the basic cyclic moiety between the atoms linked to the bridge, preferably by a bridge linked in a vicinal position of the basic cyclic moiety thus forming a carbocyclic or heterocyclic ring condensed with the basic cyclic moiety, wherein the carbocyclic or heterocyclic ring formed is saturated, partly unsaturated, unsaturated having 3 to 9 ring atoms or is aromatic or heteroaromatic having 5 or 6 ring atoms and wherein the bridge is furher unsubstituted or substituted, preferably wherein the bridge forming a ring is further unsubstituted or substituted by one or more radicals selected from the group consisting of halogen, hydroxy, nitro, carbamoyl, sulfo, $(C_1-C_6)$alkyl, $(C_1-C_6)$haloalkyl, $(C_1-C_6)$alkoxy-$(C_1-C_6)$alkyl, $(C_1-C_6)$alkoxy, $(C_1-C_6)$haloalkoxy, $(C_1-C_6)$alkoxy-$(C_1-C_6)$alkoxy, $(C_1-C_6)$alkylthio, $(C_1-C_6)$alkylsulfinyl, $(C_1-C_6)$haloalkylsulfinyl, $(C_1-C_6)$alkylsulfonyl, $(C_1-C_6)$haloalkylsulfonyl, di-[$(C_1-C_4)$alkyl]-amino, $(C_1-C_4)$alkylamino-carbonyl, di-[$(C_1-C_4)$alkyl]-amino-carbonyl, $(C_1-C_4)$alkylamino-carbonylamino and di-[$(C_1-C_4)$alkyl]-amino-carbonylamino and, in case of heterocyclyl, also oxo attached to heterering atoms N or S or in alpha-position of an N-atom as heterering atom, or is further benzocondensated wherein the additional annellated benzene ring is unsubstituted or further substituted by one or more radicals as defined for substitution of the bridge which is benzocondensated, more preferably the bridge forming a ring is further unsubstituted or substituted by one or more radicals selected from the group consisting of halogen, hydroxy, nitro, sulfo, $(C_1-C_4)$alkyl, $(C_1-C_4)$haloalkyl, $(C_1-C_4)$alkoxy-$(C_1-C_4)$alkyl, $(C_1-C_4)$alkoxy, $(C_1-C_4)$haloalkoxy, $(C_1-C_4)$alkoxy-$(C_1-C_4)$alkoxy, $(C_1-C_4)$alkylthio, $(C_1-C_4)$alkylsulfinyl, $(C_1-C_4)$haloalkyl-sulfinyl, $(C_1-C_4)$alkylsulfonyl and $(C_1-C_4)$haloalkylsulfonyl, more preferably the bridge forming a ring is further unsubstituted or substituted by one or more radicals selected from the group consisting of halogen, hydroxy, nitro, $(C_1-C_4)$alkyl, $(C_1-C_4)$haloalkyl, $(C_1-C_4)$alkoxy-$(C_1-C_4)$alkyl, $(C_1-C_4)$alkoxy, $(C_1-C_4)$haloalkoxy, $(C_1-C_4)$alkoxy-$(C_1-C_4)$alkoxy, $(C_1-C_4)$alkylthio, $(C_1-C_4)$alkylsulfonyl and $(C_1-C_4)$haloalkylsulfonyl, more preferably the bridge forming a ring is further unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$haloalkoxy, $(C_1-C_4)$alkylthio and $(C_1-C_4)$alkylsulfonyl, $B^1$ is a group as defined for $R^1$ further linked to the amino group of the group of the formula (I*),

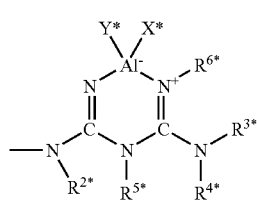

wherein $R^{2*}$, $R^{3*}$, $R^{4*}$, $R^{5*}$, $X^*$ and $Y^*$ are independently as defined in formula (I) for $R^2$, $R^3$, $R^4$, $R^5$, X and Y, respectively.

Examples for $R^1$ are $(C_1-C_{12})$alkyl, $(C_2-C_{12})$alkenyl or $(C_2-C_{12})$alkynyl, more preferably $(C_1-C_6)$alkyl, $(C_2-C_6)$alkenyl or $(C_2-C_6)$alkynyl, wherein each of the last-mentioned six radicals is unsubstituted or substituted, preferably unsubstituted or substituted by one or more radicals selected from the group consisting of halogen, hydroxy, nitro, carbamoyl, sulfo, $(C_1-C_6)$alkoxy, $(C_1-C_6)$haloalkoxy, $(C_1-C_6)$alkoxy-$(C_1-C_6)$alkoxy, $(C_1-C_6)$alkylthio, $(C_1-C_6)$alkylsulfinyl, $(C_1-C_6)$haloalkylsulfinyl, $(C_1-C_6)$alkylsulfonyl, $(C_1-C_6)$haloalkylsulfonyl, di-[$(C_1-C_4)$alkyl]-amino, $(C_1-C_4)$alkylamino-carbonyl, di-[$(C_1-C_4)$alkyl]-amino-carbonyl, $(C_1-C_4)$alkylamino-carbonylamino and di-[$(C_1-C_4)$alkyl]-amino-carbonylamino, $(C_3-C_6)$cycloalkyl, $(C_5-C_6)$cycloalkenyl, phenyl, naphthyl, heterocyclyl, benzocondensated heterocycyl, benzo-$(C_5-C_6)$cycloalkyl, benzo-$(C_5-C_6)$cycloalkenyl, $(C_3-C_6)$cycloalkoxy, benzo-$(C_5-C_6)$cycloalkoxy, $(C_5-C_6)$cycloalkenyloxy, benzo-$(C_5-C_6)$cycloalkenyloxy, phenoxy, naphthoxy, phenylthio, heterocyclyloxy, benzocondensated heterocyclyloxy, heterocyclylthio, benzocondensated heterocyclylthio wherein each of the last-mentioned 19 radicals is unsubstituted or substituted in the cyclic moiety by one or more radicals selected from the group consisting of halogen, hydroxy, nitro, carbamoyl, sulfo, $(C_1-C_4)$alkyl, $(C_1-C_4)$haloalkyl, $(C_1-C_4)$alkoxy-$(C_1-C_4)$alkyl, $(C_1-C_4)$alkoxy, $(C_1-C_4)$haloalkoxy, $(C_1-C_4)$alkoxy-$(C_1-C_4)$alkoxy, $(C_1-C_4)$alkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, di-[$(C_1-C_4)$alkyl]-amino, $(C_1-C_4)$alkylamino-carbonyl di-[$(C_1-C_4)$alkyl]-amino-carbonyl, $(C_1-C_4)$alkylamino-carbonylamino and di-[$(C_1-C_4)$alkyl]-amino-carbonylamino and, in case of heterocyclyl, also oxo attached to heterering atoms N or S or in alpha-position of an N-atom as heterering atom, or are $(C_3-C_6)$cycloalkyl, benzo-$(C_5-C_6)$cycloalkyl, $(C_5-C_6)$cycloalkenyl, benzo-$(C_5-C_6)$cycloalkenyl, phenyl, naphthyl, heterocyclyl, benzocondensated heterocyclyl, wherein each of the last-mentioned 8 radicals is unsubstituted or substituted in the cyclic moiety by one or more radicals selected from the group consisting of halogen, hydroxy, nitro, carbamoyl, sulfo, $(C_1-C_4)$alkyl, $(C_1-C_4)$haloalkyl, $(C_1-C_4)$alkoxy-$(C_1-C_4)$alkyl, $(C_1-C_4)$alkoxy, $(C_1-C_4)$haloalkoxy, $(C_1-C_4)$alkoxy-$(C_1-C_4)$alkoxy, $(C_1-C_4)$alkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, di-[$(C_1-C_4)$alkyl]-amino, $(C_1-C_4)$alkylamino-carbonyl di-[$(C_1-C_4)$alkyl]-amino-carbonyl, $(C_1-C_4)$alkylamino-carbonylamino and di-[$(C_1-C_4)$alkyl]-amino-carbonylamino and, in case of heterocyclyl, also oxo attached to heterering atoms N or S or in alpha-position of an N-atom as heterering atom.

"Heterocyclyl" for the above radicals or substitutents preferably is a heterocyclic saturated, partly saturated, unsaturated or heteroaromatic ring having 3 to 9 ring atoms, preferably 5 or 6 ring atoms in case of a saturated ring or having 5 to 9, preferably 5 or 6 ring atoms in case of partly saturated, unsaturated or heteroaromatic ring, preferably a ring having 1, 2, 3 or 4 hetero ring atoms selected from the group consisting of N, O and S.

Preferably optionally substituted heterocyclyl is saturated heterocyclyl or heteroaryl or benzocondensated derivatives thereof which may be further substituted.

Preferably heteroaryl is: pyrrole, imidazole, triazole, tetrazole, thiophene, thiazole, thiadiazole, oxazole, oxadiazole, pyridine, pyrimidine, piperazine, triazine, tetrazine, benzocondensated derivatives thereof and bicyclic combinations thereof.

Preferably $R^1$ is $(C_1-C_6)$alkyl, $(C_1-C_6)$haloalkyl, phenyl, naphthyl, phenyl$(C_1-C_6)$alkyl, such as benzyl or phenethyl, $(C_2-C_6)$alkenyl, phenyl$(C_2-C_6)$alkenyl, $(C_2-C_6)$alkynyl, phenyl($C_2$-$C_6$)alkynyl, ($C_3$-$C_6$)cycloalkyl, benzo($C_5$-$C_6$)cycloalkyl, such as tetrahydronaphthyl, indanyl, indenyl, fluorenyl, heteroaryl,
wherein the radicals are unsubstituted or substituted in the cyclic moiety, preferably unsubstituted or substituted by one or more radicals mentioned as substituents for $A^1$ above.

Preferably $R^1$ and $R^2$ together with the N-atom linked to each other are a saturated heterocyclic ring having 5 or 6 ring atoms and can have 1 or 2 additional hetero atoms selected from the group consisting of N, O and S and which is unsubstituted or substituted, for example pyrrolidino, morpholino, piperidino, dihydroindolino, dihydroisoindolino, tetrahydroquinolino, tetrahydroisoquinolino, which all may be further substituted, preferably unsubstituted or substituted by one or more radicals mentioned as substituents for $A^1$ above.

Preferably $R^2$
is H, ($C_1$-$C_{12}$)alkyl, ($C_2$-$C_{12}$)alkenyl or ($C_2$-$C_{12}$)alkynyl, more preferably H, ($C_1$-$C_6$)alkyl, ($C_2$-$C_6$)alkenyl or ($C_2$-$C_6$)alkynyl, more preferably H and ($C_1$-$C_4$)alkyl, in particular H,
wherein each of the carbon-containing radicals is unsubstituted or substituted, preferably unsubstituted or substituted by one or more radicals selected from the group consisting of halogen, hydroxy, nitro, carbamoyl, sulfo and radicals of the formulae
—O—$R^{2a}$, —S—$R^{2b}$, —S(=O)—$R^{2c}$, —S(=O)$_2$—$R^{2d}$, —N$R^{2e}R^{2f}$, —C(=O)—NH$R^{2g}$, —C(=O)—N$R^{2h}R^{2i}$, —NHC(=O)—N$R^{2j}R^{2k}$ and $A^{2a}$,
more preferably by one or more radicals selected from the group consisting of halogen, hydroxy and radicals of the formulae
—O—$R^{2a}$, —S—$R^{2b}$, —S(=O)—$R^{2c}$, —S(=O)$_2$—$R^{2d}$ and $A^{2a}$,
more preferably by one or more radicals selected from the group consisting of halogen, hydroxy and radicals of the formula —O—$R^{2a}$ and $A^{2a}$,
wherein $R^{2a}$, $R^{2b}$, $R^{2c}$, $R^{2d}$, $R^{2e}$, $R^{2f}$, $R^{2g}$, $R^{2h}$, $R^{2i}$, $R^{2j}$, and $R^{2k}$, independently of one another, are ($C_1$-$C_6$)alkyl, ($C_1$-$C_6$)haloalkyl, ($C_1$-$C_6$)alkoxy-($C_1$-$C_6$)alkyl or a radical of the formula $A^{2b}$,
preferably are ($C_1$-$C_4$)alkyl, ($C_1$-$C_4$)haloalkyl, ($C_1$-$C_4$)alkoxy-($C_1$-$C_4$)alkyl or a radical of the formula $A^{2b}$,
more preferably are ($C_1$-$C_4$)alkyl or a radical of the formula $A^{2b}$,
or is a group of the formula $A^2$,
wherein $A^2$, $A^{2a}$ and $A^{2b}$, independently of one another, are as defined for $A^1$, $A^{1a}$ and $A_{1b}$, above, preferably wherein
$A^2$, $A^{2a}$ and $A^{2b}$ independently of one another, are ($C_3$-$C_6$)cycloalkyl, phenyl, heterocyclyl, wherein each of the last-mentioned 3 radicals is unsubstituted or substituted in the cyclic moiety, preferably is unsubstituted or substituted in the cyclic moiety by one or more radicals selected from the group consisting of halogen, hydroxy, nitro, carbamoyl, sulfo, ($C_1$-$C_6$)alkyl, ($C_1$-$C_6$)haloalkyl, ($C_1$-$C_6$)alkoxy-($C_1$-$C_6$)alkyl, ($C_1$-$C_6$)alkoxy, ($C_1$-$C_6$)haloalkoxy, ($C_1$-$C_6$)alkoxy-($C_1$-$C_6$)alkoxy, ($C_1$-$C_6$)alkylthio, ($C_1$-$C_6$)alkylsulfinyl, ($C_1$-$C_6$)haloalkylsulfinyl, ($C_1$-$C_6$)alkylsulfonyl, ($C_1$-$C_6$)haloalkylsulfonyl, di-[($C_1$-$C_4$)alkyl]-amino, ($C_1$-$C_4$)alkylamino-carbonyl di-[($C_1$-$C_4$)alkyl]-amino-carbonyl, ($C_1$-$C_4$)alkylamino-carbonylamino and di-[($C_1$-$C_4$)alkyl]-amino-carbonylamino and, in case of heterocyclyl, also oxo attached to heteroring atoms N or S or in alpha-position of an N-atom as heteroring atom,
more preferably is unsubstituted or substituted in the cyclic moiety by one or more radicals selected from the group consisting of halogen, hydroxy, nitro, sulfo, ($C_1$-$C_4$)alkyl, ($C_1$-$C_4$)haloalkyl, ($C_1$-$C_4$)alkoxy-($C_1$-$C_4$)alkyl, ($C_1$-$C_4$)alkoxy, ($C_1$-$C_4$)haloalkoxy, ($C_1$-$C_4$)alkoxy-($C_1$-$C_4$)alkoxy, ($C_1$-$C_4$)alkylthio, ($C_1$-$C_4$)alkylsulfinyl, ($C_1$-$C_4$)haloalkyl-sulfinyl, ($C_1$-$C_4$)alkylsulfonyl and ($C_1$-$C_4$)haloalkylsulfonyl,
more preferably is unsubstituted or substituted in the cyclic moiety by one or more radicals selected from the group consisting of halogen, hydroxy, nitro, ($C_1$-$C_4$)alkyl, ($C_1$-$C_4$)haloalkyl, ($C_1$-$C_4$)alkoxy-($C_1$-$C_4$)alkyl, ($C_1$-$C_4$)alkoxy, ($C_1$-$C_4$)haloalkoxy, ($C_1$-$C_4$)alkoxy-($C_1$-$C_4$)alkoxy, ($C_1$-$C_4$)alkylthio, ($C_1$-$C_4$)alkylsulfonyl and ($C_1$-$C_4$)haloalkylsulfonyl,
more preferably is unsubstituted or substituted in the cyclic moiety by one or more radicals selected from the group consisting of halogen, ($C_1$-$C_4$)alkyl, ($C_1$-$C_4$)haloalkyl, ($C_1$-$C_4$)alkoxy, ($C_1$-$C_4$)haloalkoxy, ($C_1$-$C_4$)alkylthio and ($C_1$-$C_4$)alkylsulfonyl,
or $R^2$ together with $R^1$ and the N-atom linking them are as defined for $NR^1R^2$ above.

Examples for $R^2$ are H or radicals as preferably defined for $R^1$, particularly H, ($C_1$-$C_4$)alkyl, ($C_2$-$C_4$)alkenyl or ($C_2$-$C_4$)alkynyl, ($C_1$-$C_4$)haloalkyl, phenyl, naphthyl, phenyl($C_1$-$C_4$)alkyl, such as benzyl or phenethyl, or ($C_3$-$C_6$)cycloalkyl, wherein each of the last-mentioned 6 radicals is unsubstituted or substituted in the cyclic moiety, preferably unsubstituted or substituted by one or more radicals as defined for substituents at the cyclic groups $A^2$, $A^{2a}$ or $A^{2b}$.

$R^3$, $R^4$, $R^5$ and $R^6$, independently of each other and of $R^1$ and $R^2$, are preferably as defined for $R^2$ or preferably defined for $R^2$.

More preferred $R^3$, $R^4$, $R^5$ and $R^6$, independently of each other, are H or ($C_1$-$C_4$)alkyl, particularly H.

$R^3$ and $R^4$, together with the N-atom may form a ring and then, independently of $NR^1R^2$ are a cyclic group as defined above for $R^1$ and $R^2$ together with the N-atom forming a ring.

X and Y, independently of one another, preferably are each selected from the group consisting of
(i) amino,
(ii) a group of the formula $NR^7R^8$ in which $R^7$ is a radical selected from the group consisting of radicals as defined for and independently of $R^1$, and in which $R^8$ is a radical selected from the group consisting of radicals as defined for and independently of $R^2$, preferably a group of the formula $NR^7R^8$ which is defined as the group $NR^1R^2$ in formula (I),
(iii) hydroxy,
(iv) ($C_1$-$C_4$)alkoxy, ($C_1$-$C_4$)haloalkoxy, ($C_1$-$C_4$)alkoxy-($C_1$-$C_4$)alkoxy and ($C_1$-$C_4$)alkylthio,
(v) ($C_1$-$C_4$)alkoxy, ($C_1$-$C_4$)haloalkoxy, ($C_1$-$C_4$)alkoxy-($C_1$-$C_4$)alkoxy and ($C_1$-$C_4$)alkylthio, wherein each of the latter 4 radicals is substituted by one or more radicals selected from the group consisting of ($C_3$-$C_6$)cycloalkyl, ($C_3$-$C_6$)cycloalkoxy,
wherein each of the last-mentioned 2 radicals is unsubstituted or substituted by one or more radicals selected from the group consisting of halogen, hydroxy, carbamoyl, ($C_1$-$C_4$)alkyl, ($C_1$-$C_4$)haloalkyl, ($C_1$-$C_4$)alkoxy-($C_1$-$C_4$)alkyl, ($C_1$-$C_4$)alkoxy, ($C_1$-$C_4$)haloalkoxy and ($C_1$-$C_4$)alkoxy-($C_1$-$C_4$)alkoxy,
aryl and aryloxy, preferably phenyl or phenoxy,
wherein each of the last-mentioned 4 radicals is unsubstituted or substituted by one or more radicals selected from the group consisting of halogen, hydroxy, nitro, carbamoyl, sulfo, ($C_1$-$C_4$)alkyl, ($C_1$-$C_4$)haloalkyl, ($C_1$-$C_4$)alkoxy-($C_1$-$C_4$)alkyl, ($C_1$-$C_4$)alkoxy, ($C_1$-$C_4$)haloalkoxy, ($C_1$-$C_4$)alkoxy-($C_1$-$C_4$)alkoxy, ($C_1$-$C_4$)alkylthio, ($C_1$-$C_4$)alkylsulfinyl, ($C_1$-$C_4$)haloalkylsulfinyl, $(C_1-C_4)$alkylsulfonyl, $(C_1-C_4)$haloalkylsulfonyl, di-[$(C_1-C_4)$alkyl]-amino, $(C_1-C_4)$alkylamino-carbonyl, di-[$(C_1-C_4)$alkyl]-amino-carbonyl, $(C_1-C_4)$alkylamino-carbonylamino and di-[$(C_1-C_4)$alkyl]-aminocarbonylamino, (vi) $(C_3-C_6)$cycloalkoxy which is unsubstituted or substituted by one or more radicals selected from the group consisting of halogen, hydroxy, carbamoyl, $(C_1-C_4)$alkyl, $(C_1-C_4)$haloalkyl, $(C_1-C_4)$alkoxy-$(C_1-C_4)$alkyl, $(C_1-C_4)$alkoxy, $(C_1-C_4)$haloalkoxy and $(C_1-C_4)$alkoxy-$(C_1-C_4)$alkoxy,
and (vii) aryloxy, preferably phenoxy, wherein each of the last-mentioned two radicals is unsubstituted or substituted by one or more radicals selected from the group consisting of halogen, hydroxy, nitro, carbamoyl, sulfo, $(C_1-C_4)$alkyl, $(C_1-C_4)$haloalkyl, $(C_1-C_4)$alkoxy-$(C_1-C_4)$alkyl, $(C_1-C_4)$alkoxy, $(C_1-C_4)$haloalkoxy, $(C_1-C_4)$alkoxy-$(C_1-C_4)$alkoxy, $(C_1-C_4)$alkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, di-[$(C_1-C_4)$alkyl]-amino, $(C_1-C_4)$alkylamino-carbonyl, di-[$(C_1-C_4)$alkyl]-amino-carbonyl, $(C_1-C_4)$alkylamino-carbonylamino and di-[$(C_1-C_4)$alkyl]-aminocarbonylamino,
and (viii) acyloxy, acylthio or acylamino, preferably acyloxy, wherein the last-mentioned four groups having 1 to 12 carbon atoms, preferably 1 to 8 carbon atoms, and wherein acyl in each group preferably is formyl, $(C_1-C_6)$alkylcarbonyl, $(C_1-C_6)$alkylsulfonyl or optionally substituted arylsulfonyl, more preferably, acyl is acetyl, n- or i-propionyl, n-, iso-, sec- or tert.-butylcarbonyl, or methylsulfonyl, ethylsulfonyl, n-propylsulfonyl, n-butylsulfonyl or phenylsulfonyl
the latter of which is unsubstituted or substituted by one or more radicals selected from the group consisting of halogen, $(C_1-C_4)$alkyl, $(C_1-C_4)$haloalkyl, $(C_1-C_4)$alkoxy-$(C_1-C_4)$alkyl, $(C_1-C_4)$alkoxy, $(C_1-C_4)$haloalkoxy, $(C_1-C_4)$alkoxy-$(C_1-C_4)$alkoxy and $(C_1-C_4)$alkylthio, preferably selected from the group consisting of methyl and ethyl, more preferably X and Y are each selected from the above groups (ii), (iv), (v), (vi), (vii) and (viii), more preferably from the above groups (ii), (iv) and (v), or X and Y together are a divalent group of the formula
—O-D*-O—, —S-D*-S—, —NH-D*-NH—, —O-D*-NH—, —O-D*-S—, —N(CH$_3$)-D*-N(CH$_3$)—, —NH-D*-N(CH$_3$)—, —N(C$_2$H$_5$)-D*-N(C$_2$H$_5$)— or —NH-D*-N(C$_2$H$_5$)—, wherein D* in each of the last-mentioned 9 divalent groups is a linear alkylene bridge, a linear $(C_2-C_{10})$alkenylene bridge, a linear $(C_2-C_{10})$alkynylene bridge, a $(C_3-C_9)$cycloalkylene bridge, a phenylene bridge or a bridge consisting of a combination of two or more of said linear acyclic and cyclic moieties having in total 4 to 18 carbon atoms, wherein the bridge in each case is unsubstituted or substituted by one or more radicals selected from the group consisting of halogen, hydroxy, nitro, carbamoyl, sulfo, $(C_1-C_4)$alkyl, $(C_1-C_4)$haloalkyl, $(C_1-C_4)$alkoxy-$(C_1-C_4)$alkyl, $(C_1-C_4)$alkoxy, $(C_1-C_4)$haloalkoxy, $(C_1-C_4)$alkoxy-$(C_1-C_4)$alkoxy, $(C_1-C_4)$alkylthio, $(C_1-C_4)$alkylsulfinyl, $(C_1-C_4)$haloalkylsulfonyl, $(C_1-C_4)$haloalkylsulfonyl, di-[$(C_1-C_4)$alkyl]-amino, $(C_1-C_4)$alkylamino-carbonyl, di-[$(C_1-C_4)$alkyl]-amino-carbonyl, $(C_1-C_4)$alkylamino-carbonylamino and di-[$(C_1-C_4)$alkyl]-aminocarbonylamino,
or X is a radical as defined above and Y is an organic ligand based on a compound of the formula Y'—H, Y'—R$^L$ or R$^L$—O-D-O—R$^{LL}$, R$^L$—S-D-S—R$^{LL}$, R$^L$—NH-D-NH—R$^{LL}$, R$^L$—O-D-NH—R$^{LL}$, R$^L$—O-D-S—R$^{LL}$, R$^L$—N(CH$_3$)-D-N(CH$_3$)—R$^{LL}$, R$^L$—NH-D-N(CH$_3$)—R$^{LL}$, R$^L$—N(C$_2$H$_5$)-D-N(C$_2$H$_5$)—R$^{LL}$ or R$^L$—NH-D**-N(C$_2$H$_5$)—R$^{LL}$,
wherein D** in each of the 9 last-mentioned compounds is a divalent group as defined for the group D* above, Y' is a radical as defined for Y, and each of R$^L$ and R$^{LL}$ is a radical group selected from the group consisting of $(C_1-C_6)$alkyl, hydroxy-$(C_1-C_6)$alkyl or $(C_1-C_6)$alkoxy-$(C_1-C_6)$alkyl, and wherein the organic ligand is coordinated to the aluminium atom of the complex by a free electron pair of a hetero atom contained therein and selected from the group consisting of N, O and S, or X and Y together are a radical of the formula —O-D-O—R$^{LLL}$, —S-D-S—R$^{LLL}$, —NH-D-NH—R$^{LLL}$, —O-D-NH—R$^{LLL}$, —NH-D-O—R$^{LLL}$, —O-D-S—R$^{LLL}$, —S-D-O—R$^{LLL}$, —N(CH$_3$)-D-N(CH$_3$)—R$^{LLL}$, —NH-D-N(CH$_3$)—R$^{LLL}$, —N(CH$_3$)-D-NH—R$^{LLL}$, —N(C$_2$H$_5$)-D-N(C$_2$H$_5$)—R$^{LLL}$, —NH-D-N(C$_2$H$_5$)—R$^{LLL}$ or —N(C$_2$H$_5$)-D**-NH—R$^{LLL}$, wherein D* in the 13 last-mentioned radicals is as defined above, and R$^{LLL}$ is a radical selected from the group consisting of $(C_1-C_4)$alkyl, hydroxy-$(C_1-C_4)$alkyl or $(C_1-C_4)$alkoxy-$(C_1-C_4)$alkyl, and wherein the radical is additionally coordinated to the aluminium atom of the complex by a free electron pair located at a hetero atom contained in the radical (position represented by Y), preferably located at the heteroatom attached to the group R$^{LLL}$ in the divalent group.

More preferred are compounds (I) in which X and Y, independently of one another, are each selected from the group consisting of (i) amino, (ii) a group of the formula NR$^7$R$^8$ which is defined as the group NR$^1$R$^2$ in formula (I), (iii) hydroxy, (iv) $(C_1-C_6)$alkoxy and $(C_1-C_4)$alkoxy-$(C_1-C_4)$alkoxy, preferably $(C_1-C_4)$alkoxy and $(C_1-C_4)$alkoxy-$(C_1-C_4)$alkoxy in which the O-Atom of the alkoxy group linked directly to the aluminium atom is two carbon atoms away from the O-atom of the terminal alkoxy group; more preferably isopropoxy, 2-butoxy, 2-methoxy-ethoxy, 2-ethoxy-ethoxy, 2-methoxy-1-methyl-ethoxy, 2-ethoxy-1-methyl-ethoxy, (v) $(C_1-C_4)$alkoxy, $(C_1-C_4)$haloalkoxy, $(C_1-C_4)$alkoxy-$(C_1-C_4)$alkoxy and $(C_1-C_4)$alkylthio, wherein each of the latter 4 radicals is substituted by one or more radicals selected from the group consisting of $(C_3-C_6)$cycloalkyl, $(C_3-C_6)$cycloalkoxy,
wherein each of the last-mentioned 2 radicals is unsubstituted or substituted by one or more radicals selected from the group consisting of $(C_1-C_4)$alkyl and $(C_1-C_4)$alkoxy, (vi) $(C_3-C_6)$cycloalkoxy which is unsubstituted or substituted
by one or more radicals selected from the group consisting of $(C_1-C_4)$alkyl and $(C_1-C_4)$alkoxy,
and (vii) phenoxy which is unsubstituted or substituted by one or more radicals selected from the group consisting of halogen, nitro, $(C_1-C_4)$alkyl, $(C_1-C_4)$haloalkyl, $(C_1-C_4)$alkoxy-$(C_1-C_4)$alkyl, $(C_1-C_4)$alkoxy, $(C_1-C_4)$haloalkoxy, $(C_1-C_4)$alkoxy-$(C_1-C_4)$alkoxy, $(C_1-C_4)$alkylthio, $(C_1-C_4)$alkylsulfinyl, $(C_1-C_4)$alkylsulfonyl, di-[$(C_1-C_4)$alkyl]-amino,
and
(viii) acyloxy, acylthio or acylamino, preferably acyloxy, wherein the last-mentioned four groups having 1 to 12 carbon atoms, preferably 1 to 8 carbon atoms, and wherein acyl in each group preferably is formyl, $(C_1-C_6)$alkylcarbonyl or $(C_1-C_6)$alkylsulfonyl or phenylsulfonyl,
the latter of which is unsubstituted or substituted by one or more radicals selected from the group consisting of halogen, $(C_1-C_4)$alkyl and $(C_1-C_4)$alkoxy,
more preferably, acyl is acetyl, n- or i-propionyl, n-, iso-, sec- or tert.-butylcarbonyl, or methylsulfonyl, ethylsulfonyl, n-propylsulfonyl, n-butylsulfonyl, phenylsulfonyl, o-, m- or p-tolylsulfonyl,
more preferably X and Y are each selected from the above groups (ii), (iv), (v), (vi), (vii) and (viii), more preferably from the above groups (ii), (iv) and (v),
or
X and Y together are a divalent group of the formula —O-D*-O—, —S-D*-S—, —NH-D*-NH—, —O-D*-NH—, wherein D* in each of the last-mentioned 4 divalent groups is a linear alkylene bridge, a linear $(C_2-C_6)$alkenylene bridge, a linear $(C_2-C_6)$alkynylene bridge, a $(C_3-C_6)$cycloalkylene bridge, a 1,2-phenylene bridge or a bridge consisting of a combination of two or more of said linear acyclic and cyclic moieties having in total 4 to 12 carbon atoms, wherein the bridge in each case is unsubstituted or substituted by one or more radicals selected from the group consisting of halogen, hydroxy, $(C_1-C_4)$alkyl, $(C_1-C_4)$alkoxy-$(C_1-C_4)$alkyl, $(C_1-C_4)$alkoxy, $(C_1-C_4)$alkoxy-$(C_1-C_4)$alkoxy, $(C_1-C_4)$alkylsulfonyl and di-[$(C_1-C_4)$alkyl]-amino; or
X is a radical as defined above and Y is an organic ligand based on a compound of the formula Y'—H, Y'—$R^L$ or $R^L$—O-D-O—$R^{LL}$, $R^L$—S-D-S—$R^{LL}$, $R^L$—NH-D-NH—$R^{LL}$, $R^L$—O-D-NH—$R^{LL}$, $R^L$—O-D-S—$R^{LL}$, $R^L$—N(CH$_3$)-D-N(CH$_3$)—$R^{LL}$, $R^L$—NH-D-N(CH$_3$)—$R^{LL}$, $R^L$—N(C$_2$H$_5$)-D-N(C$_2$H$_5$)—$R^{LL}$ or $R^L$—NH-D**-N(C$_2$H$_5$)—$R^{LL}$,
wherein D** in each of the 9 last-mentioned compounds is a divalent group as defined for the group D* above, Y' is a radical as defined for Y, and each of $R^L$ and $R^{LL}$ is a radical group selected from the group consisting of $(C_1-C_6)$alkyl, hydroxy-$(C_1-C_4)$alkyl or $(C_1-C_4)$alkoxy-$(C_1-C_4)$alkyl, and wherein the organic ligand is coordinated to the aluminium atom of the complex by a free electron pair of a hetero atom contained therein and selected from the group consisting of N, O and S,
or
X and Y together are a radical of the formula —O-D-O—$R^{LLL}$, —S-D-S—$R^{LLL}$, —NH-D-NH—$R^{LLL}$, —O-D-NH—$R^{LLL}$, —NH-D-O-DS—$R^{LLL}$, —S-D-O—$R^{LLL}$, —N(CH$_3$)-D-N(CH$_3$)—$R^{LLL}$, —NH-D-N(CH$_3$)—$R^{LLL}$, —N(CH$_3$)-D-NH—$R^{LLL}$, —N(C$_2$H$_5$)-D-N(C$_2$H$_5$)—$R^{LLL}$, —NH-D-N(C$_2$H$_5$)—$R^{LLL}$ or —N(C$_2$H$_5$)-D**-NH—$R^{LLL}$, wherein D* in the 13 last-mentioned radicals is as defined above, and $R^{LLL}$ is a radical selected from the group consisting of $(C_1-C_4)$alkyl, hydroxy-$(C_1-C_4)$alkyl or $(C_1-C_4)$alkoxy-$(C_1-C_4)$alkyl, and wherein the radical is additionally coordinated to the aluminium atom of the complex by a free electron pair located at a hetero atom contained in the radical (position represented by Y), preferably located at the heteroatom attached to the group $R^{LLL}$ in the divalent group.

Further preferred are compounds (I) in which
$R^1$, X and Y are as defined above,
$R^2$ is hydrogen,
$R^3$ is hydrogen,
$R^4$ is hydrogen,
$R^5$ is hydrogen and
$R^6$ is hydrogen.

From Al$^{27}$-NMR studies it has been shown that the stereochemical structure of the aluminium complex depends on the ligands X and Y and ligands present in solutions of compounds (I) that in the case that X and Y or other ligands with oxygen atoms are linked to the aluminium atom that the aluminium atom is tetrahedral 4-coordinated or also 5-coordinated, as is known from other cases in aluminium chemistry (see Scheme 2, showing the case for $R^3$ to $R^6$ each being H).

Scheme 2:

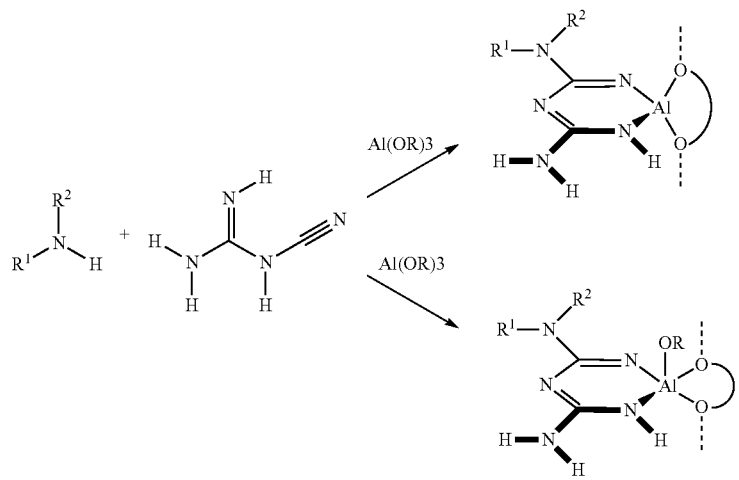

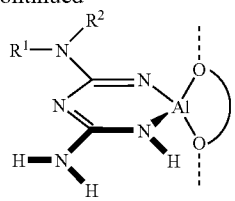

In mono-coordinating solvents such as simple alcohols, for example: methanol, ethanol, isopropanol, 1-butanol, 2-butanol etc. the complex may be variably monomeric or dimeric in nature, depending on the complex concentration in solution or whether the complex is in the solid form (Scheme 3, showing case for $R^3$ to $R^6$ each being H):

Scheme 3:

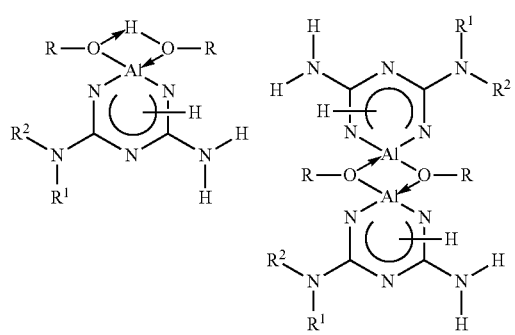

In the presence of more complex solvents which are capable of offering a second coordination site, for example alkoxyalcohols, the complex has been shown (e.g. by $H^1$-NMR and IR) to be monomeric (Scheme 4), and thus being chiral at the aluminium centre. For example, in the presence of 2-ethoxyethanol the aluminium complex formed is shown in Scheme 4, wherein X=O, R"=Et and R'=R=H and 1-methoxy-2-propanol X=O, R"=R=Me, R'"=H, and $R^4$ to $R^6$ in formula (I) are H (only one diastereoisomer at the aluminium centre is shown).

Scheme 4:

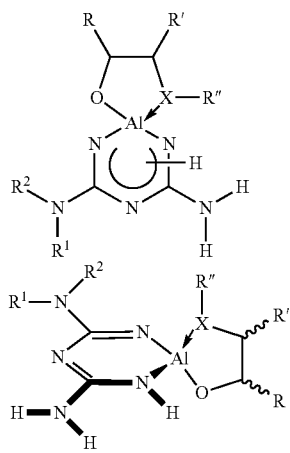

Each structure shown in schemes 1 through 4 is a non limiting graphical representation of all tautomeric isomers of that structure. Furthermore, if the coordinating solvent is chiral then diastereomeric mixtures of complexes may be formed in varying ratios.

Another object of the invention is a process for the preparation of bisguanidine-aluminium complexes of the formula (I) or salts thereof,

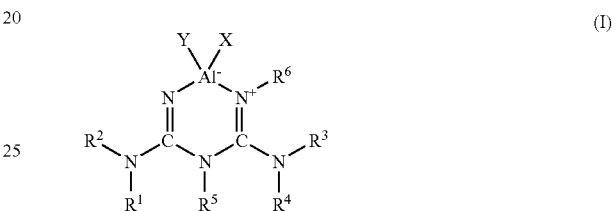

(I)

in which $R^1$ to $R^6$ and X and Y are as defined above, characterized in that a compound (an amine) of the formula (II) or a salt thereof,

(II)

in which $R^1$ and $R^2$ are defined as in the compound of formula (I) to be prepared, is reacted to a compound of the formula (III) or a salt thereof,

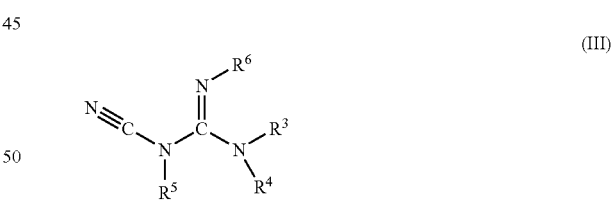

(III)

in which $R^3$, $R^4$, $R^5$ and $R^6$ are defined as in the compound of formula (I) to be prepared, and an aluminium(III) source, optionally, in the presence of a protic additive or solvent selected from the group consisting of alcohols or amines, preferably an aluminium(III) source selected from (i) aluminium salts of the formula (IV),

(IV)

in which
X and Y are as defined in the compound of formula (I) to be prepared, and Z, independently of X, is a leaving group selected from the group of radicals as defined for X or Y,
or
(ii) aluminium salts of the formula (IV'),

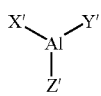

in which
X', Y' and Z' each are selected from the group consisting of radicals as defined for X, Y or Z, respectively and radicals which generate said group X, Y or Z, respectively in the presence of a protic additive or solvent X—H, Y—H or Z—H, respectively, with the proviso that 1, 2 or 3 of the radicals X', Y' and Z' are selected from said radicals which generate radicals X, Y and Z, respectively,
in combination with a protic additive or solvent X—H, Y—H or Z—H wherein each of X, Y and Z are defined as set forth for X and Y in formula (I), and addition salts thereof.

Preferably, the amines of formula (II) are monoamines. If the amines of formula (II) contain another primary or secondary amino group this group may react like the first amino group with the compound of formula (III). In such a case, preferably in case of a diamine with two primary amino groups and where both amino groups react, the compound of formula (I) is obtained where $R^1$ is a group of the formula (B1). Suitable radicals X, Y and Z in compounds (IV) are selected from the group consisting of radicals (i), (ii), (iii), (iv), (v), (vi) and (vii) set forth above for X and Y of the compounds of formula (I).

Suitable radicals X', Y' and Z' in formula (IV') which generate a radical X, Y and Z in the presence of a protic additive or solvent are
H, halogen, $(C_1-C_{18})$alkyl which is unsubstituted or substituted, preferably which is unsubstituted or substituted by one or more radicals selected from the group consisting of halogen, $(C_1-C_6)$alkoxy, $(C_3-C_6)$cycloalkyl, aryl and substituted aryl, or is aryl which is unsubstituted or substituted, preferably which is unsubstituted or substituted by one or more radicals selected from the group consisting of halogen, $(C_1-C_6)$alkyl and $(C_1-C_6)$alkoxy,
and the protic additive or solvent is selected from the type X—H, Y—H or Z—H where X, Y and Z are as defined for X or Y, or preferably defined for X or Y, in the compound (I). Such protic additives are of the type HO-alkyl, HO-aryl, HO-alkylaryl, $NH_3$ or $HNR^1R^2$ to generate groups X, Y and Z of the type —O-alkyl, —O-aryl, —O-alkylaryl, -amino or —$NR^1R^2$, respectively.

Suitable radicals X', Y' and Z' in formula (IV') which generate a radical X, Y and Z in the presence of a protic additive or solvent preferably are
H, halogen, cyano, $(C_1-C_6)$alkyl which is unsubstituted or substituted, preferably which is unsubstituted or substituted by one or more radicals selected from the group consisting of halogen, $(C_1-C_6)$alkoxy, $(C_3-C_6)$cycloalkyl, phenyl and substituted phenyl (preferably phenyl substituted by one or more radicals selected from the group consisting of halogen, $(C_1-C_6)$alkyl and $(C_1-C_6)$alkoxy),
or are phenyl which is unsubstituted or substituted, preferably which is unsubstituted or substituted by one or more radicals selected from the group consisting of halogen, $(C_1-C_6)$alkyl and $(C_1-C_6)$alkoxy.

Suitable radicals X', Y' and Z' in formula (IV') which generate a radical X, Y and Z in the presence of a protic additive or solvent are also those selected from the group consisting of radicals (i), (ii), (iii), (iv), (v), (vi) and (vii) set forth above for X and Y of the compounds of formula (I) if they are used in combination with a protic additive or solvent of the type X—H, Y—H or Z—H if the group X, Y and Z in the protic additive or solvent is more nucleophilic than X', Y' or Z' in the compound of formula (IV') or if the protic additive or solvent is present in a large excess so that an exchange of the ligands occurs.

Suitable compounds of formula (IV) are aluminium trimethoxide [Al(OCH$_3$)$_3$]aluminium triethoxide [Al(OC$_2$H$_5$)$_3$], aluminium tri(n-propoxide) [Al(O-n-C$_3$H$_7$)$_3$], aluminium tri(i-propoxide) [Al(O-i-C$_3$H$_7$)$_3$], aluminium tri(n-butoxide) [Al(O-n-C$_4$H$_9$)$_3$], aluminium tri(sec-butoxide) [Al(O-sec-C$_4$H$_9$)$_3$], aluminium tri(i-butoxide) [Al(O-i-C$_4$H$_9$)$_3$], aluminium tri(tert-butoxide) [Al(O-tert-C$_4$H$_9$)$_3$], aluminium tri(2-methoxy-ethoxide) [Al(O—CH$_2$CH$_2$—O—CH$_3$)$_3$], aluminium tri(2-ethoxy-ethoxide) [Al(O—CH$_2$CH$_2$—O—C$_2$H$_5$)$_3$], aluminium tri(2-methoxy-1-methyl-ethoxide) [Al(O—CH(CH$_3$)CH$_2$—O—CH$_3$)$_3$], aluminium tri(2-ethoxy-1-methyl-ethoxide) {Al[O—CH(CH$_3$)CH$_2$—O—C$_2$H$_5$]$_3$}, or aluminium compounds with mixed radicals such as Al(OCH$_3$)$_2$(OC$_2$H$_5$), Al(OCH$_3$)(OC$_2$H$_5$)$_2$, Al(OCH$_3$)(O-n-C$_3$H$_7$)$_2$, Al(OCH$_3$)$_2$(O-n-C$_3$H$_7$), Al(OC$_5$H$_5$)(O-n-C$_3$H$_7$)$_2$, Al(OC$_2$H$_5$)$_2$(O-n-C$_3$H$_7$), Al(OCH$_3$)(O-i-C$_3$H$_7$)$_2$, Al(OCH$_3$)$_2$(O-i-C$_3$H$_7$), Al(OC$_2$H$_5$)(O-i-C$_3$H$_7$)$_2$, Al(OC$_2$H$_5$)$_2$(O-i-C$_3$H$_7$).

The above compounds (IV) are also suitable aluminium (III) sources of the formula (IV') in the presence of a protic additive or solvent selected from alcohols and/or amines of the type X—H, Y—H or Z—H.

Additionally suitable compounds (IV') which are used in the presence of a protic additive or solvent selected from alcohols and/or amines of the type X—H, Y—H or Z—H are aluminium compounds such as trimethylaluminium [Al(CH$_3$)$_3$], triethylaluminium [Al(C$_2$H$_5$)$_3$], triphenylaluminium [Al(C$_6$H$_5$)$_3$], aluminium hydrides and addition salts thereof such as aluminiumhydride [AlH$_3$], lithiumaluminiumhydride [LiAlH$_4$], alkylaluminiumhydrides such as (CH$_3$)AlH$_2$, (CH$_3$)$_2$AlH, (C$_2$H$_5$)AlH$_2$, (C$_2$H$_5$)$_2$AlH, (n-C$_3$H$_7$)AlH$_2$, (n-C$_3$H$_7$)$_2$AlH, (i-C$_3$H$_7$)AlH$_2$, (i-C$_3$H$_7$)$_2$AlH, (n-C$_4$H$_9$)AlH$_2$, (n-C$_4$H$_9$)$_2$AlH, (sec-C$_4$H$_9$)AlH$_2$, (sec-C$_4$H$_9$)$_2$AlH, (1-C$_4$H$_9$)AlH$_2$, (i-C$_4$H$_9$)$_2$AlH[DIBAL], The reaction can also be performed in substance or in the presence of a solvent or mixtures of solvents. As mentioned above some of the solvents may function as a reactant to form a ligand of the aluminium complex.

Suitable solvents are for example but not limited to:
Organic solvents selected from the group consisting of the chemical class of
ethers, such as dialkylethers (e.g. diethylether) or cyclic aliphatic ethers (e.g. tetrahydrofuran),
saturated or unsaturated aliphatic hydrocarbons, which may be unsubstituted or substituted by one or more radicals selected from the group consisting of halogen, nitro and alkoxy, preferably $(C_1-C_4)$alkoxy, i.e. solvents such as alkanes, alkenes, haloalkanes, nitroalkanes,
aromatic hydrocarbons, which may be unsubstituted or substituted by one or more radicals selected from the group consisting of alkyl (preferably $(C_1-C_4)$alkyl), alkoxy (preferably $(C_1-C_4)$alkoxy), halogen and nitro, i.e. solvents such as aromates, alkylaromates, haloaromates, nitroaromates, alkoxyaromates, alcohols, particularly aliphatic alcohols, such as alkanoles, ω-dioles or ω-polyoles, which may be unsubstituted or substituted, preferably unsubstituted or substituted by one or more radicals from the group consisting of alkoxy (preferably $(C_1\text{-}C_4)$alkoxy), halogen, nitro, amino, $(C_1\text{-}C_4)$alkylamino, and di-$[(C_1\text{-}C_4)$alkyl]-amino, heteroaromates, such as heteroaromatic compounds having 5 or 6 ring atoms and 1 or 2 heteroatoms, particularly 1 heteroatom, selected from the group consisting of N, O and S, such as pyridine or thiophene, sulfones, such as sulfolane, sulfoxides, such as dimethylsulfoxide and amines, such as monoamines, diamines or polyamines.

Preferred are alcohols or mixtures which include an alcohol or alkoxyalcohol are preferred, such as, propanol, isopropanol, isobutanol, cyclohexanol, 2-ethoxy-ethan-1-ol, 2-methoxy-ethan-1-ol, 2-isopropoxy-ethan-1-ol, 2-methoxy-1-methyl-ethan-1-ol (=1-methoxy-isopropanol), 2-ethoxy-1-methyl-ethan-1-ol (=1-ethoxy-isopropanol).

These solvents may also function as protic additives/solvents which determine the ligands of the aluminium complex.

The process of complex formation can be performed at relatively moderate temperatures such as between 50° C. and 140° C. and preferably between 70° C. and 130° C. and especially between 90 and 120° C.

The complex formation preferably is performed with 0.1 to 10.0 equivalents cyanoguanidine of formula (III), more preferably with 1.0 to 3.0 equivalents cyanoguanidine of formula (III), more preferably with 1.0 to 2.0 equivalents of the cyanoguanidine and especially with 1.0 to 1.6 equivalents of the cyanoguanidine, based on 1 equivalent of compound (II) (amine) or salt thereof.

The complex formation is preferably performed with 0.1 to 10.0 equivalents of the aluminium reagent of the formula (IV), more preferably with 1.0 to 3.0 equivalents of the aluminium reagent of the formula (IV), more preferably with 1.0 to 2.0 equivalents of the aluminium reagent and especially with 1.0 to 1.6 equivalents of the aluminium reagent, based on 1 equivalent of compound (II) or salt thereof.

It is known already from Anorg. Chemie, Org. Chemie, Biochem, Biophys., Biol, 347, 1974 that the unsubstituted aluminium biguanidine complex can be prepared from aluminium chloride ($AlCl_3$) and biguanidine ($C_2N_5H_7$). The preparation of substituted complexes has not been known so far.

The compounds of formula (I) or salts thereof (in short "compounds (I)") are aluminium complexes of biguanides and are suitable as intermediates for the preparation of products which otherwise can be prepared also by reaction of the respective free biguanides.

The compounds (I) are preferably suitable for the preparation of heterocyclic compounds, where the aluminium atom is replaced with an optionally substituted carbon atom or heteroaromatic derivatives thereof, such as s-triazines.

Another object of the invention is thus the use of compounds of formula (I) or salts thereof for the preparation of heterocyclic compounds corresponding to formula (I), wherein the aluminium group Al(X)(Y) is replaced with an optionally substituted carbon atom or s-triazine derivatives thereof.

For example, the latter heterocyclic compounds can be prepared by reacting compounds of formula (I) or salts thereof with ketones, wherein the triazine ring is formed by incorporating the carbon atom of the ketone carbonyl group and the oxygen atom of the carbonyl group of the ketone is replaced with the substituted biguanide moiety contained in the compound of formula (I); see, for example, analogous reaction from biguanide and ketone according to J. Med. Chem. 1985, 28, 1728-1740.

More preferred are preparations of heteroaromatic compounds, particularly s-triazines, using compounds (I) in which $R^5$ and $R^6$ are hydrogen.

The novel biguanidino-aluminium complexes of formula (I) and salts thereof (=salts, dimers and polymers thereof) are particularly suitable for the preparation of N-substituted 2,4-diamino-s-triazines by the process as described below.

Another object of the present invention is thus a process for the preparation of compounds of the formula (V) or salts thereof,

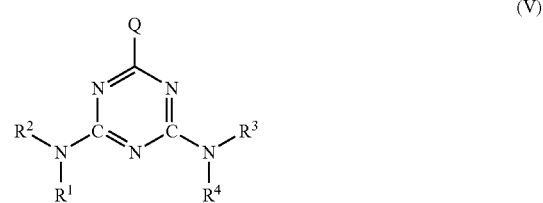

(V)

in which $R^1$, $R^2$, $R^3$ and $R^4$ are as defined above, and

Q is a) hydrogen, $(C_1\text{-}C_{12})$alkyl, $(C_2\text{-}C_{12})$alkenyl or $(C_2\text{-}C_{12})$alkynyl, more preferably $(C_1\text{-}C_6)$alkyl, $(C_2\text{-}C_6)$alkenyl or $(C_2\text{-}C_6)$alkynyl, wherein each of the last-mentioned six radicals is unsubstituted or substituted, preferably unsubstituted or substituted by one or more radicals selected from the group consisting of halogen, hydroxy, —CN, —NO$_2$, —OCN, —SCN, amino, carbamoyl, $(C_1\text{-}C_6)$alkoxy, $(C_1\text{-}C_6)$haloalkoxy, $(C_1\text{-}C_6)$alkoxy-$(C_1\text{-}C_6)$alkoxy, $(C_1\text{-}C_6)$alkylthio, $(C_1\text{-}C_6)$alkylsulfinyl, $(C_1\text{-}C_6)$haloalkylsulfinyl, $(C_1\text{-}C_6)$alkylsulfonyl, $(C_1\text{-}C_6)$haloalkylsulfonyl, $(C_1\text{-}C_4)$alkyl-amino, di-$[(C_1\text{-}C_4)$alkyl]-amino, $(C_1\text{-}C_4)$alkylamino-carbonyl, di-$[(C_1\text{-}C_4)$alkyl]-amino-carbonyl, $(C_1\text{-}C_4)$alkylamino-carbonylamino and di-$[(C_1\text{-}C_4)$alkyl]-amino-carbonylamino, oxo, thiooxo, imino, N—$(C_1\text{-}C_6)$alkyl-imino, N-[phenyl-$(C_1\text{-}C_4)$alkyl]-imino, N—$(C_3\text{-}C_6)$cycloalkyl-imino, N—$[(C_3\text{-}C_6)$cycloalkyl-$(C_1\text{-}C_4)$alkyl]-imino, $[(C_1\text{-}C_6)$alkoxy]-carbonyl, $(C_3\text{-}C_6)$cycloalkyl, $(C_5\text{-}C_6)$cycloalkenyl, phenyl, naphthyl, heterocyclyl, benzocondensated heterocyclyl, benzo-$(C_5\text{-}C_6)$cycloalkyl, benzo-$(C_5\text{-}C_6)$cycloalkenyl, $(C_3\text{-}C_6)$cycloalkoxy, benzo-$(C_5\text{-}C_6)$cycloalkoxy, $(C_5\text{-}C_6)$cycloalkenyloxy, benzo-$(C_5\text{-}C_6)$cycloalkenyloxy, phenoxy, naphthoxy, phenylthio, heterocyclyloxy, benzocondensated heterocyclyloxy, heterocyclylthio, and benzocondensated heterocyclylthio wherein each of the last-mentioned 19 radicals is unsubstituted or substituted in the cyclic moiety by one or more radicals selected from the group consisting of halogen, hydroxy, —CN, NO$_2$, —OCN, —SCN, amino, carbamoyl, $(C_1\text{-}C_4)$alkyl, $(C_1\text{-}C_4)$haloalkyl, $(C_1\text{-}C_4)$alkoxy-$(C_1\text{-}C_4)$alkyl, $(C_1\text{-}C_6)$alkoxy, $(C_1\text{-}C_4)$haloalkoxy, $(C_1\text{-}C_4)$alkoxy-$(C_1\text{-}C_4)$alkoxy, $(C_1\text{-}C_4)$alkylthio, $(C_1\text{-}C_4)$alkylsulfinyl, $(C_1\text{-}C_4)$haloalkylsulfinyl, $(C_1\text{-}C_4)$alkylsulfonyl, $(C_1\text{-}C_4)$haloalkylsulfonyl, $(C_1\text{-}C_4)$alkyl-amino, di-$[(C_1\text{-}C_4)$ alkyl]-amino, (C₁-C₄)alkylamino-carbonyl, di-[(C₁-C₄)alkyl]-amino-carbonyl and (C₁-C₄)alkylamino-carbonylamino, or, preferably, is hydrogen, $(C_1-C_6)$alkyl, $(C_1-C_6)$haloalkyl, hydroxy-$(C_1-C_6)$alkyl or $(C_1-C_6)$alkoxy-$(C_1-C_6)$alkyl; more preferably is $(C_1-C_4)$alkyl or $(C_1-C_4)$haloalkyl, hydroxy-$(C_1-C_4)$alkyl or $(C_1-C_4)$alkoxy-$(C_1-C_4)$alkyl; more preferably is $(C_1-C_4)$haloalkyl, b) or is $(C_3-C_6)$cycloalkyl, benzo-$(C_5-C_6)$cycloalkyl, $(C_5-C_6)$cycloalkenyl, benzo-$(C_5-C_6)$cycloalkenyl, phenyl, naphthyl, heterocyclyl, benzocondensated heterocycyl, wherein each of the last-mentioned 8 radicals is unsubstituted or substituted in the cyclic moiety, preferably unsubstituted or substituted by one or more radicals selected from the group consisting of halogen, hydroxy, —CN, —NO₂, —OCN, —SCN, amino, carbamoyl, $(C_1-C_4)$alkyl, $(C_1-C_4)$haloalkyl, $(C_1-C_4)$alkoxy-$(C_1-C_4)$alkyl, $(C_1-C_4)$alkoxy, $(C_1-C_4)$haloalkoxy, $(C_1-C_4)$alkoxy-$(C_1-C_4)$alkoxy, $(C_1-C_4)$alkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylamino, di-[$(C_1-C_4)$alkyl]-amino, $(C_1-C_4)$alkylamino-carbonyl, di-[$(C_1-C_4)$alkyl]-amino-carbonyl, $(C_1-C_4)$alkylamino-carbonylamino and di-[$(C_1-C_4)$alkyl]-amino-carbonylamino, [$(C_1-C_6)$alkoxy]-carbonyl, $(C_3-C_6)$cycloalkyl, $(C_5-C_6)$cycloalkenyl, phenyl, naphthyl, heterocyclyl, $(C_3-C_6)$cycloalkoxy, $(C_5-C_6)$cycloalkenyloxy, phenoxy, naphthoxy, phenylthio, heterocyclyloxy and heterocyclylthio, wherein each of the last-mentioned 12 radicals is unsubstituted or substituted in the cyclic moiety by one or more radicals selected from the group consisting of halogen, hydroxy, —CN, NO₂, —OCN, —SCN, amino, carbamoyl, $(C_1-C_4)$alkyl, $(C_1-C_4)$haloalkyl, $(C_1-C_4)$alkoxy-$(C_1-C_4)$alkyl, $(C_1-C_6)$alkoxy, $(C_1-C_4)$haloalkoxy, $(C_1-C_4)$alkoxy-$(C_1-C_4)$alkoxy, $(C_1-C_4)$alkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkyl-amino, di-[$(C_1-C_4)$alkyl]-amino, $(C_1-C_4)$alkylamino-carbonyl, di-[$(C_1-C_4)$alkyl]-amino-carbonyl and $(C_1-C_4)$alkylamino-carbonylamino, and, in case of heterocyclyl, also oxo attached to heteroring atoms N or S or in alpha-position of an N-atom as heteroring atom, or, preferably, is $(C_3-C_6)$cycloalkyl which is unsubstituted or substituted by one or more radicals selected from the group consisting of halogen and $(C_1-C_4)$alkyl, c) or is COR, COOR, C(=S)R, C(=O)SR, C(=S)OR, C(=S)SR, wherein R in each of the 6 last-mentioned radicals being $(C_1-C_{18})$alkyl, $(C_3-C_6)$cycloalkyl or phenyl, the latter three radicals being unsubstituted or substituted, preferably unsubstituted or substituted by one or more radicals selected from the group consisting of halogen, CN, nitro, $(C_1-C_6)$alkoxy, $(C_1-C_4)$haloalkoxy, $C_1-C_4)$alkoxy-$(C_1-C_4)$alkoxy, $(C_1-C_4)$alkylthio and in case of cyclic basic radicals also $(C_1-C_4)$alkyl, $(C_1-C_4)$haloalkyl and $(C_1-C_4)$alkoxy-$(C_1-C_4)$alkyl, or is CONR'R" or C(=S)NR'R", wherein each of R' and R" in the two last-mentioned radicals, independently of each other, being hydrogen, $(C_1-C_{18})$alkyl, $(C_3-C_9)$cycloalkyl or phenyl, the latter three radicals being unsubstituted or substituted, preferably unsubstituted or substituted by one or more radicals selected from the group consisting of halogen, CN, nitro, $(C_1-C_6)$alkoxy, $(C_1-C_4)$haloalkoxy, $(C_1-C_4)$alkoxy-$(C_1-C_4)$alkoxy, $(C_1-C_4)$alkylthio and in case of cyclic basic radicals also $(C_1-C_4)$alkyl, $(C_1-C_4)$haloalkyl and $(C_1-C_4)$alkoxy-$(C_1-C_4)$alkyl, or R' and R" together with the nitrogen atom form a 3 to 6-membered heterocyclic ring which can contain one or two additional hetero atoms selected from N, O and S, and which is unsubstituted or substituted by one or more radicals selected from the group consisting of halogen, CN, $(C_1-C_4)$alkyl, $(C_1-C_4)$haloalkyl, $(C_1-C_4)$alkoxy-$(C_1-C_4)$alkyl, $(C_1-C_4)$alkoxy, $(C_1-C_4)$haloalkoxy, $(C_1-C_4)$alkoxy-$(C_1-C_4)$alkoxy and $(C_1-C_4)$alkylthio, characterized in that a compound of the formula (I) or a salt thereof

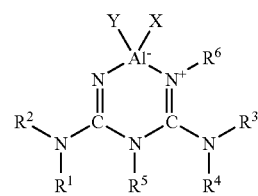

(I)

in which $R^1$, $R^2$, $R^3$ and $R^4$ are as defined in the compound of formula (V) to be prepared and $R^5$ and $R^6$ are hydrogen, is reacted with a compound of the formula (VI)

Q-W* (VI)

in which

Q is as defined in the compound of formula (V) to be prepared and

W* is a carbon atom which bears 3 additional bonds to 1, 2 or 3 leaving groups which are linked by hetero atoms, preferably heteroatoms selected from the group consisting of O, N, F, Cl, Br, I, S, P, Si and metal atoms, (i.e. the carbon atom is linked to 3 leaving groups, each via a single bond, linked to two leaving groups via a single bond and a double bond, respectively, and is linked to one leaving group via a triple bond), and is preferably the functional group —CO—$X^1$ (acid halide group, $X^1$=F, Cl, Br), —CO—CN (acyl nitrile group), —CO—O—COR* (anhydride, R*=Q or R), —CO—O—$X^2$ $(O)_n(O_mR)_t$ (mixed anhydride, X=S, P, B, n=0, 1, 2, 3, m=0, 1, 2, t=1, 2), —CO—O—R (ester group), —CO—O—N=R (acyloxime group)

—CO—NR'R" (amide group, R', R"=H, OR, NR, SR or R, or R' and R" form a ring),

—CN (nitrile group),

—C(=NR')NR" (amidine group, R', R"=H or R, or R and R' form a ring),

—C(=NH)OR (iminoether, imidacid esters),

—C(=NR')OR (iminiumether R'=R (independently)),

—C(=O)SR or —C(=S)OR or —C(=S)SR (thio ester),

—C(=S)NR'R" or —C(=NR')SR (thio amide or iminothioether R', R"=H or R, or R and R' form a ring or R' and R" form a ring)

—C(=NR)$X^1$ (haloimidate group, X=F, Cl, Br),

—C(=N⁺RR')$X^{1-}$ (haloimidium group, R'=R (independently), or R and R' form a ring, $X^{1-}$=F⁻, Cl⁻, Br⁻), —C(—OR)(—OR')$X^1$ (haloacetal group, R'=R (independently or R and R' form a ring, $X^1$=F, Cl, Br), wherein in each subformula group of W* the group R being $(C_1-C_{18})$alkyl, $(C_3-C_6)$cycloalkyl or phenyl, the latter three radicals being unsubstituted or substituted, preferably unsubstituted or substituted by one or more radicals selected from the group consisting of halogen, CN, nitro, $(C_1-C_6)$alkoxy, $(C_1-C_4)$haloalkoxy, $(C_1-C_4)$alkoxy-$(C_1-C_4)$alkoxy, $(C_1-C_4)$alkylthio and in case of cyclic basic radicals also $(C_1-C_4)$alkyl, $(C_1-C_4)$haloalkyl and $(C_1-C_4)$alkoxy-$(C_1-C_4)$alkyl, and in case of a ring formed by R and R' or R' and R" the ring having preferably 3 to 6 ring atoms and being unsubstituted or substituted by one or more radicals selected from the group consisting of halogen, CN, $(C_1-C_4)$alkyl, $(C_1-C_4)$haloalkyl, $(C_1-C_4)$alkoxy-$(C_1-C_4)$alkyl, $(C_1-C_4)$alkoxy, $(C_1-C_4)$haloalkoxy, $(C_1-C_4)$alkoxy-$(C_1-C_4)$alkoxy and $(C_1-C_4)$alkylthio, to give the compound of the formula (V) or a salt thereof.

The triazine formation can also be performed in substance or in the presence of a solvent or mixture of solvents, preferably non-aqueous solvent or solvent mixture, for example in an organic solvent or solvent mixture, which have been mentioned above as suitable for the preparation of compounds of formula (I) too.

Preferred as solvents are alcohols or mixtures which include an alcohol, preferably an alcohol such as methanol, ethanol, propanol, isopropanol, butanol, iso-butanol, tert-butanol, pentanol, hexanol and cyclohexanol and mixtures thereof, more preferably methanol, ethanol, propanol or butanol and mixtures thereof.

The triazine formation preferably is performed between −20° C. and 140° C., more preferably between 0° C. and 120° C. and especially between 20° C. and 100° C.

The triazine formation preferably is performed with 1.0 to 10 equivalents, more preferably with 1.0 to 3.0 equivalents of the species Q-W, more preferably with 1.0 to 2.0 equivalents of the species Q-W and especially with 1.0 to 1.6 equivalents of the species Q-W, based on 1 equivalent of compound (I) or salt thereof.

The triazine formation can also be performed without or preferably in the presence of one or more additives selected from the group consisting of bases and compounds having polar functional groups such hydroxy or amino groups the latter two of which are polar but not particularly basic. The additive often helps in speeding up the reaction, improving the yield, providing the reaction to be performed cleaner and/or at a lower temperature compared to the reaction without the additive.

The following bases can be used as additives for example but not limited to:
a) salts such as an alkoxylate (alkoxide), carbonate, hydrogencarbonate, fluoride, phosphate, hydrogenphosphate, dihydrogenphosphate or hydroxide,
where the counter-ion can be a cation of metal derived from metals, for example, alkali metals such as lithium, sodium, potassium, cesium (=caesium), or alkaline earth metals such as magnesium, calcium, or other metals such as aluminium, or the counter-ion can be ammonium, phosphonium, ammonium or phosphonium substituted by organic groups or can be another organic cation,
b) a tertiary or aromatic amine or mixtures thereof, Reaction mixtures which include one or more alkoxides selected from the group consisting of metal methoxide, metal ethoxide, metal propoxide, metal isopropoxide, metal butoxide, metal iso-butoxide and metal tert-butoxide are especially preferred as base.

The alkoxide, when present, is used preferably in an amount of 0.01 to 5 equivalents and preferably between 0.01 to 2 equivalents, based on 1 equivalent of compound of formula (I) or salt thereof.

The triazine formation can also be performed in the presence of one or more compounds having polar (functional) groups which are of less basic nature than said alkoxides above. Such compounds are preferably selected from the group consisting of polyols, aminoalcohols and polyamines.

Examples for compounds having polar groups are the following compounds including all of their isomers:

ethanediol, propandiol, propantriol, aminoethanol, N-mono- and N,N-disubstituted-aminoethanol, aminopropanol, N-mono- and N,N-disubstituted-aminopropanol, butandiol, butantriol, aminobutanol, N-mono- and N,N-disubstituted-aminobutanol, diethanolamine, N-substituted-diethanolamine, triethanolamine, dipropanolamine, N-substituted-dipropanolamine, ethanediamine, mono-, di-, tri- or tetra-substituted-ethanediamine, propanediamine and mono-, di-, tri- and tetra-substituted-propanediamine, preferably ethanediol, propanediol and butanediol, and mixtures thereof. Especially preferred are 1,2-ethanediol, 1,2-propanediol, 1,2-butanediol and 1-methyl-1,2-propanediol, 1,4-butanediol.

The substance with polar groups, when present, preferably is used in an amount of from 0.01 to 20 equivalents, more preferably of from 0.01 to 10 equivalents and especially of from 0.01 to 5 equivalents, based on 1 equivalent of compound (I) or salt thereof.

The triazine formation can also be performed in the presence of both, one or more base and one or more substances with polar groups, of which mixtures which include one or more of ethanediol, propanediol or butanediol and one or more (metal) methoxide, ethoxide, propoxide, isopropoxide, butoxide, iso-butoxide and tert-butoxide are preferred.

The substance having polar groups, such as the diol, aminoalcohol or diamine, and the (metal) alkoxide often works synergistically resulting in reactions which are quicker and/or cleaner and/or may progress at a lower temperature than may be achieved by either reagent separately.

The triazine formation can also be performed in the presence of an additional salt which may act as a dehydrating agent, for example but not limited to:

sodium sulfate ($Na_2SO_4$), calcium sulfate ($CaSO_4$), calcium halides ($CaCl_2$, $CaBr_2$), magnesium sulfate ($MgSO_4$), magnesium halides ($MgCl_2$, $MgBr_2$).

The additional salt is preferably used in stoichiometric or sub-stoichiometric quantities based on the amount of compound of formula (I).

The triazine formation can also be performed in the presence of a zeolite, clay or other water absorbing substance which may act as a dehydrating agent.

The triazine formation can also be performed in the presence of one or more of the above mentioned additives.

The amine of the formula (II) can also be used in the form of the free base or as a salt or mixed salt of an acid such as, for example: HF, HCl, HBr, HI, $H_2SO_4$, $H_3PO_4$, $RSO_3H$, $RSO_2H$, $RPO_3H_2$, or a complex with $AlX_3$, $BX_3$, $CO_2$, $SO_2$, $SO_3$, $PX_3$, $POX_3$, $PX_5$, $SiX_4$ where X is halogen, a halogen analogue, alkyloxy, aryloxy, alkylamino, alkylarylamino or arylamino or derivatives thereof, where the alkyl groups having 1 to 6 carbon atoms are preferred, and aryl being phenyl is preferred.

The salt of the amine (II) can optionally be used together with the addition of an equivalent amount or less or more than equivalent amount of an organic or inorganic base, preferably a non-aqueous base.

The process for the formation of the triazine can be combined directly with the process for preparing the Al-complex of formula (I) without isolation (or purification) of the compound of formula (I), optionally in a one-pot process.

Preferably, the invention provides a process for the preparation of compounds of formula (V) or salts thereof, characterized in that (a) a compound of the formula (II) or a salt thereof,

(II)

in which $R^1$ and $R^2$ are defined as in the compound of formula (V) to be prepared, is reacted to a compound of the formula (IIIa) or a salt thereof,

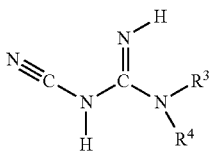
(IIIa)

in which $R^3$ and $R^4$ are defined as in the compound of formula (I) to be prepared,
and an aluminium(II) source, optionally, in the presence of a protic additive or solvent selected from the group consisting of alcohols or amines, preferably an aluminium(III) source selected from
(i) aluminium salts of the formula (IV),

(IV)

in which
X and Y are as defined in the compound of formula (I) to be prepared, and Z, independently of X, is a leaving group selected from the group of radicals as defined for X or Y, or
(ii) aluminium salts of the formula (IV'),

(IV')

in which
X', Y' and Z' each are selected from the group consisting of radicals as defined for X, Y or Z, respectively and radicals which generate said group X, Y or Z, respectively in the presence of a protic additive or solvent X—H, Y—H or Z—H, respectively, with the proviso that 1, 2 or 3 of the radicals X', Y' and Z' are selected from said radicals which generate radicals X, Y and Z, respectively, in combination with a protic additive or solvent X—H, Y—H or Z—H wherein each of X, Y and Z are defined as set forth for X and Y in formula (I), and addition salts thereof, to give a compound of the formula (Ia) or a salt thereof,

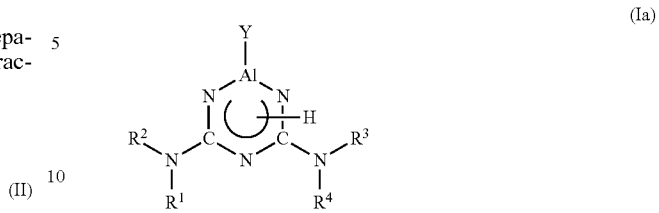
(Ia)

in which $R^1$, $R^2$, $R^3$ and $R^4$, are defined as in the compound of formula (V) to be prepared, and in which Y is as defined in formula (I) further above, and (b) the compound of formula (I) obtained in step (a), optionally without isolation and purification, is reacted with a compound of the formula (VI)

Q-W* (VI)

in which Q is defined as for Q in formula (V) to be prepared, and W* is defined formula (VI) defined further above,
to give a the compound of the formula (V) or a salt thereof.

The process for the preparation of compounds (V) via compounds (I) proceeds with high yield and purity at moderate reaction conditions.

In the following non-limiting examples the amounts and percentages are related to weight unless defined otherwise specifically.

A) PREPARATION EXAMPLES

Abbreviations used in the examples:
hr(s)=hour(s)
ml=milliliter
mp=melting point

A1) 4-Morpholino-6-[(1S)-1-chloroethyl]-1,3,5-triazine-2-amine

A1a) A mixture of 108 g morpholine, 163 g cyanoguanidine, 347 g aluminium isopropoxide and 267 g 1-methoxy-2-propanol were stirred under nitrogen and heated to 90° C. for 22.5 hrs (see example Ia-1.181 of Table II).

A1b) The reaction mixture obtained in A1a was cooled to 70° C., and 530 g methanol was added carefully. After complete addition 178 g methyl (2S)-2-chloro-propionate was added. After 22 hrs at 70° C. the internal the reaction mixture was added to 2400 ml 10% acetic acid at 70° C. Low boiling solvents were removed under a light vacuum (840 ml). The suspension was then cooled to 30° C., filtered and washed with 2×240 g 10% acetic acid and then 2×480 g water. The solid was then dried in vacuo. Product: 199 g, yield 68%, mp: 177-8° C. (see example V-1 of Table I).

A2) N-Benzyl-6-[(1S)-1-hydroxyethyl]-1,3,5-triazine-2,4-diamine

A2a) 130 g benzylamine, 163 g cyanoguanidine and 347 g aluminium isopropoxide were suspended in 267 g 1-methoxy-2-propanol and heated to 90° C. for 10 hrs (see example Ia-1.182 of Table II).

A2b) The reaction mixture obtained in A2b was cooled to 75° C., and 530 g methanol and 153 g methyl S-lactate were added. After 22 hrs the reaction mixture was added to 2400 g 10% acetic acid which had been pre-heated to 70° C. Up to an internal temperature of 88° C. 740 ml solvent was removed by distillation, the mixture cooled to 20° C. and extracted 3 times with 2000 ml ethyl acetate. The combined organic layers were dried over sodium sulfate, filtered and concentrated in vacuo. The resulting product was an oil. Yield of the product: 260 g, 83% (see example V-2 of Table I).

A3) N-Cyclohexyl-6-methoxymethyl-1,3,5-triazine-2,4-diamine

A3a) 50 g cyclohexylamine, 68 g cyanoguanidine and 144 g aluminium isopropoxide were suspended in 110 g 1-methoxy-2-propanol and heated to 90° C. for 4 hrs (see example Ia-1.183 of Table II).

A3b) The reaction mixture obtained in A3a was then cooled to 75° C., and 220 g methanol and 63.7 g methyl methoxyacetate were added. After 16 hrs the reaction mixture was added to 1000 g 10% acetic acid which had been pre-heated to 70° C. Up to an internal temperature of 88° C. 330 ml solvent was removed by distillation, the mixture cooled to 20° C. and extracted 3 times with 1000 ml toluene. The combined organic layers were dried over sodium sulfate, filtered and concentrated in vacuo. The resulting product was an oil which solidified on standing. Product yield: 101 g (85%), mp: 103-6° C. (see example V-3 of Table I).

A4) N-[(1R)-2,3-Dihydro-6-methyl-1H-inden-1-yl]-6-[(1R)-1-fluoroethyl]-1,3,5-triazine-2,4-diamine A4a) A mixture of 53.1 g 1R-1-amino-6-methylindane, 56.5 g cyanoguanidine, 127 g aluminium isopropoxide and 75 g isopropanol were stirred under nitrogen and heated to reflux for 22.5 hrs (see example Ia-1.5 of Table II).

A4b) The reaction mixture obtained in A4a was cooled to 75° C., and 70 g 1,2-propandiol and 182 g methanol were added carefully. After complete addition 45.5 g methyl (2R)-2-fluoro-propionate was added. After 23 hrs at 70° C. the internal temperature the reaction mixture was then added to 870 g 10% acetic acid at 70° C. The suspension was then cooled to 20° C., filtered and washed twice with 160 g 5% acetic acid and then twice with 160 g water. The solid was then dried in vacuo. Product yield: 81.7 g (81%), mp: 135-136° C. (see example V-4 of Table I).

A5) 4-[1,2,3,4-tetrahydroisoquinolin-2-yl]-6-[(1R)-1-fluoroethyl]-1,3,5-triazine-2-amine A5a) A mixture of 48 g 1,2,3,4-tetrahydroisoquinoline, 56.5 g cyanoguanidine, 128 g aluminium isopropoxide and 75 g isopropanol were stirred under nitrogen and heated to reflux for 22 hrs (see example Ia-1.8 of Table II).

A5b) The reaction mixture obtained in A5a was cooled to 75° C., and 70 g 1,2-propandiol and 182 g methanol were added carefully. After complete addition 45.5 g methyl (2R)-2-fluoro-propionate was added. After 23 hrs at 70° C. the internal temperature the reaction mixture was then added to 862 g 10% acetic acid at 70° C. The suspension was then cooled to 20° C., filtered and washed with 2×160 g 5% acetic acid and then twice with 160 g water. The solid was then dried in vacuo. Product yield: 68.5 g (71%), mp: 186-9° C. (see example V-5 of Table I).

A6) N-[1,2,3,4-Tetrahydronaphth-1-yl]-6-[(1S)-1-chloroethyl]-1,3,5-triazine-2,4-diamine A6a) 136.6 g 1,2,3,4-Tetrahydronaphthaline, 122 g cyanoguanidine and 260 g aluminium isopropoxide were suspended in 203 g 1-methoxy-2-propanol and heated to 90° C. for 24 hrs (see example Ia-1.189 of Table II).

A6b) The reaction mixture obtained in A6a was cooled to 75° C., and 400 g methanol and 134 g methyl (2S)-2-chloropropionate were added. After 23 hrs the reaction mixture was added to 1800 g 10% acetic acid which had been pre-heated to 70° C. Up to an internal temperature of 86° C. 550 ml solvent was removed by distillation, the mixture cooled to 20° C. and filtered and washed twice with 180 g 5% acetic acid and then twice with 180 g water. The solid was then dried in vacuo. Product yield: 209 g (76%), mp: 169-70° C. (see example V-6 of Table I).

A7) 4-[1,2,3,4-tetrahydroisoquinolin-2-yl]-6-isopropyl-1,3,5-triazine-2-amine A7a) A mixture of 68.7 g 1,2,3,4-tetrahydroisoquinoline, 67.9 g cyanoguanidine and 144 g aluminium isopropoxide were suspended in 111 g 2-ethoxyethanol and heated to 90° C. for 21 hrs (see example Ia-1.224 of Table II).

A7b) The reaction mixture obtained in A7a was cooled to 75° C., and 222 g methanol, 65 g methyl isobutyrate and 90 g 30% sodium methoxide were added. After 23 hrs the reaction mixture was added to 1000 g 10% acetic acid which had been pre-heated to 70° C. Up to an internal temperature of 86° C. 430 ml solvent was removed by distillation, the mixture cooled to 20° C. and filtered and washed with 2×240 g 5% acetic acid and then twice with 240 g water. The solid was then dried in vacuo. Product yield: 107 g (79%), mp: >255° C. (see example V-7 of Table I).

A8) N-[(1R,2S)-2,6-Dimethyl-2,3-dihydro-1H-inden-1-yl]-6-difluoromethyl-1,3,5-triazine-2,4-diamine A8a) A mixture of 87 g 1R,2S-1-amino-2,6-dimethylindane, 67.9 g cyanoguanidine and 146 g aluminium isopropoxide were suspended in 111 g 1-methoxy-2-propanol and heated to 90° C. for 24 hrs (see example Ia-1.192 of Table II).

A8b) The reaction mixture obtained in A8a was cooled to 70° C. and 222 g methanol, 104 g 1,2 propandiol and 68.9 g methyl difluoropropionate were added. After 23 hrs the reaction mixture was added to 1000 g 10% acetic acid and 1000 ml toluene which had been pre-heated to 70° C. Up to an internal temperature of 87° C. 370 ml solvent was removed by distillation, the mixture cooled to 20° C., the phases separated and the organic phase extracted twice with 500 ml toluene. The combined phases were dried over sodium sulfate and evaporated. The solid was then dried in vacuo. Product yield: 134 g (81%), mp: 87-88° C. (see example V-8 of Table I).

A9) N-[(1R,2S)-2,4,6-Trimethyl-2,3-dihydro-1H-inden-1-yl]-6-[(1S)-1-chloroethyl]-1,3,5-triazine-2,4-diamine A9a) A mixture of 7.6 g 1R,2S-1-amino-2,4,6-trimethylindane, 5.6 g cyanoguanidine and 12.0 g aluminium isopropoxide were suspended in 8.8 g 1-methoxy-2-propanol and heated to 90° C. for 16 hrs (s. expl. Ia-1.198 of Table II).

A9b) The reaction mixture obtained in A9a was cooled to 70° C., and 18.2 g methanol and 6.1 g methyl (2S)-2-chloropropionate were added. After 22 hrs the reaction mixture was added to 10% 85 g acetic acid which had been pre-heated to 70° C. Up to an internal temperature of 87° C. 20 ml solvent was removed by distillation. The mixture was then cooled to 20° C. and filtered and washed twice with 10 g 10% acetic acid and then twice with 20 g water. The solid was then dried in vacuo. Product yield: 6.3 g (45%), mp: 85-87° C. (see example V-9 of Table I).

A10) N-[(1S,2R)-2,6-Dimethyl-2,3-dihydro-1H-inden-1-yl]-biguanidinoaluminiummethoxy-isopropoxide A mixture of 2.62 g (1S,2R)-1-amino-2,6-dimethylindane, 1.40 g cyanoguanidine, 3.40 g aluminium isopropoxide and 2.54 g 1-methoxy-2-propanol were stirred under nitrogen and heated to 103° C. After 22 hrs the reaction was cooled to 50° C. and concentrated in vacuo. The residue was suspended in toluene 20 ml and re-evaporated. The amorphous solid was then dried in vacuo. Structural confirmation was made with $Al^{27}$-NMR, $H^1$-NMR and $C^{13}$-NMR in $D_8$-Isopropanol (see example Ia-1.199 in Table II).

A11) N-[(1R)-cyclobutyl-2-phenyleth-1-yl]-biguandinoaluminiummethoxyisopropoxide A mixture of 3.08 g (1R)-cyclobutyl-2-phenyleth-1-yl-amine, 1.42 g cyanoguanidine, 3.40 g aluminium isopropoxide and 2.54 g 1-methoxy-2-propanol were stirred under nitrogen and heated to 103° C. After 22 hrs the reaction was cooled to 50° C. and concentrated in vacuo. The residue was suspended in toluene 20 ml and re-evaporated. The amorphous solid was then dried in vacuo. Structural confirmation was made with $Al^{27}$-NMR, $H^1$-NMR and $C^{13}$-NMR in $D_8$-Isopropanol (see example Ia-1.215 in Table II).

A12) N-pent-3-ylbiguanidinoaluminiummethoxyisopropoxide

A mixture of 1.37 g 3-pentylamine, 1.40 g cyanoguanidine, 3.40 g aluminium isopropoxide and 3 g isopropanol were stirred under nitrogen and heated to 85° C. After 22 hrs the reaction was cooled to 50° C. and concentrated in vacuo. The residue was suspended in toluene 20 ml and re-evaporated. The amorphous solid was then dried in vacuo. Structural confirmation was made with $Al^{27}$-NMR, $H^1$-NMR and $C^{13}$-NMR in $D_8$-Isopropanol (see example Ia-1.33 in Table II).

The compounds of formula (V) of the following Table I were prepared analogously to the preparation examples A1 (a, b) to A9 (a, b) and A10 to A12 from respective compounds of formula (I) as shown in Table II.

TABLE I

Compounds of formula (Va)

(Va)

| Cpd. | Q | NR$^1$R$^2$ | NR$^3$R$^4$ | Additive | Solvent |
|---|---|---|---|---|---|
| V-1 | (1S)-1-chloroethyl | morpholin-yl | NH$_2$ | — | CH$_3$OH |
| V-2 | (1S)-1-hydroxyethyl | benzylamino | NH$_2$ | — | CH$_3$OH |
| V-3 | methoxymethyl | cyclohexylamino | NH$_2$ | — | CH$_3$OH |
| V-4 | (1R)-1-fluoroethyl | (1R)-2,3-dihydro-6-methyl-1H-inden-1yl-amino | NH$_2$ | 1,2-propanediol | CH$_3$OH |
| V-5 | (1R)-1-fluoroethyl | 1,2,3,4-tetrahydro-isoquinolin-2-yl | NH$_2$ | 1,2-propanediol | CH$_3$OH |
| V-6 | (1S)-1-chloroethyl | (1RS)-1,2,3,4-tetrahydro-napht-1-yl-amino | NH$_2$ | — | CH$_3$OH |
| V-7 | isopropyl | 1,2,3,4-tetrahydro-isoquinolin-2-yl | NH$_2$ | NaOCH$_3$ | CH$_3$OH |
| V-8 | difluoromethyl | (1R,2S)-2,3-dihydro-2,6-dimethyl-1H-inden-1yl-amino | NH$_2$ | 1,2-propanediol | CH$_3$OH |
| V-9 | (1S)-1-chloroethyl | (1R,2S)-2,3-dihydro-2,4,6-trimethyl-1H-inden-1yl-amino | NH$_2$ | — | CH$_3$OH |
| V-10 | (1R)-1-fluoroethyl | (1R,2S)-2,3-dihydro-2,6-dimethyl-1H-inden-1yl-amino | NH$_2$ | NaOCH$_3$ | CH$_3$OH |
| V-11 | (1S)-1-fluoroethyl | (1R,2S)-2,3-dihydro-2,6-dimethyl-1H-inden-1yl-amino | NH$_2$ | NaOC$_2$H$_5$ | C$_2$H$_5$OH |
| V-12 | (1R)-1-fluoroethyl | (1R,2S)-2,3-dihydro-2-methyl-1H-inden-1yl-amino | NH$_2$ | 1,2-propanediol | CH$_3$OH |
| V-13 | difluoromethyl | (1R,2S)-2,3-dihydro-2,6-dimethyl-1H-inden-1yl-amino | NH$_2$ | NaOCH$_3$ | CH$_3$OH |
| V-14 | (1R)-1-fluoroethyl | (1RS)-1,2,3,4-tetrahydro-napht-1-yl-amino | NH$_2$ | NaOCH$_3$, 1,2-propanediol | CH$_3$OH |
| V-15 | (1R)-1-fluoroethyl | 1,2,3,4-tetrahydro-iso-quinolin-2-yl | NH$_2$ | NaOCH$_3$, 1,2-propanediol | CH$_3$OH |
| V-16 | (1R)-1-fluoroethyl | (1R,2R)-2,3-dihydro-2,6-dimethyl-1H-inden-1yl-amino | NH$_2$ | NaOCH$_3$, 1,2-propanediol | CH$_3$OH |
| V-17 | difluoromethyl | (1R)-2,3-dihydro-6-methyl-1H-inden-1yl-amino | NH$_2$ | NaOCH$_3$, | CH$_3$OCH(CH$_3$)$_2$ |
| V-18 | difluoromethyl | 1,2,3,4-tetrahydro-iso-quinolin-2-yl | NH$_2$ | NaOCH$_3$, | CH$_3$OCH(CH$_3$)$_2$ |
| V-19 | 1-fluoro-1-methylethyl | (1R)-2,3-dihydro-6-methyl-1H-inden-1yl-amino | NH$_2$ | NaOCH$_3$, 1,2-propanediol | CH$_3$OCH(CH$_3$)$_2$ |
| V-20 | 1-fluoro-1-methylethyl | (1R,S)-1-cyclobutyl-2-phenyleth-1-yl-amino | NH$_2$ | NaOCH$_3$, 1,2-propanediol | CH$_3$OCH(CH$_3$)$_2$ |
| V-21 | 1-fluoro-1-methylethyl | (1R)-cyclobutyl-2-phenyleth-1-yl-amino | NH$_2$ | NaOCH$_3$, 1,2-propanediol | C$_2$H$_5$OC$_2$H$_4$OH |
| V-22 | (1R)-1-fluoroethyl | (1R)-cyclobutyl-2-phenyleth-1-yl-amino | NH$_2$ | NaOCH$_3$, 1,2-propanediol | CH$_3$OCH(CH$_3$)$_2$ |
| V-23 | (1S)-1-fluoroethyl | (1R)-cyclobutyl-2-phenyleth-1-yl-amino | NH$_2$ | NaOCH$_3$, 1,2-propanediol | CH$_3$OCH(CH$_3$)$_2$ |
| V-24 | 1-fluoro-1-methylethyl | (2R,S)-1-methyl-2-(3,5-dimethylphenyloxy)eth-1-yl-amino | NH$_2$ | NaOCH$_3$ | CH$_3$OH |
| V-25 | 1-fluoro-1-methylethyl | (1R)-1-methyl-2-(3,5-dimethylphenyloxy)eth-1-yl-amino | NH$_2$ | NaOCH$_3$ | C$_2$H$_5$OC$_2$H$_4$OH |
| V-26 | 1-fluoro-1-methylethyl | (1S)-1-methyl-2-(3,5-dimethylphenyloxy)eth-1-yl-amino | NH$_2$ | NaOCH$_3$ | CH$_3$OH |
| V-27 | 1-fluoro-1-methylethyl | 1,1-dicyclopropylmethyl-amino | NH$_2$ | NaOCH$_3$ | CH$_3$OH |

TABLE I-continued

Compounds of formula (Va)

(Va)

| Cpd. | Q | NR¹R² | NR³R⁴ | Additive | Solvent |
|---|---|---|---|---|---|
| V-28 | 1-fluoro-1-methylethyl | pent-3-ylamino | NH₂ | NaOCH₃ | CH₃OH |
| V-29 | 1-fluoro-1-methylethyl | (4RS)-3,4-dihydro-2H-chromen-4-yl-amino | NH₂ | NaOCH₃ | CH₃OH |
| V-30 | 1-fluoro-1-methylethyl | (4R)-3,4-dihydro-2H-chromen-4-yl-amino | NH₂ | NaOCH₃ | CH₃OH |
| V-31 | 1-fluoro-1-methylethyl | (4S)-3,4-dihydro-2H-chromen-4-yl-amino | NH₂ | NaOCH₃ | CH₃OH |
| V-32 | 1-fluoro-1-methylethyl | (3RS,4RS)-3-methyl-3,4-dihydro-2H-chromen-4-yl-amino | NH₂ | NaOCH₃, 1,2-propanediol | CH₃OCH(CH₃)₂ |
| V-33 | 1-fluoro-1-methylethyl | (3R,4R)-3-methyl-3,4-dihydro-2H-chromen-4-yl-amino | NH₂ | NaOCH₃, 1,2-propanediol | CH₃OCH(CH₃)₂ |
| V-34 | 1-fluoro-1-methylethyl | (3S,4S)-3-methyl-3,4-dihydro-2H-chromen-4-yl-amino | NH₂ | NaOCH₃, 1,2-propanediol | CH₃OCH(CH₃)₂ |
| V-35 | 1-fluoro-1-methylethyl | (1RS)-1-cyclopropylethyl-amino | NH₂ | NaOCH₃ | CH₃OH |
| V-36 | 1-fluoro-1-methylethyl | (1R)-1-cyclopropylethyl-amino | NH₂ | NaOCH₃ | CH₃OH |
| V-37 | 1-fluoro-1-methylethyl | (1S)-1-cyclopropylethyl-amino | NH₂ | NaOCH₃ | CH₃OH |
| V-38 | 1-fluoro-propyl | (1RS)-1-(4-chlorphenyl)eth-1-yl-amino | NH₂ | NaOCH₃ | C₂H₅OC₂H₄OH |
| V-39 | 1-fluoro-propyl | (1R)-1-(4-chlorphenyl)eth-1-yl-amino | NH₂ | NaOCH₃ | C₂H₅OC₂H₄OH |
| V-40 | 1-fluoro-propyl | (1S)-1-(4-chlorphenyl)eth-1-yl-amino | NH₂ | NaOCH₃ | C₂H₅OC₂H₄OH |
| V-41 | (1S)-1-chloroethyl | (1R)-1,2,3,4-tetrahydro-napht-1-yl-amino | NH₂ | — | CH₃OH |
| V-42 | (1S)-1-chloroethyl | (1S)-1,2,3,4-tetrahydro-napht-1-yl-amino | NH₂ | — | CH₃OH |
| V-43 | (1R)-1-fluoroethyl | (1R)-1,2,3,4-tetrahydro-napht-1-yl-amino | NH₂ | NaOCH₃, 1,2-propanediol | CH₃OH |
| V-44 | (1R)-1-fluoroethyl | (1S)-1,2,3,4-tetrahydro-napht-1-yl-amino | NH₂ | NaOCH₃, 1,2-propanediol | CH₃OH |
| V-45 | (1S)-1-chloroethyl | morpholin-yl | NHBz | — | CH₃OH |
| V-46 | (1S)-1-hydroxyethyl | benzylamino | NHBz | — | CH₃OH |
| V-47 | methoxymethyl | cyclohexylamino | NHBz | — | CH₃OH |
| V-48 | (1R)-1-fluoroethyl | (1R)-2,3-dihydro-6-methyl-1H-inden-1yl-amino | NHBz | 1,2-propanediol | CH₃OH |
| V-49 | (1R)-1-fluoroethyl | 1,2,3,4-tetrahydro-isoquinolin-2-yl | NHBz | 1,2-propanediol | CH₃OH |
| V-50 | (1S)-1-chloroethyl | 1,2,3,4-tetrahydro-napht-1-yl-amino | NHBz | — | CH₃OH |
| V-51 | (1S)-1-fluoroethyl | 1,2,3,4-tetrahydro-isoquinolin-2-yl | NHBz | NaOCH₃ | CH₃OH |
| V-52 | difluoromethyl | (1R,2S)-2,3-dihydro-2,6-dimethyl-1H-inden-1yl-amino | NHBz | 1,2-propanediol | CH₃OH |
| V-53 | (1S)-1-fluoroethyl | (1R,2S)-2,3-dihydro-2,4,6-trimethyl-1H-inden-1yl-amino | NHBz | — | CH₃OH |
| V-54 | (1R)-1-fluoroethyl | (1R,2S)-2,3-dihydro-2,6-dimethyl-1H-inden-1yl-amino | NHBz | NaOCH₃ | CH₃OH |
| V-55 | (1S)-1-fluoroethyl | (1R,2S)-2,3-dihydro-2,6-dimethyl-1H-inden-1yl-amino | NHBz | NaOC₂H₅ | C₂H₅OH |
| V-56 | (1R)-1-fluoroethyl | (1R,2S)-2,3-dihydro-2-methyl-1H-inden-1yl-amino | NHBz | 1,2-propanediol | CH₃OH |
| V-57 | difluoromethyl | (1R,2S)-2,3-dihydro-2,6-dimethyl-1H-inden-1yl-amino | NHBz | NaOCH₃ | CH₃OH |
| V-58 | (1R)-1-fluoroethyl | 1,2,3,4-tetrahydro-napht-1-yl-amino | NHBz | NaOCH₃, 1,2-propanediol | CH₃OH |
| V-59 | (1R)-1-fluoroethyl | 1,2,3,4-tetrahydro-isoquinolin-2-yl | NHBz | NaOCH₃, 1,2-propanediol | CH₃OH |
| V-60 | (1R)-1-fluoroethyl | (1R,2R)-2,3-dihydro-2,6-dimethyl-1H-inden-1yl-amino | NHBz | NaOCH₃, 1,2-propanediol | CH₃OH |
| V-61 | difluoromethyl | (1R)-2,3-dihydro-6-methyl-1H-inden-1yl-amino | NHBz | NaOCH₃, 1,2-propanediol | CH₃OCH(CH₃)₂ |
| V-62 | difluoromethyl | 1,2,3,4-tetrahydro-isoquinolin-2-yl | NHBz | NaOCH₃, 1,2-propanediol | CH₃OCH(CH₃)₂ |
| V-63 | 1-fluoro-1-methylethyl | (1R)-2,3-dihydro-6-methyl-1H-inden-1yl-amino | NHBz | NaOCH₃, 1,2-propanediol | CH₃OCH(CH₃)₂ |
| V-64 | 1-fluoro-1-methylethyl | (1RS)-1-cyclobutyl-2-phenyleth-1-yl-amino | NHBz | NaOCH₃, 1,2-propanediol | CH₃OCH(CH₃)₂ |
| V-65 | 1-fluoro-1-methylethyl | (1R)-cyclobutyl-2-phenyleth-1-yl-amino | NHBz | NaOCH₃, 1,2-propanediol | C₂H₅OC₂H₄OH |
| V-66 | (1R)-1-fluoroethyl | (1R)-cyclobutyl-2-phenyleth-1-yl-amino | NHBz | NaOCH₃, 1,2-propanediol | CH₃OCH(CH₃)₂ |
| V-67 | (1S)-1-chloroethyl | (1R)-cyclobutyl-2-phenyleth-1-yl-amino | NHBz | NaOCH₃, 1,2-propanediol | CH₃OCH(CH₃)₂ |
| V-68 | 1-fluoro-1-methylethyl | 1-methyl-2-(3,5-dimethylphenyloxy)eth-1-yl-amino | NHBz | NaOCH₃ | CH₃OH |
| V-69 | 1-fluoro-1-methylethyl | (1R)-1-methyl-2-(3,5-dimethylphenyloxy)eth-1-yl-amino | NHBz | NaOCH₃ | C₂H₅OC₂H₄OH |
| V-70 | 1-fluoro-1-methylethyl | (1S)-1-methyl-2-(3,5-dimethylphenyloxy)eth-1-yl-amino | NHBz | NaOCH₃ | CH₃OH |
| V-71 | 1-fluoro-1-methylethyl | 1,1-dicyclopropylmethyl-amino | NHBz | NaOCH₃ | CH₃OH |
| V-72 | 1-fluoro-1-methylethyl | pent-3-ylamino | NHBz | NaOCH₃ | CH₃OH |
| V-73 | 1-fluoro-1-methylethyl | 3,4-dihydro-2H-chromen-4-yl-amino | NHBz | NaOCH₃ | CH₃OH |
| V-74 | 1-fluoro-1-methylethyl | (4R)-3,4-dihydro-2H-chromen-4-yl-amino | NHBz | NaOCH₃ | CH₃OH |
| V-75 | 1-fluoro-1-methylethyl | (4S)-3,4-dihydro-2H-chromen-4-yl-amino | NHBz | NaOCH₃ | CH₃OH |
| V-76 | 1-fluoro-1-methylethyl | (3RS,4RS)-3-methyl-3,4-dihydro-2H-chromen-4-yl-amino | NHBz | NaOCH₃ | CH₃OH |
| V-77 | 1-fluoro-1-methylethyl | (3R,4R)-3-methyl-3,4-dihydro-2H-chromen-4-yl-amino | NHBz | NaOCH₃ | CH₃OH |
| V-78 | 1-fluoro-1-methylethyl | (3S,4S)-3-methyl-3,4-dihydro-2H-chromen-4-yl-amino | NHBz | NaOCH₃ | CH₃OH |
| V-79 | 1-fluoro-1-methylethyl | (1RS)-1-cyclopropylethyl-amino | NHBz | NaOCH₃ | CH₃OH |

TABLE I-continued

Compounds of formula (Va)

(Va)

| Cpd. | Q | NR¹R² | NR³R⁴ | Additive | Solvent |
|---|---|---|---|---|---|
| V-80 | 1-fluoro-1-methylethyl | (1R)-1-cyclopropylethyl-amino | NHBz | NaOCH₃ | CH₃OH |
| V-81 | 1-fluoro-1-methylethyl | (1S)-1-cyclopropylethyl-amino | NHBz | NaOCH₃ | CH₃OH |
| V-82 | 1-fluoro-propyl | (1RS)-1-(4-chlorphenyl)eth-1-yl-amino | NHBz | NaOCH₃ | CH₃OH |
| V-83 | 1-fluoro-propyl | (1R)-1-(4-chlorphenyl)eth-1-yl-amino | NHBz | NaOCH₃ | CH₃OH |
| V-84 | 1-fluoro-propyl | (1S)-1-(4-chlorphenyl)eth-1-yl-amino | NHBz | NaOCH₃ | CH₃OH |
| V-85 | (1S)-1-chloroethyl | (1R)-1,2,3,4-tetrahydro-napht-1-yl-amino | NHBz | — | CH₃OH |
| V-86 | (1S)-1-chloroethyl | (1S)-1,2,3,4-tetrahydro-napht-1-yl-amino | NHBz | — | CH₃OH |
| V-87 | (1R)-1-fluoroethyl | (1R)-1,2,3,4-tetrahydro-napht-1-yl-amino | NHBz | NaOCH₃, 1,2-propanediol | CH₃OH |
| V-88 | (1R)-1-fluoroethyl | (1S)-1,2,3,4-tetrahydro-napht-1-yl-amino | NHBz | NaOCH₃, 1,2-propanediol | CH₃OH |
| V-89 | (1S)-1-chloroethyl | morpholin-yl | NBz₂ | NaOCH₃ | CH₃OH |
| V-90 | (1S)-1-hydroxyethyl | benzylamino | NBz₂ | NaOCH₃ | CH₃OH |
| V-91 | methoxymethyl | cyclohexylamino | NBz₂ | NaOCH₃ | CH₃OH |
| V-92 | (1R)-1-fluoroethyl | (1R)-2,3-dihydro-6-methyl-1H-inden-1yl-amino | NBz₂ | NaOCH₃ | CH₃OH |
| V-93 | (1R)-1-fluoroethyl | 1,2,3,4-tetrahydro-iso-quinolin-2-yl | NBz₂ | NaOCH₃ | CH₃OH |
| V-94 | (1S)-1-chloroethyl | (1RS)-1,2,3,4-tetrahydro-napht-1-yl-amino | NBz₂ | NaOCH₃ | CH₃OH |
| V-95 | (1S)-1-fluoroethyl | 1,2,3,4-tetrahydro-isoquinolin-2-yl | NBz₂ | NaOCH₃ | CH₃OH |
| V-96 | difluoromethyl | (1R,2S)-2,3-dihydro-2,6-dimethyl-1H-inden-1yl-amino | NBz₂ | NaOCH₃ | CH₃OH |
| V-97 | (1S)-1-chloroethyl | (1R,2S)-2,3-dihydro-2,4,6-trimethyl-1H-inden-1yl-amino | NBz₂ | NaOCH₃ | CH₃OH |
| V-98 | (1R)-1-fluoroethyl | (1R,2S)-2,3-dihydro-2,6-dimethyl-1H-inden-1yl-amino | NBz₂ | NaOCH₃ | CH₃OH |
| V-99 | (1S)-1-fluoroethyl | (1R,2S)-2,3-dihydro-2,6-dimethyl-1H-inden-1yl-amino | NBz₂ | NaOCH₃ | CH₃OH |
| V-100 | (1R)-1-fluoroethyl | (1R,2S)-2,3-dihydro-2-methyl-1H-inden-1yl-amino | NBz₂ | NaOCH₃ | CH₃OH |
| V-101 | difluoromethyl | (1R,2S)-2,3-dihydro-2,6-dimethyl-1H-inden-1yl-amino | NBz₂ | NaOCH₃ | CH₃OH |
| V-102 | (1R)-1-fluoroethyl | (1RS)-1,2,3,4-tetrahydro-napht-1-yl-amino | NBz₂ | NaOCH₃ | CH₃OH |
| V-103 | (1R)-1-fluoroethyl | 1,2,3,4-tetrahydro-isoquinolin-2-yl | NBz₂ | NaOCH₃ | CH₃OH |
| V-104 | (1R)-1-fluoroethyl | (1R,2R)-2,3-dihydro-2,6-dimethyl-1H-inden-1yl-amino | NBz₂ | NaOCH₃ | CH₃OH |
| V-105 | difluoromethyl | (1R)-2,3-dihydro-6-methyl-1H-inden-1yl-amino | NBz₂ | NaOCH₃ | CH₃OH |
| V-106 | difluoromethyl | 1,2,3,4-tetrahydro-isoquinolin-2-yl | NBz₂ | NaOCH₃ | CH₃OH |
| V-107 | 1-fluoro-1-methylethyl | (1R)-2,3-dihydro-6-methyl-1H-inden-1yl-amino | NBz₂ | NaOCH₃ | CH₃OH |
| V-108 | 1-fluoro-1-methylethyl | 1-cyclobutyl-2-phenyleth-1-yl-amino | NBz₂ | NaOCH₃ | CH₃OH |
| V-109 | 1-fluoro-1-methylethyl | (1R)-cyclobutyl-2-phenyleth-1-yl-amino | NBz₂ | NaOCH₃ | CH₃OH |
| V-110 | (1R)-1-fluoroethyl | (1R)-cyclobutyl-2-phenyleth-1-yl-amino | NBz₂ | NaOCH₃ | CH₃OH |
| V-111 | (1S)-1-fluoroethyl | (1R)-cyclobutyl-2-phenyleth-1-yl-amino | NBz₂ | NaOCH₃ | CH₃OH |
| V-112 | 1-fluoro-1-methylethyl | 1-methyl-2-(3,5-dimethylphenyloxy)eth-1-yl-amino | NBz₂ | NaOCH₃ | CH₃OH |
| V-113 | 1-fluoro-1-methylethyl | (1R)-1-methyl-2-(3,5-dimethylphenyloxy)eth-1-yl-amino | NBz₂ | NaOCH₃ | CH₃OH |
| V-114 | 1-fluoro-1-methylethyl | (1S)-1-methyl-2-(3,5-dimethylphenyloxy)eth-1-yl-amino | NBz₂ | NaOCH₃ | CH₃OH |
| V-115 | 1-fluoro-1-methylethyl | 1,1-dicyclopropylmethyl-amino | NBz₂ | NaOCH₃ | CH₃OH |
| V-116 | 1-fluoro-1-methylethyl | pent-3-ylamino | NBz₂ | NaOCH₃ | CH₃OH |
| V-117 | 1-fluoro-1-methylethyl | (4RS)-3,4-dihydro-2H-chromen-4-yl-amino | NBz₂ | NaOCH₃ | CH₃OH |
| V-118 | 1-fluoro-1-methylethyl | (4R)-3,4-dihydro-2H-chromen-4-yl-amino | NBz₂ | NaOCH₃ | CH₃OH |
| V-119 | 1-fluoro-1-methylethyl | (4S)-3,4-dihydro-2H-chromen-4-yl-amino | NBz₂ | NaOCH₃ | CH₃OH |
| V-120 | 1-fluoro-1-methylethyl | (3RS,4RS)-3-methyl-3,4-dihydro-2H-chromen-4-yl-amino | NBz₂ | NaOCH₃ | CH₃OH |
| V-121 | 1-fluoro-1-methylethyl | (3R,4R)-3-methyl-3,4-dihydro-2H-chromen-4-yl-amino | NBz₂ | NaOCH₃ | CH₃OH |
| V-122 | 1-fluoro-1-methylethyl | (4S,4S)-3-methyl-3,4-dihydro-2H-chromen-4-yl-amino | NBz₂ | NaOCH₃ | CH₃OH |
| V-123 | 1-fluoro-1-methylethyl | (1RS)-1-cyclopropylethyl-amino | NBz₂ | NaOCH₃ | CH₃OH |
| V-124 | 1-fluoro-1-methylethyl | (1R)-1-cyclopropylethyl-amino | NBz₂ | NaOCH₃ | CH₃OH |
| V-125 | 1-fluoro-1-methylethyl | (1S)-1-cyclopropylethyl-amino | NBz₂ | NaOCH₃ | CH₃OH |
| V-126 | 1-fluoro-propyl | (1RS)-1-(4-chlorphenyl)eth-1-yl-amino | NBz₂ | NaOCH₃ | CH₃OH |
| V-127 | 1-fluoro-propyl | (1R)-1-(4-chlorphenyl)eth-1-yl-amino | NBz₂ | NaOCH₃ | CH₃OH |
| V-128 | 1-fluoro-propyl | (1S)-1-(4-chlorphenyl)eth-1-yl-amino | NBz₂ | NaOCH₃ | CH₃OH |
| V-129 | (1S)-1-chloroethyl | (1R)-1,2,3,4-tetrahydro-napht-1-yl-amino | NBz₂ | — | CH₃OH |
| V-130 | (1S)-1-chloroethyl | (1S)-1,2,3,4-tetrahydro-napht-1-yl-amino | NBz₂ | — | CH₃OH |
| V-131 | (1R)-1-fluoroethyl | (1R)-1,2,3,4-tetrahydro-napht-1-yl-amino | NBz₂ | NaOCH₃, 1,2-propanediol | CH₃OH |
| V-132 | (1R)-1-fluoroethyl | (1S)-1,2,3,4-tetrahydro-napht-1-yl-amino | NBz₂ | NaOCH₃, 1,2-propanediol | CH₃OH |
| V-133 | (1S)-1-chloroethyl | (3S,4R)-3-methyl-3,4-dihydro-2H-chromen-4-yl-amino | NH₂ | — | CH₃OH |
| V-134 | (1S)-1-chloroethyl | (4R,4S)-3-methyl-3,4-dihydro-2H-chromen-4-yl-amino | NH₂ | — | CH₃OH |
| V-135 | (1R)-1-fluoroethyl | (3S,4R)-3-methyl-3,4-dihydro-2H-chromen-4-yl-amino | NH₂ | 1,2-propanediol | CH₃OH |
| V-136 | (1R)-1-fluoroethyl | (4R,4S)-3-methyl-3,4-dihydro-2H-chromen-4-yl-amino | NH₂ | 1,2-propanediol | CH₃OH |
| V-137 | 1-fluoro-1-methylethyl | (3S,4R)-3-methyl-3,4-dihydro-2H-chromen-4-yl-amino | NH₂ | NaOCH₃, 1,2-propanediol | CH₃OCH(CH₃)₂ |
| V-138 | 1-fluoro-1-methylethyl | (4R,4S)-3-methyl-3,4-dihydro-2H-chromen-4-yl-amino | NH₂ | NaOCH₃, 1,2-propanediol | CH₃OCH(CH₃)₂ |

TABLE I-continued

Compounds of formula (Va)

(Va)

| Cpd. | Q | NR$^1$R$^2$ | NR$^3$R$^4$ | Additive | Solvent |
|---|---|---|---|---|---|
| V-139 | difluoromethyl | (3S,4R)-3-methyl-3,4-dihydro-2H-chromen-4-yl-amino | NH$_2$ | NaOCH$_3$ | CH$_3$OH |
| V-140 | difluoromethyl | (4R,4S)-3-methyl-3,4-dihydro-2H-chromen-4-yl-amino | NH$_2$ | NaOCH$_3$ | CH$_3$OH |

Abbreviations in Table I:
Bz = benzyl
NHBz = benzylamino
NBz$_2$ = dibenzylamino
Reaction conditions as to examples in Table I:
1) Reaction temperature of 70 to 75° C. in all experiments used
2) Yield generally in the range of percent 70 to 85 of theory, sometimes less yield when additive has been omitted

TABLE II

Compounds of formula (Ia-1)

(Ia-1)

| Cpd. no. | Y | NR$^1$R$^2$ | NR$^3$R$^4$ | Al-source | Solvent |
|---|---|---|---|---|---|
| (Ia-1.1) | O-i-Pr | morpholin-yl | NH$_2$ | Al(O-i-Pr)$_3$ | (CH$_3$)$_2$CHOH |
| (Ia-1.2) | O-i-Pr | benzylamino | NH$_2$ | Al(O-i-Pr)$_3$ | (CH$_3$)$_2$CHOH |
| (Ia-1.3) | O-i-Pr | cyclohexylamino | NH$_2$ | Al(O-i-Pr)$_3$ | (CH$_3$)$_2$CHOH |
| (Ia-1.4) | O-i-Pr | (1RS)-2,3-dihydro-6-methyl-1H-inden-1yl-amino | NH$_2$ | Al(O-i-Pr)$_3$ | (CH$_3$)$_2$CHOH |
| (Ia-1.5) | O-i-Pr | (1R)-2,3-dihydro-6-methyl-1H-inden-1yl-amino | NH$_2$ | Al(O-i-Pr)$_3$ | (CH$_3$)$_2$CHOH |
| (Ia-1.6) | O-i-Pr | (1S)-2,3-dihydro-6-methyl-1H-inden-1yl-amino | NH$_2$ | Al(O-i-Pr)$_3$ | (CH$_3$)$_2$CHOH |
| (Ia-1.7) | O-i-Pr | 1,2,3,4-tetrahydro-quinolin-1-yl | NH$_2$ | Al(O-i-Pr)$_3$ | (CH$_3$)$_2$CHOH |
| (Ia-1.8) | O-i-Pr | 1,2,3,4-tetrahydro-isoquinolin-2-yl | NH$_2$ | Al(O-i-Pr)$_3$ | (CH$_3$)$_2$CHOH |
| (Ia-1.9) | O-i-Pr | (1RS)-1,2,3,4-tetrahydro-napht-1-yl-amino | NH$_2$ | Al(O-i-Pr)$_3$ | (CH$_3$)$_2$CHOH |
| (Ia-1.10) | O-i-Pr | (1R)-1,2,3,4-tetrahydro-napht-1-yl-amino | NH$_2$ | Al(O-i-Pr)$_3$ | (CH$_3$)$_2$CHOH |
| (Ia-1.11) | O-i-Pr | (1S)-1,2,3,4-tetrahydro-napht-1-yl-amino | NH$_2$ | Al(O-i-Pr)$_3$ | (CH$_3$)$_2$CHOH |
| (Ia-1.12) | O-i-Pr | (1R,2S)-2,3-dihydro-2,6-dimethyl-1H-inden-1yl-amino | NH$_2$ | Al(O-i-Pr)$_3$ | (CH$_3$)$_2$CHOH |
| (Ia-1.13) | O-i-Pr | (1S,2R)-2,3-dihydro-2,4,6-trimethyl-1H-inden-1yl-amino | NH$_2$ | Al(O-i-Pr)$_3$ | (CH$_3$)$_2$CHOH |
| (Ia-1.14) | O-i-Pr | (1R,2R)-2,3-dihydro-2,6-dimethyl-1H-inden-1yl-amino | NH$_2$ | Al(CH$_3$)$_3$ | (CH$_3$)$_2$CHOH |
| (Ia-1.15) | O-i-Pr | (1S,2S)-2,3-dihydro-2,6-dimethyl-1H-inden-1yl-amino | NH$_2$ | Al(CH$_3$)$_3$ | (CH$_3$)$_2$CHOH |
| (Ia-1.16) | O-i-Pr | (1R,2S)-2,3-dihydro-2-methyl-1H-inden-1yl-amino | NH$_2$ | Al(O-i-Pr)$_3$ | (CH$_3$)$_2$CHOH |
| (Ia-1.17) | O-i-Pr | (1R,2R)-2,3-dihydro-2-methyl-1H-inden-1yl-amino | NH$_2$ | Al(O-i-Pr)$_3$ | (CH$_3$)$_2$CHOH |
| (Ia-1.18) | O-i-Pr | (1R,2S)-2,3-dihydro-2,4,6-trimethyl-1H-inden-1yl-amino | NH$_2$ | Al(O-i-Pr)$_3$ | (CH$_3$)$_2$CHOH |
| (Ia-1.19) | O-i-Pr | (1S,2R)-2,3-dihydro-2,6-methyl-1H-inden-1yl-amino | NH$_2$ | Al(O-i-Pr)$_3$ | (CH$_3$)$_2$CHOH |
| (Ia-1.20) | O-i-Pr | (3RS,4RS)-3-methyl-3,4-dihydro-2H-chromen-4-yl-amino | NH$_2$ | Al(O-i-Pr)$_3$ | (CH$_3$)$_2$CHOH |
| (Ia-1.21) | O-i-Pr | (3R,4R)-3-methyl-3,4-dihydro-2H-chromen-4-yl-amino | NH$_2$ | Al(O-i-Pr)$_3$ | (CH$_3$)$_2$CHOH |
| (Ia-1.22) | O-i-Pr | (3S,4S)-3-methyl-3,4-dihydro-2H-chromen-4-yl-amino | NH$_2$ | Al(O-i-Pr)$_3$ | (CH$_3$)$_2$CHOH |
| (Ia-1.23) | O-i-Pr | (1RS)-1-cyclopropylethyl-amino | NH$_2$ | Al(O-i-Pr)$_3$ | (CH$_3$)$_2$CHOH |
| (Ia-1.24) | O-i-Pr | (1R)-cyclopropylethyl-amino | NH$_2$ | Al(O-i-Pr)$_3$ | (CH$_3$)$_2$CHOH |
| (Ia-1.25) | O-i-Pr | (1S)-cyclopropylethyl-amino | NH$_2$ | Al(O-i-Pr)$_3$ | (CH$_3$)$_2$CHOH |
| (Ia-1.26) | O-i-Pr | (1RS)-1-(4-chlorphenyl)eth-1-yl-amino | NH$_2$ | Al(O-i-Pr)$_3$ | (CH$_3$)$_2$CHOH |
| (Ia-1.27) | O-i-Pr | (1R)-(4-chlorphenyl)eth-1-yl-amino | NH$_2$ | Al(O-i-Pr)$_3$ | (CH$_3$)$_2$CHOH |
| (Ia-1.28) | O-i-Pr | (1S)-(4-chlorphenyl)eth-1-yl-amino | NH$_2$ | Al(O-i-Pr)$_3$ | (CH$_3$)$_2$CHOH |
| (Ia-1.29) | O-i-Pr | (1RS)-1-methyl-2-(3,5-dimethylphenyloxy)eth-1-yl-amino | NH$_2$ | Al(O-i-Pr)$_3$ | (CH$_3$)$_2$CHOH |
| (Ia-1.30) | O-i-Pr | (1R)-1-methyl-2-(3,5-dimethylphenyloxy)eth-1-yl-amino | NH$_2$ | Al(O-i-Pr)$_3$ | (CH$_3$)$_2$CHOH |
| (Ia-1.31) | O-i-Pr | (1S)-1-methyl-2-(3,5-dimethylphenyloxy)eth-1-yl-amino | NH$_2$ | Al(O-i-Pr)$_3$ | (CH$_3$)$_2$CHOH |
| (Ia-1.32) | O-i-Pr | 1,1-dicyclopropylmethyl-amino | NH$_2$ | Al(O-i-Pr)$_3$ | (CH$_3$)$_2$CHOH |
| (Ia-1.33) | O-i-Pr | pent-3-ylamino | NH$_2$ | Al(O-i-Pr)$_3$ | (CH$_3$)$_2$CHOH |
| (Ia-1.34) | O-i-Pr | (1RS)-1-cyclobutyl-2-phenyleth-1-yl-amino | NH$_2$ | Al(O-i-Pr)$_3$ | (CH$_3$)$_2$CHOH |
| (Ia-1.35) | O-i-Pr | (1R)-cyclobutyl-2-phenyleth-1-yl-amino | NH$_2$ | Al(O-i-Pr)$_3$ | (CH$_3$)$_2$CHOH |

TABLE II-continued

Compounds of formula (Ia-1)

(Ia-1)

| Cpd. no. | Y | NR$^1$R$^2$ | NR$^3$R$^4$ | Al-source | Solvent |
|---|---|---|---|---|---|
| (Ia-1.36) | O-i-Pr | (1S)-cyclobutyl-2-phenyleth-l-yl-amino | NH$_2$ | Al(O-i-Pr)$_3$ | (CH$_3$)$_2$CHOH |
| (Ia-1.37) | —OCH(CH$_3$)CH$_2$OCH$_3$ | morpholin-yl | NHBz | Al(O-i-Pr)$_3$ | HOCH(CH$_3$)CH$_2$OCH$_3$ |
| (Ia-1.38) | —OCH(CH$_3$)CH$_2$OCH$_3$ | benzylamino | NHBz | Al(O-i-Pr)$_3$ | HOCH(CH$_3$)CH$_2$OCH$_3$ |
| (Ia-1.39) | —OCH(CH$_3$)CH$_2$OCH$_3$ | cyclohexylamino | NHBz | Al(O-i-Pr)$_3$ | HOCH(CH$_3$)CH$_2$OCH$_3$ |
| (Ia-1.40) | —OCH(CH$_3$)CH$_2$OCH$_3$ | 2,3-dihydro-6-methyl-1H-inden-1yl-amino | NHBz | Al(O-i-Pr)$_3$ | HOCH(CH$_3$)CH$_2$OCH$_3$ |
| (Ia-1.41) | —OCH(CH$_3$)CH$_2$OCH$_3$ | (1R)-2,3-dihydro-6-methyl-1H-inden-1yl-amino | NHBz | Al(O-i-Pr)$_3$ | HOCH(CH$_3$)CH$_2$OCH$_3$ |
| (Ia-1.42) | —OCH(CH$_3$)CH$_2$OCH$_3$ | (1S)-2,3-dihydro-6-methyl-1H-inden-1yl-amino | NHBz | Al(O-i-Pr)$_3$ | HOCH(CH$_3$)CH$_2$OCH$_3$ |
| (Ia-1.43) | —OCH(CH$_3$)CH$_2$OCH$_3$ | 1,2,3,4-tetrahydro-quinolin-1-yl | NHBz | Al(O-i-Pr)$_3$ | HOCH(CH$_3$)CH$_2$OCH$_3$ |
| (Ia-1.44) | —OCH(CH$_3$)CH$_2$OCH$_3$ | 1,2,3,4-tetrahydro-isoquinolin-2-yl | NHBz | Al(O-i-Pr)$_3$ | HOCH(CH$_3$)CH$_2$OCH$_3$ |
| (Ia-1.45) | —OCH(CH$_3$)CH$_2$OCH$_3$ | 1,2,3,4-tetrahydro-napht-1-yl-amino | NHBz | Al(O-i-Pr)$_3$ | HOCH(CH$_3$)CH$_2$OCH$_3$ |
| (Ia-1.46) | —OCH(CH$_3$)CH$_2$OCH$_3$ | (1R)-1,2,3,4-tetrahydro-napht-l-yl-amino | NHBz | Al(O-i-Pr)$_3$ | HOCH(CH$_3$)CH$_2$OCH$_3$ |
| (Ia-1.47) | —OCH(CH$_3$)CH$_2$OCH$_3$ | (1S)-1,2,3,4-tetrahydro-napht-1-yl-amino | NHBz | Al(O-i-Pr)$_3$ | HOCH(CH$_3$)CH$_2$OCH$_3$ |
| (Ia-1.48) | —OCH(CH$_3$)CH$_2$OCH$_3$ | (1R,2S)-2,3-dihydro-2,6-dimethyl-1H-inden-1yl-amino | NHBz | Al(O-i-Pr)$_3$ | HOCH(CH$_3$)CH$_2$OCH$_3$ |
| (Ia-1.49) | —OCH(CH$_3$)CH$_2$OCH$_3$ | (1S,2R)-2,3-dihydro-2,4,6-trimethyl-1H-inden-1yl-amino | NHBz | Al(O-i-Pr)$_3$ | HOCH(CH$_3$)CH$_2$OCH$_3$ |
| (Ia-1.50) | —OCH(CH$_3$)CH$_2$OCH$_3$ | (1R,2R)-2,3-dihydro-2,6-dimethyl-1H-inden-1yl-amino | NHBz | Al(O-i-Pr)$_3$ | HOCH(CH$_3$)CH$_2$OCH$_3$ |
| (Ia-1.51) | —OCH(CH$_3$)CH$_2$OCH$_3$ | (1S,2S)-2,3-dihydro-2,6-dimethyl-1H-inden-1yl-amino | NHBz | Al(O-i-Pr)$_3$ | HOCH(CH$_3$)CH$_2$OCH$_3$ |
| (Ia-1.52) | —OCH(CH$_3$)CH$_2$OCH$_3$ | (1R,2S)-2,3-dihydro-2-methyl-1H-inden-1yl-amino | NHBz | Al(O-i-Pr)$_3$ | HOCH(CH$_3$)CH$_2$OCH$_3$ |
| (Ia-1.53) | —OCH(CH$_3$)CH$_2$OCH$_3$ | (1R,2R)-2,3-dihydro-2-methyl-1H-inden-1yl-amino | NHBz | Al(O-i-Pr)$_3$ | HOCH(CH$_3$)CH$_2$OCH$_3$ |
| (Ia-1.54) | —OCH(CH$_3$)CH$_2$OCH$_3$ | (1R,2S)-2,3-dihydro-2,4,6-trimethyl-1H-inden-1yl-amino | NHBz | Al(O-i-Pr)$_3$ | HOCH(CH$_3$)CH$_2$OCH$_3$ |
| (Ia-1.55) | —OCH(CH$_3$)CH$_2$OCH$_3$ | (1S,2R)-2,3-dihydro-2,6-methyl-1H-inden-1yl-amino | NHBz | Al(O-i-Pr)$_3$ | HOCH(CH$_3$)CH$_2$OCH$_3$ |
| (Ia-1.56) | —OCH(CH$_3$)CH$_2$OCH$_3$ | (3RS,4RS)-3-methyl-3,4-dihydro-2H-chromen-4-yl-amino | NHBz | Al(O-i-Pr)$_3$ | HOCH(CH$_3$)CH$_2$OCH$_3$ |
| (Ia-1.57) | —OCH(CH$_3$)CH$_2$OCH$_3$ | (3R,4R)-3-methyl-3,4-dihydro-2H-chromen-4-yl-amino | NHBz | Al(O-i-Pr)$_3$ | HOCH(CH$_3$)CH$_2$OCH$_3$ |
| (Ia-1.58) | —OCH(CH$_3$)CH$_2$OCH$_3$ | (3S,4S)-3-methyl-3,4-dihydro-2H-chromen-4-yl-amino | NHBz | Al(O-i-Pr)$_3$ | HOCH(CH$_3$)CH$_2$OCH$_3$ |
| (Ia-1.59) | —OCH(CH$_3$)CH$_2$OCH$_3$ | 1-cyclopropylethyl-amino | NHBz | Al(O-i-Pr)$_3$ | HOCH(CH$_3$)CH$_2$OCH$_3$ |
| (Ia-1.60) | —OCH(CH$_3$)CH$_2$OCH$_3$ | (1R)-cyclopropylethyl-amino | NHBz | Al(O-i-Pr)$_3$ | HOCH(CH$_3$)CH$_2$OCH$_3$ |
| (Ia-1.61) | —OCH(CH$_3$)CH$_2$OCH$_3$ | (1S)-cyclopropylethyl-amino | NHBz | Al(O-i-Pr)$_3$ | HOCH(CH$_3$)CH$_2$OCH$_3$ |
| (Ia-1.62) | —OCH(CH$_3$)CH$_2$OCH$_3$ | 1-(4-chlorphenyl)eth-1-yl-amino | NHBz | Al(O-i-Pr)$_3$ | HOCH(CH$_3$)CH$_2$OCH$_3$ |
| (Ia-1.63) | —OCH(CH$_3$)CH$_2$OCH$_3$ | (1R)-(4-chlorphenyl)eth-1-yl-amino | NHBz | Al(O-i-Pr)$_3$ | HOCH(CH$_3$)CH$_2$OCH$_3$ |
| (Ia-1.64) | —OCH(CH$_3$)CH$_2$OCH$_3$ | (1S)-(4-chlorphenyl)eth-1-yl-amino | NHBz | Al(O-i-Pr)$_3$ | HOCH(CH$_3$)CH$_2$OCH$_3$ |
| (Ia-1.65) | —OCH(CH$_3$)CH$_2$OCH$_3$ | 1-methyl-2-(3,5-dimethylphenyloxy)eth-1-yl-amino | NHBz | Al(O-i-Pr)$_3$ | HOCH(CH$_3$)CH$_2$OCH$_3$ |
| (Ia-1.66) | —OCH(CH$_3$)CH$_2$OCH$_3$ | (1R)-1-methyl-2-(3,5-dimethylphenyloxy)eth-1-yl-amino | NHBz | Al(O-i-Pr)$_3$ | HOCH(CH$_3$)CH$_2$OCH$_3$ |
| (Ia-1.67) | —OCH(CH$_3$)CH$_2$OCH$_3$ | (1S)-1-methyl-2-(3,5-dimethylphenyloxy)eth-1-yl-amino | NHBz | Al(O-i-Pr)$_3$ | HOCH(CH$_3$)CH$_2$OCH$_3$ |
| (Ia-1.68) | —OCH(CH$_3$)CH$_2$OCH$_3$ | 1,1-dicyclopropylmethyl-amino | NHBz | Al(O-i-Pr)$_3$ | HOCH(CH$_3$)CH$_2$OCH$_3$ |
| (Ia-1.69) | —OCH(CH$_3$)CH$_2$OCH$_3$ | pent-3-ylamino | NHBz | Al(O-i-Pr)$_3$ | HOCH(CH$_3$)CH$_2$OCH$_3$ |
| (Ia-1.70) | —OCH(CH$_3$)CH$_2$OCH$_3$ | 1-cyclobutyl-2-phenyleth-1-yl-amino | NHBz | Al(O-i-Pr)$_3$ | HOCH(CH$_3$)CH$_2$OCH$_3$ |
| (Ia-1.71) | —OCH(CH$_3$)CH$_2$OCH$_3$ | (1R)-cyclobutyl-2-phenyleth-1-yl-amino | NHBz | Al(O-i-Pr)$_3$ | HOCH(CH$_3$)CH$_2$OCH$_3$ |
| (Ia-1.72) | —OCH(CH$_3$)CH$_2$OCH$_3$ | (1S)-cyclobutyl-2-phenyleth-1-yl-amino | NHBz | Al(O-i-Pr)$_3$ | HOCH(CH$_3$)CH$_2$OCH$_3$ |
| (Ia-1.73) | —OCH$_2$CH$_2$OC$_2$H$_5$ | morpholin-yl | NBz$_2$ | Al(O-i-Pr)$_3$ | HOCH$_2$CH$_2$OC$_2$H$_5$ |
| (Ia-1.74) | —OCH$_2$CH$_2$OC$_2$H$_5$ | benzylamino | NBz$_2$ | Al(O-i-Pr)$_3$ | HOCH$_2$CH$_2$OC$_2$H$_5$ |
| (Ia-1.75) | —OCH$_2$CH$_2$OC$_2$H$_5$ | cyclohexylamino | NBz$_2$ | Al(O-i-Pr)$_3$ | HOCH$_2$CH$_2$OC$_2$H$_5$ |
| (Ia-1.76) | —OCH$_2$CH$_2$OC$_2$H$_5$ | 2,3-dihydro-6-methyl-1H-inden-1yl-amino | NBz$_2$ | Al(O-i-Pr)$_3$ | HOCH$_2$CH$_2$OC$_2$H$_5$ |
| (Ia-1.77) | —OCH$_2$CH$_2$OC$_2$H$_5$ | (1R)-2,3-dihydro-6-methyl-1H-inden-1yl-amino | NBz$_2$ | Al(O-i-Pr)$_3$ | HOCH$_2$CH$_2$OC$_2$H$_5$ |
| (Ia-1.78) | —OCH$_2$CH$_2$OC$_2$H$_5$ | (1S)-2,3-dihydro-6-methyl-1H-inden-1yl-amino | NBz$_2$ | Al(O-i-Pr)$_3$ | HOCH$_2$CH$_2$OC$_2$H$_5$ |
| (Ia-1.79) | —OCH$_2$CH$_2$OC$_2$H$_5$ | 1,2,3,4-tetrahydro-quinolin-1-yl | NBz$_2$ | Al(O-i-Pr)$_3$ | HOCH$_2$CH$_2$OC$_2$H$_5$ |
| (Ia-1.80) | —OCH$_2$CH$_2$OC$_2$H$_5$ | 1,2,3,4-tetrahydro-iso-quinolin-2-yl | NBz$_2$ | Al(O-i-Pr)$_3$ | HOCH$_2$CH$_2$OC$_2$H$_5$ |
| (Ia-1.81) | —OCH$_2$CH$_2$OC$_2$H$_5$ | 1,2,3,4-tetrahydro-napht-l-yl-amino | NBz$_2$ | Al(O-i-Pr)$_3$ | HOCH$_2$CH$_2$OC$_2$H$_5$ |
| (Ia-1.82) | —OCH$_2$CH$_2$OC$_2$H$_5$ | (1R)-1,2,3,4-tetrahydro-napht-1-yl-amino | NBz$_2$ | Al(O-i-Pr)$_3$ | HOCH$_2$CH$_2$OC$_2$H$_5$ |
| (Ia-1.83) | —OCH$_2$CH$_2$OC$_2$H$_5$ | (1S)-1,2,3,4-tetrahydro-napht-1-yl-amino | NBz$_2$ | Al(O-i-Pr)$_3$ | HOCH$_2$CH$_2$OC$_2$H$_5$ |
| (Ia-1.84) | —OCH$_2$CH$_2$OC$_2$H$_5$ | (1R,2S)-2,3-dihydro-2,6-dimethyl-1H-inden-1yl-amino | NBz$_2$ | Al(O-i-Pr)$_3$ | HOCH$_2$CH$_2$OC$_2$H$_5$ |
| (Ia-1.85) | —OCH$_2$CH$_2$OC$_2$H$_5$ | (1S,2R)-2,3-dihydro-2,4,6-trimethyl-1H-inden-1yl-amino | NBz$_2$ | Al(O-i-Pr)$_3$ | HOCH$_2$CH$_2$OC$_2$H$_5$ |
| (Ia-1.86) | —OCH$_2$CH$_2$OC$_2$H$_5$ | (1R,2R)-2,3-dihydro-2,6-dimethyl-1H-inden-1yl-amino | NBz$_2$ | Al(O-i-Pr)$_3$ | HOCH$_2$CH$_2$OC$_2$H$_5$ |
| (Ia-1.87) | —OCH$_2$CH$_2$OC$_2$H$_5$ | (1S,2S)-2,3-dihydro-2,6-dimethyl-1H-inden-1yl-amino | NBz$_2$ | Al(O-i-Pr)$_3$ | HOCH$_2$CH$_2$OC$_2$H$_5$ |
| (Ia-1.88) | —OCH$_2$CH$_2$OC$_2$H$_5$ | (1R,2S)-2,3-dihydro-2-methyl-1H-inden-1yl-amino | NBz$_2$ | Al(O-i-Pr)$_3$ | HOCH$_2$CH$_2$OC$_2$H$_5$ |
| (Ia-1.89) | —OCH$_2$CH$_2$OC$_2$H$_5$ | (1R,2R)-2,3-dihydro-2-methyl-1H-inden-1yl-amino | NBz$_2$ | Al(O-i-Pr)$_3$ | HOCH$_2$CH$_2$OC$_2$H$_5$ |
| (Ia-1.90) | —OCH$_2$CH$_2$OC$_2$H$_5$ | (1R,2S)-2,3-dihydro-2,4,6-trimethyl-1H-inden-1yl-amino | NBz$_2$ | Al(O-i-Pr)$_3$ | HOCH$_2$CH$_2$OC$_2$H$_5$ |
| (Ia-1.91) | —OCH$_2$CH$_2$OC$_2$H$_5$ | (1S,2R)-2,3-dihydro-2,6-methyl-1H-inden-1yl-amino | NBz$_2$ | Al(O-i-Pr)$_3$ | HOCH$_2$CH$_2$OC$_2$H$_5$ |
| (Ia-1.92) | —OCH$_2$CH$_2$OC$_2$H$_5$ | (3RS,4RS)-3-methyl-3,4-dihydro-2H-chromen-4-yl-amino | NBz$_2$ | Al(O-i-Pr)$_3$ | HOCH$_2$CH$_2$OC$_2$H$_5$ |
| (Ia-1.93) | —OCH$_2$CH$_2$OC$_2$H$_5$ | (3R,4R)-3-methyl-3,4-dihydro-2H-chromen-4-yl-amino | NBz$_2$ | Al(O-i-Pr)$_3$ | HOCH$_2$CH$_2$OC$_2$H$_5$ |
| (Ia-1.94) | —OCH$_2$CH$_2$OC$_2$H$_5$ | (3S,4S)-3-methyl-3,4-dihydro-2H-chromen-4-yl-amino | NBz$_2$ | Al(O-i-Pr)$_3$ | HOCH$_2$CH$_2$OC$_2$H$_5$ |
| (Ia-1.95) | —OCH$_2$CH$_2$OC$_2$H$_5$ | 1-cyclopropylethyl-amino | NBz$_2$ | Al(O-i-Pr)$_3$ | HOCH$_2$CH$_2$OC$_2$H$_5$ |
| (Ia-1.96) | —OCH$_2$CH$_2$OC$_2$H$_5$ | (1R)-cyclopropylethyl-amino | NBz$_2$ | Al(O-i-Pr)$_3$ | HOCH$_2$CH$_2$OC$_2$H$_5$ |
| (Ia-1.97) | —OCH$_2$CH$_2$OC$_2$H$_5$ | (1S)-cyclopropylethyl-amino | NBz$_2$ | Al(O-i-Pr)$_3$ | HOCH$_2$CH$_2$OC$_2$H$_5$ |
| (Ia-1.98) | —OCH$_2$CH$_2$OC$_2$H$_5$ | 1-(4-chlorphenyl)eth-1-yl-amino | NBz$_2$ | Al(O-i-Pr)$_3$ | HOCH$_2$CH$_2$OC$_2$H$_5$ |
| (Ia-1.99) | —OCH$_2$CH$_2$OC$_2$H$_5$ | (1R)-(4-chlorphenyl)eth-1-yl-amino | NBz$_2$ | Al(O-i-Pr)$_3$ | HOCH$_2$CH$_2$OC$_2$H$_5$ |
| (Ia-1.100) | —OCH$_2$CH$_2$OC$_2$H$_5$ | (1S)-(4-chlorphenyl)eth-1-yl-amino | NBz$_2$ | Al(O-i-Pr)$_3$ | HOCH$_2$CH$_2$OC$_2$H$_5$ |

TABLE II-continued

Compounds of formula (Ia-1)

(Ia-1)

$$\begin{array}{c} Y \\ | \\ Al \\ \diagup \quad \diagdown \\ N \quad \quad N \\ | \quad \quad | \quad H \\ R^2-N-C \quad C-N-R^4 \\ | \quad \quad N \quad | \\ R^1 \quad \quad \quad R^3 \end{array}$$

| Cpd. no. | Y | $NR^1R^2$ | $NR^3R^4$ | Al-source | Solvent |
|---|---|---|---|---|---|
| (Ia-1.101) | —OCH$_2$CH$_2$OC$_2$H$_5$ | 1-methyl-2-(3,5-dimethylphenyloxy)eth-1-yl-amino | NBz$_2$ | Al(O-i-Pr)$_3$ | HOCH$_2$CH$_2$OC$_2$H$_5$ |
| (Ia-1.102) | —OCH$_2$CH$_2$OC$_2$H$_5$ | (1R)-1-methyl-2-(3,5-dimethylphenylont)eth-1-yl-amino | NBz$_2$ | Al(O-i-Pr)$_3$ | HOCH$_2$CH$_2$OC$_2$H$_5$ |
| (Ia-1.103) | —OCH$_2$CH$_2$OC$_2$H$_5$ | (1S)-1-methyl-2-(3,5-dimethylphenyloxy)eth-1-yl-amino | NBz$_2$ | Al(O-i-Pr)$_3$ | HOCH$_2$CH$_2$OC$_2$H$_5$ |
| (Ia-1.104) | —OCH$_2$CH$_2$OC$_2$H$_5$ | 1,1-dicyclopropylmethyl-amino | NBz$_2$ | Al(O-i-Pr)$_3$ | HOCH$_2$CH$_2$OC$_2$H$_5$ |
| (Ia-1.105) | —OCH$_2$CH$_2$OC$_2$H$_5$ | pent-3-ylamino | NBz$_2$ | Al(O-i-Pr)$_3$ | HOCH$_2$CH$_2$OC$_2$H$_5$ |
| (Ia-1.106) | —OCH$_2$CH$_2$OC$_2$H$_5$ | 1-cyclobutyl-2-phenyleth-1-yl-amino | NBz$_2$ | Al(O-i-Pr)$_3$ | HOCH$_2$CH$_2$OC$_2$H$_5$ |
| (Ia-1.107) | —OCH$_2$CH$_2$OC$_2$H$_5$ | (1R)-cyclobutyl-2-phenyleth-1-yl-amino | NBz$_2$ | Al(O-i-Pr)$_3$ | HOCH$_2$CH$_2$OC$_2$H$_5$ |
| (Ia-1.108) | —OCH$_2$CH$_2$OC$_2$H$_5$ | (1S)-cyclobutyl-2-phenyleth-1-yl-amino | NBz$_2$ | Al(O-i-Pr)$_3$ | HOCH$_2$CH$_2$OC$_2$H$_5$ |
| (Ia-1.109) | —OCH(CH$_3$)C$_2$H$_5$ | morpholin-yl | NH$_2$ | Al(O-i-Bu)$_3$ | HOCH(CH$_3$)C$_2$H$_5$ |
| (Ia-1.110) | —OCH(CH$_3$)C$_2$H$_5$ | benzylamino | NH$_2$ | Al(O-i-Bu)$_3$ | HOCH(CH$_3$)C$_2$H$_5$ |
| (Ia-1.111) | —OCH(CH$_3$)C$_2$H$_5$ | cyclohexylamino | NH$_2$ | Al(O-i-Bu)$_3$ | HOCH(CH$_3$)C$_2$H$_5$ |
| (Ia-1.112) | —OCH(CH$_3$)C$_2$H$_5$ | 2,3-dihydro-6-methyl-1H-inden-1yl-amino | NH$_2$ | Al(O-i-Bu)$_3$ | HOCH(CH$_3$)C$_2$H$_5$ |
| (Ia-1.113) | —OCH(CH$_3$)C$_2$H$_5$ | (1R)-2,3-dihydro-6-methyl-1H-inden-1yl-amino | NH$_2$ | Al(O-i-Bu)$_3$ | HOCH(CH$_3$)C$_2$H$_5$ |
| (Ia-1.114) | —OCH(CH$_3$)C$_2$H$_5$ | (1S)-2,3-dihydro-6-methyl-1H-inden-1yl-amino | NH$_2$ | Al(O-i-Bu)$_3$ | HOCH(CH$_3$)C$_2$H$_5$ |
| (Ia-1.115) | —OCH(CH$_3$)C$_2$H$_5$ | 1,2,3,4-tetrahydro-quinolin-1-yl | NH$_2$ | Al(O-i-Bu)$_3$ | HOCH(CH$_3$)C$_2$H$_5$ |
| (Ia-1.116) | —OCH(CH$_3$)C$_2$H$_5$ | 1,2,3,4-tetrahydro-isoquinolin-2-yl | NH$_2$ | Al(O-i-Bu)$_3$ | HOCH(CH$_3$)C$_2$H$_5$ |
| (Ia-1.117) | —OCH(CH$_3$)C$_2$H$_5$ | 1,2,3,4-tetrahydro-napht-1-yl-amino | NH$_2$ | Al(O-i-Bu)$_3$ | HOCH(CH$_3$)C$_2$H$_5$ |
| (Ia-1.118) | —OCH(CH$_3$)C$_2$H$_5$ | (1R)-1,2,3,4-tetrahydro-napht-1-yl-amino | NH$_2$ | Al(O-i-Bu)$_3$ | HOCH(CH$_3$)C$_2$H$_5$ |
| (Ia-1.119) | —OCH(CH$_3$)C$_2$H$_5$ | (1S)-1,2,3,4-tetrahydro-napht-1-yl-amino | NH$_2$ | Al(O-i-Bu)$_3$ | HOCH(CH$_3$)C$_2$H$_5$ |
| (Ia-1.120) | —OCH(CH$_3$)C$_2$H$_5$ | (1R,2S)-2,3-dihydro-2,6-dimethyl-1H-inden-1yl-amino | NH$_2$ | Al(O-i-Bu)$_3$ | HOCH(CH$_3$)C$_2$H$_5$ |
| (Ia-1.121) | —OCH(CH$_3$)C$_2$H$_5$ | (1S,2R)-2,3-dihydro-2,4,6-trimethyl-1H-inden-1yl-amino | NH$_2$ | Al(O-i-Bu)$_3$ | HOCH(CH$_3$)C$_2$H$_5$ |
| (Ia-1.122) | —OCH(CH$_3$)C$_2$H$_5$ | (1R,2R)-2,3-dihydro-2,6-dimethyl-1H-inden-1yl-amino | NH$_2$ | Al(O-i-Bu)$_3$ | HOCH(CH$_3$)C$_2$H$_5$ |
| (Ia-1.123) | —OCH(CH$_3$)C$_2$H$_5$ | (1S,2S)-2,3-dihydro-2,6-dimethyl-1H-inden-1yl-amino | NH$_2$ | Al(O-i-Bu)$_3$ | HOCH(CH$_3$)C$_2$H$_5$ |
| (Ia-1.124) | —OCH(CH$_3$)C$_2$H$_5$ | (1R,2S)-2,3-dihydro-2-methyl-1H-inden-1yl-amino | NH$_2$ | Al(O-i-Bu)$_3$ | HOCH(CH$_3$)C$_2$H$_5$ |
| (Ia-1.125) | —OCH(CH$_3$)C$_2$H$_5$ | (1R,2R)-2,3-dihydro-2-methyl-1H-inden-1yl-amino | NH$_2$ | Al(O-i-Bu)$_3$ | HOCH(CH$_3$)C$_2$H$_5$ |
| (Ia-1.126) | —OCH(CH$_3$)C$_2$H$_5$ | (1R,2S)-2,3-dihydro-2,4,6-trimethyl-1H-inden-1yl-amino | NH$_2$ | Al(O-i-Bu)$_3$ | HOCH(CH$_3$)C$_2$H$_5$ |
| (Ia-1.127) | —OCH(CH$_3$)C$_2$H$_5$ | (1S,2R)-2,3-dihydro-2,6-methyl-1H-inden-1yl-amino | NH$_2$ | Al(O-i-Bu)$_3$ | HOCH(CH$_3$)C$_2$H$_5$ |
| (Ia-1.128) | —OCH(CH$_3$)C$_2$H$_5$ | (3RS,4RS)-3-methyl-3,4-dihydro-2H-chromen-4-yl-amino | NH$_2$ | Al(O-i-Bu)$_3$ | HOCH(CH$_3$)C$_2$H$_5$ |
| (Ia-1.129) | —OCH(CH$_3$)C$_2$H$_5$ | (3R,4R)-3-methyl-3,4-dihydro-2H-chromen-4-yl-amino | NH$_2$ | Al(O-i-Bu)$_3$ | HOCH(CH$_3$)C$_2$H$_5$ |
| (Ia-1.130) | —OCH(CH$_3$)C$_2$H$_5$ | (3S,4S)-3-methyl-3,4-dihydro-2H-chromen-4-yl-amino | NH$_2$ | Al(O-i-Bu)$_3$ | HOCH(CH$_3$)C$_2$H$_5$ |
| (Ia-1.131) | —OCH(CH$_3$)C$_2$H$_5$ | 1-cyclopropylethyl-amino | NH$_2$ | Al(O-i-Bu)$_3$ | HOCH(CH$_3$)C$_2$H$_5$ |
| (Ia-1.132) | —OCH(CH$_3$)C$_2$H$_5$ | (1R)-cyclopropylethyl-amino | NH$_2$ | Al(O-i-Bu)$_3$ | HOCH(CH$_3$)C$_2$H$_5$ |
| (Ia-1.133) | —OCH(CH$_3$)C$_2$H$_5$ | (1S)-cyclopropylethyl-amino | NH$_2$ | Al(O-i-Bu)$_3$ | HOCH(CH$_3$)C$_2$H$_5$ |
| (Ia-1.134) | —OCH(CH$_3$)C$_2$H$_5$ | 1-(4-chlorphenyl)eth-1-yl-amino | NH$_2$ | Al(O-i-Bu)$_3$ | HOCH(CH$_3$)C$_2$H$_5$ |
| (Ia-1.135) | —OCH(CH$_3$)C$_2$H$_5$ | (1R)-(4-chlorphenyl)eth-1-yl-amino | NH$_2$ | Al(O-i-Bu)$_3$ | HOCH(CH$_3$)C$_2$H$_5$ |
| (Ia-1.136) | —OCH(CH$_3$)C$_2$H$_5$ | (1S)-(4-chlorphenyl)eth-1-yl-amino | NH$_2$ | Al(O-i-Bu)$_3$ | HOCH(CH$_3$)C$_2$H$_5$ |
| (Ia-1.137) | —OCH(CH$_3$)C$_2$H$_5$ | 1-methyl-2-(3,5-dimethylphenyloxy)eth-1-yl-amino | NH$_2$ | Al(O-i-Bu)$_3$ | HOCH(CH$_3$)C$_2$H$_5$ |
| (Ia-1.138) | —OCH(CH$_3$)C$_2$H$_5$ | (1R)-1-methyl-2-(3,5-dimethylphenyloxy)eth-1-yl-amino | NH$_2$ | Al(O-i-Bu)$_3$ | HOCH(CH$_3$)C$_2$H$_5$ |
| (Ia-1.139) | —OCH(CH$_3$)C$_2$H$_5$ | (1S)-1-methyl-2-(3,5-dimethylphenyloxy)eth-1-yl-amino | NH$_2$ | Al(O-i-Bu)$_3$ | HOCH(CH$_3$)C$_2$H$_5$ |
| (Ia-1.140) | —OCH(CH$_3$)C$_2$H$_5$ | 1,1-dicyclopropylmethyl-amino | NH$_2$ | Al(O-i-Bu)$_3$ | HOCH(CH$_3$)C$_2$H$_5$ |
| (Ia-1.141) | —OCH(CH$_3$)C$_2$H$_5$ | pent-3-ylamino | NH$_2$ | Al(O-i-Bu)$_3$ | HOCH(CH$_3$)C$_2$H$_5$ |
| (Ia-1.142) | —OCH(CH$_3$)C$_2$H$_5$ | 1-cyclobutyl-2-phenyleth-1-yl-amino | NH$_2$ | Al(O-i-Bu)$_3$ | HOCH(CH$_3$)C$_2$H$_5$ |
| (Ia-1.143) | —OCH(CH$_3$)C$_2$H$_5$ | (1R)-cyclobutyl-2-phenyleth-1-yl-amino | NH$_2$ | Al(O-i-Bu)$_3$ | HOCH(CH$_3$)C$_2$H$_5$ |
| (Ia-1.144) | —OCH(CH$_3$)C$_2$H$_5$ | (1S)-cyclobutyl-2-phenyleth-1-yl-amino | NH$_2$ | Al(O-i-Bu)$_3$ | HOCH(CH$_3$)C$_2$H$_5$ |
| (Ia-1.145) | O-i-Pr | morpholin-yl | NHBz | Al(O-i-Pr)$_3$ | (CH$_3$)$_2$CHOH |
| (Ia-1.146) | O-i-Pr | benzylamino | NHBz | Al(O-i-Pr)$_3$ | (CH$_3$)$_2$CHOH |
| (Ia-1.147) | O-i-Pr | cyclohexylamino | NHBz | Al(O-i-Pr)$_3$ | (CH$_3$)$_2$CHOH |
| (Ia-1.148) | O-i-Pr | 2,3-dihydro-6-methyl-1H-inden-1yl-amino | NHBz | Al(O-i-Pr)$_3$ | (CH$_3$)$_2$CHOH |
| (Ia-1.149) | O-i-Pr | (1R)-2,3-dihydro-6-methyl-1H-inden-1yl-amino | NHBz | Al(O-i-Pr)$_3$ | (CH$_3$)$_2$CHOH |
| (Ia-1.150) | O-i-Pr | (1S)-2,3-dihydro-6-methyl-1H-inden-1yl-amino | NHBz | Al(O-i-Pr)$_3$ | (CH$_3$)$_2$CHOH |
| (Ia-1.151) | O-i-Pr | 1,2,3,4-tetrahydro-quinolin-1-yl | NHBz | Al(O-i-Pr)$_3$ | (CH$_3$)$_2$CHOH |
| (Ia-1.152) | O-i-Pr | 1,2,3,4-tetrahydro-isoquinolin-2-yl | NHBz | Al(O-i-Pr)$_3$ | (CH$_3$)$_2$CHOH |
| (Ia-1.153) | O-i-Pr | 1,2,3,4-tetrahydro-napht-1-yl-amino | NHBz | Al(O-i-Pr)$_3$ | (CH$_3$)$_2$CHOH |
| (Ia-1.154) | O-i-Pr | (1R)-1,2,3,4-tetrahydro-napht-1-yl-amino | NHBz | Al(O-i-Pr)$_3$ | (CH$_3$)$_2$CHOH |
| (Ia-1.155) | O-i-Pr | (1S)-1,2,3,4-tetrahydro-napht-1-yl-amino | NHBz | Al(O-i-Pr)$_3$ | (CH$_3$)$_2$CHOH |
| (Ia-1.156) | O-i-Pr | (1R,2S)-2,3-dihydro-2,6-dimethyl-1H-inden-1yl-amino | NHBz | Al(O-i-Pr)$_3$ | (CH$_3$)$_2$CHOH |
| (Ia-1.157) | O-i-Pr | (1S,2R)-2,3-dihydro-2,4,6-trimethyl-1H-inden-1yl-amino | NHBz | Al(O-i-Pr)$_3$ | (CH$_3$)$_2$CHOH |
| (Ia-1.158) | O-i-Pr | (1R,2R)-2,3-dihydro-2,6-dimethyl-1H-inden-1yl-amino | NHBz | Al(CH$_3$)$_3$ | (CH$_3$)$_2$CHOH |
| (Ia-1.159) | O-i-Pr | (1S,2S)-2,3-dihydro-2,6-dimethyl-1H-inden-1yl-amino | NHBz | Al(CH$_3$)$_3$ | (CH$_3$)$_2$CHOH |
| (Ia-1.160) | O-i-Pr | (1R,2S)-2,3-dihydro-2-methyl-1H-inden-1yl-amino | NHBz | Al(O-i-Pr)$_3$ | (CH$_3$)$_2$CHOH |
| (Ia-1.161) | O-i-Pr | (1R,2R)-2,3-dihydro-2-methyl-1H-inden-1yl-amino | NHBz | Al(O-i-Pr)$_3$ | (CH$_3$)$_2$CHOH |
| (Ia-1.162) | O-i-Pr | (1R,2S)-2,3-dihydro-2,4,6-trimethyl-1H-inden-1yl-amino | NHBz | Al(O-i-Pr)$_3$ | (CH$_3$)$_2$CHOH |
| (Ia-1.163) | O-i-Pr | (1S,2R)-2,3-dihydro-2,6-methyl-1H-inden-1yl-amino | NHBz | Al(O-i-Pr)$_3$ | (CH$_3$)$_2$CHOH |
| (Ia-1.164) | O-i-Pr | (3RS,4RS)-3-methyl-3,4-dihydro-2H-chromen-4-yl-amino | NHBz | Al(O-i-Pr)$_3$ | (CH$_3$)$_2$CHOH |
| (Ia-1.165) | O-i-Pr | (3R,4R)-3-methyl-3,4-dihydro-2H-chromen-4-yl-amino | NHBz | Al(O-i-Pr)$_3$ | (CH$_3$)$_2$CHOH |

TABLE II-continued

Compounds of formula (Ia-1)

(Ia-1)

| Cpd. no. | Y | NR¹R² | NR³R⁴ | Al-source | Solvent |
|---|---|---|---|---|---|
| (Ia-1.166) | O-i-Pr | (3S,4S)-3-methyl-3,4-dihydro-2H-chromen-4-yl-amino | NHBz | Al(O-i-Pr)$_3$ | (CH$_3$)$_2$CHOH |
| (Ia-1.167) | O-i-Pr | 1-cyclopropylethyl-amino | NHBz | Al(O-i-Pr)$_3$ | (CH$_3$)$_2$CHOH |
| (Ia-1.168) | O-i-Pr | (1R)-cyclopropylethyl-amino | NHBz | Al(O-i-Pr)$_3$ | (CH$_3$)$_2$CHOH |
| (Ia-1.169) | O-i-Pr | (1S)-cyclopropylethyl-amino | NHBz | Al(O-i-Pr)$_3$ | (CH$_3$)$_2$CHOH |
| (Ia-1.170) | O-i-Pr | 1-(4-chlorphenyl)eth-1-yl-amino | NHBz | Al(O-i-Pr)$_3$ | (CH$_3$)$_2$CHOH |
| (Ia-1.171) | O-i-Pr | (1R)-(4-chlorphenyl)eth-1-yl-amino | NHBz | Al(O-i-Pr)$_3$ | (CH$_3$)$_2$CHOH |
| (Ia-1.172) | O-i-Pr | (1S)-(4-chlorphenyl)eth-1-yl-amino | NHBz | Al(O-i-Pr)$_3$ | (CH$_3$)$_2$CHOH |
| (Ia-1.173) | O-i-Pr | 1-methyl-2-(3,5-dimethylphenyloxy)eth-1-yl-amino | NHBz | Al(O-i-Pr)$_3$ | (CH$_3$)$_2$CHOH |
| (Ia-1.174) | O-i-Pr | (1R)-1-methyl-2-(3,5-dimethylphenyloxy)eth-1-yl-amino | NHBz | Al(O-i-Pr)$_3$ | (CH$_3$)$_2$CHOH |
| (Ia-1.175) | O-i-Pr | (1S)-1-methyl-2-(3,5-dimethylphenyloxy)eth-1-yl-amino | NHBz | Al(O-i-Pr)$_3$ | (CH$_3$)$_2$CHOH |
| (Ia-1.176) | O-i-Pr | 1,1-dicyclopropylmethyl-amino | NHBz | Al(O-i-Pr)$_3$ | (CH$_3$)$_2$CHOH |
| (Ia-1.177) | O-i-Pr | pent-3-ylamino | NHBz | Al(O-i-Pr)$_3$ | (CH$_3$)$_2$CHOH |
| (Ia-1.178) | O-i-Pr | 1-cyclobutyl-2-phenyleth-1-yl-amino | NHBz | Al(O-i-Pr)$_3$ | (CH$_3$)$_2$CHOH |
| (Ia-1.179) | O-i-Pr | (1R)-cyclobutyl-2-phenyleth-1-yl-amino | NHBz | Al(O-i-Pr)$_3$ | (CH$_3$)$_2$CHOH |
| (Ia-1.180) | O-i-Pr | (1S)-cyclobutyl-2-phenyleth-1-yl-amino | NHBz | Al(O-i-Pr)$_3$ | (CH$_3$)$_2$CHOH |
| (Ia-1.181) | —OCH(CH$_3$)CH$_2$OCH$_3$ | morpholin-yl | NH$_2$ | Al(O-i-Pr)$_3$ | HOCH(CH$_3$)CH$_2$OCH$_3$ |
| (Ia-1.182) | —OCH(CH$_3$)CH$_2$OCH$_3$ | benzylamino | NH$_2$ | Al(O-i-Pr)$_3$ | HOCH(CH$_3$)CH$_2$OCH$_3$ |
| (Ia-1.183) | —OCH(CH$_3$)CH$_2$OCH$_3$ | cyclohexylamino | NH$_2$ | Al(O-i-Pr)$_3$ | HOCH(CH$_3$)CH$_2$OCH$_3$ |
| (Ia-1.184) | —OCH(CH$_3$)CH$_2$OCH$_3$ | 2,3-dihydro-6-methyl-1H-inden-1yl-amino | NH$_2$ | Al(O-i-Pr)$_3$ | HOCH(CH$_3$)CH$_2$OCH$_3$ |
| (Ia-1.185) | —OCH(CH$_3$)CH$_2$OCH$_3$ | (1R)-2,3-dihydro-6-methyl-1H-inden-1yl-amino | NH$_2$ | Al(O-i-Pr)$_3$ | HOCH(CH$_3$)CH$_2$OCH$_3$ |
| (Ia-1.186) | —OCH(CH$_3$)CH$_2$OCH$_3$ | (1S)-2,3-dihydro-6-methyl-1H-inden-1yl-amino | NH$_2$ | Al(O-i-Pr)$_3$ | HOCH(CH$_3$)CH$_2$OCH$_3$ |
| (Ia-1.187) | —OCH(CH$_3$)CH$_2$OCH$_3$ | 1,2,3,4-tetrahydro-quinolinyl | NH$_2$ | Al(O-i-Pr)$_3$ | HOCH(CH$_3$)CH$_2$OCH$_3$ |
| (Ia-1.188) | —OCH(CH$_3$)CH$_2$OCH$_3$ | 1,2,3,4-tetrahydro-isoquinolin-2-yl | NH$_2$ | Al(O-i-Pr)$_3$ | HOCH(CH$_3$)CH$_2$OCH$_3$ |
| (Ia-1.189) | —OCH(CH$_3$)CH$_2$OCH$_3$ | (1RS)-1,2,3,4-tetrahydro-napht-1-yl-amino | NH$_2$ | Al(O-i-Pr)$_3$ | HOCH(CH$_3$)CH$_2$OCH$_3$ |
| (Ia-1.190) | —OCH(CH$_3$)CH$_2$OCH$_3$ | (1R)-1,2,3,4-tetrahydro-napht-1-yl-amino | NH$_2$ | Al(O-i-Pr)$_3$ | HOCH(CH$_3$)CH$_2$OCH$_3$ |
| (Ia-1.191) | —OCH(CH$_3$)CH$_2$OCH$_3$ | (1S)-1,2,3,4-tetrahydro-napht-1-yl-amino | NH$_2$ | Al(O-i-Pr)$_3$ | HOCH(CH$_3$)CH$_2$OCH$_3$ |
| (Ia-1.192) | —OCH(CH$_3$)CH$_2$OCH$_3$ | (1R,2S)-2,3-dihydro-2,6-dimethyl-1H-inden-1yl-amino | NH$_2$ | Al(O-i-Pr)$_3$ | HOCH(CH$_3$)CH$_2$OCH$_3$ |
| (Ia-1.193) | —OCH(CH$_3$)CH$_2$OCH$_3$ | (1S,2R)-2,3-dihydro-2,4,6-trimethyl-1H-inden-1yl-amino | NH$_2$ | Al(O-i-Pr)$_3$ | HOCH(CH$_3$)CH$_2$OCH$_3$ |
| (Ia-1.194) | —OCH(CH$_3$)CH$_2$OCH$_3$ | (1R,2R)-2,3-dihydro-2,6-dimethyl-1H-inden-1yl-amino | NH$_2$ | Al(O-i-Pr)$_3$ | HOCH(CH$_3$)CH$_2$OCH$_3$ |
| (Ia-1.195) | —OCH(CH$_3$)CH$_2$OCH$_3$ | (1S,2S)-2,3-dihydro-2,6-dimethyl-1H-inden-1yl-amino | NH$_2$ | Al(O-i-Pr)$_3$ | HOCH(CH$_3$)CH$_2$OCH$_3$ |
| (Ia-1.196) | —OCH(CH$_3$)CH$_2$OCH$_3$ | (1R,2S)-2,3-dihydro-2-methyl-1H-inden-1yl-amino | NH$_2$ | Al(O-i-Pr)$_3$ | HOCH(CH$_3$)CH$_2$OCH$_3$ |
| (Ia-1.197) | —OCH(CH$_3$)CH$_2$OCH$_3$ | (1R,2R)-2,3-dihydro-2-methyl-1H-inden-1yl-amino | NH$_2$ | Al(O-i-Pr)$_3$ | HOCH(CH$_3$)CH$_2$OCH$_3$ |
| (Ia-1.198) | —OCH(CH$_3$)CH$_2$OCH$_3$ | (1S,2S)-2,3-dihydro-2,4,6-trimethyl-1H-inden-1yl-amino | NH$_2$ | Al(O-i-Pr)$_3$ | HOCH(CH$_3$)CH$_2$OCH$_3$ |
| (Ia-1.199) | —OCH(CH$_3$)CH$_2$OCH$_3$ | (1S,2R)-2,3-dihydro-2-methyl-1H-inden-1yl-amino | NH$_2$ | Al(O-i-Pr)$_3$ | HOCH(CH$_3$)CH$_2$OCH$_3$ |
| (Ia-1.200) | —OCH(CH$_3$)CH$_2$OCH$_3$ | (3RS,4RS)-3-methyl-3,4-dihydro-2H-chromen-4-yl-amino | NH$_2$ | Al(O-i-Pr)$_3$ | HOCH(CH$_3$)CH$_2$OCH$_3$ |
| (Ia-1.201) | —OCH(CH$_3$)CH$_2$OCH$_3$ | (3R,4R)-3-methyl-3,4-dihydro-2H-chromen-4-yl-amino | NH$_2$ | Al(O-i-Pr)$_3$ | HOCH(CH$_3$)CH$_2$OCH$_3$ |
| (Ia-1.202) | —OCH(CH$_3$)CH$_2$OCH$_3$ | (3S,4S)-3-methyl-3,4-dihydro-2H-chromen-4-yl-amino | NH$_2$ | Al(O-i-Pr)$_3$ | HOCH(CH$_3$)CH$_2$OCH$_3$ |
| (Ia-1.203) | —OCH(CH$_3$)CH$_2$OCH$_3$ | 1-cyclopropylethyl-amino | NH$_2$ | Al(O-i-Pr)$_3$ | HOCH(CH$_3$)CH$_2$OCH$_3$ |
| (Ia-1.204) | —OCH(CH$_3$)CH$_2$OCH$_3$ | (1R)-cyclopropylethyl-amino | NH$_2$ | Al(O-i-Pr)$_3$ | HOCH(CH$_3$)CH$_2$OCH$_3$ |
| (Ia-1.205) | —OCH(CH$_3$)CH$_2$OCH$_3$ | (1S)-cyclopropylethyl-amino | NH$_2$ | Al(O-i-Pr)$_3$ | HOCH(CH$_3$)CH$_2$OCH$_3$ |
| (Ia-1.206) | —OCH(CH$_3$)CH$_2$OCH$_3$ | 1-(4-chlorphenyl)eth-1-yl-amino | NH$_2$ | Al(O-i-Pr)$_3$ | HOCH(CH$_3$)CH$_2$OCH$_3$ |
| (Ia-1.207) | —OCH(CH$_3$)CH$_2$OCH$_3$ | (1R)-(4-chlorphenyl)eth-1-yl-amino | NH$_2$ | Al(O-i-Pr)$_3$ | HOCH(CH$_3$)CH$_2$OCH$_3$ |
| (Ia-1.208) | —OCH(CH$_3$)CH$_2$OCH$_3$ | (1S)-(4-chlorphenyl)eth-1-yl-amino | NH$_2$ | Al(O-i-Pr)$_3$ | HOCH(CH$_3$)CH$_2$OCH$_3$ |
| (Ia-1.209) | —OCH(CH$_3$)CH$_2$OCH$_3$ | 1-methyl-2-(3,5-dimethylphenyloxy)eth-1-yl-amino | NH$_2$ | Al(O-i-Pr)$_3$ | HOCH(CH$_3$)CH$_2$OCH$_3$ |
| (Ia-1.210) | —OCH(CH$_3$)CH$_2$OCH$_3$ | (1R)-1-methyl-2-(3,5-dimethylphenyloxy)eth-1-yl-amino | NH$_2$ | Al(O-i-Pr)$_3$ | HOCH(CH$_3$)CH$_2$OCH$_3$ |
| (Ia-1.211) | —OCH(CH$_3$)CH$_2$OCH$_3$ | (1S)-1-methyl-2-(3,5-dimethylphenyloxy)eth-1-yl-amino | NH$_2$ | Al(O-i-Pr)$_3$ | HOCH(CH$_3$)CH$_2$OCH$_3$ |
| (Ia-1.212) | —OCH(CH$_3$)CH$_2$OCH$_3$ | 1,1-dicyclopropylmethyl-amino | NH$_2$ | Al(O-i-Pr)$_3$ | HOCH(CH$_3$)CH$_2$OCH$_3$ |
| (Ia-1.213) | —OCH(CH$_3$)CH$_2$OCH$_3$ | pent-3-ylamino | NH$_2$ | Al(O-i-Pr)$_3$ | HOCH(CH$_3$)CH$_2$OCH$_3$ |
| (Ia-1.214) | —OCH(CH$_3$)CH$_2$OCH$_3$ | 1-cyclobutyl-2-phenyleth-1-yl-amino | NH$_2$ | Al(O-i-Pr)$_3$ | HOCH(CH$_3$)CH$_2$OCH$_3$ |
| (Ia-1.215) | —OCH(CH$_3$)CH$_2$OCH$_3$ | (1R)-cyclobutyl-2-phenyleth-1-yl-amino | NH$_2$ | Al(O-i-Pr)$_3$ | HOCH(CH$_3$)CH$_2$OCH$_3$ |
| (Ia-1.216) | —OCH(CH$_3$)CH$_2$OCH$_3$ | (1S)-cyclobutyl-2-phenyleth-1-yl-amino | NH$_2$ | Al(O-i-Pr)$_3$ | HOCH(CH$_3$)CH$_2$OCH$_3$ |
| (Ia-1.217) | —OCH$_2$CH$_2$OC$_2$H$_5$ | morpholin-yl | NH$_2$ | Al(O-i-Pr)$_3$ | HOCH$_2$CH$_2$OC$_2$H$_5$ |
| (Ia-1.218) | —OCH$_2$CH$_2$OC$_2$H$_5$ | benzylamino | NH$_2$ | Al(O-i-Pr)$_3$ | HOCH$_2$CH$_2$OC$_2$H$_5$ |
| (Ia-1.219) | —OCH$_2$CH$_2$OC$_2$H$_5$ | cyclohexylamino | NH$_2$ | Al(O-i-Pr)$_3$ | HOCH$_2$CH$_2$OC$_2$H$_5$ |
| (Ia-1.220) | —OCH$_2$CH$_2$OC$_2$H$_5$ | (1RS)-2,3-dihydro-6-methyl-1H-inden-1yl-amino | NH$_2$ | Al(O-i-Pr)$_3$ | HOCH$_2$CH$_2$OC$_2$H$_5$ |
| (Ia-1.221) | —OCH$_2$CH$_2$OC$_2$H$_5$ | (1R)-2,3-dihydro-6-methyl-1H-inden-1yl-amino | NH$_2$ | Al(O-i-Pr)$_3$ | HOCH$_2$CH$_2$OC$_2$H$_5$ |
| (Ia-1.222) | —OCH$_2$CH$_2$OC$_2$H$_5$ | (1S)-2,3-dihydro-6-methyl-1H-inden-1yl-amino | NH$_2$ | Al(O-i-Pr)$_3$ | HOCH$_2$CH$_2$OC$_2$H$_5$ |
| (Ia-1.223) | —OCH$_2$CH$_2$OC$_2$H$_5$ | 1,2,3,4-tetrahydro-quinlin-1-yl | NH$_2$ | Al(O-i-Pr)$_3$ | HOCH$_2$CH$_2$OC$_2$H$_5$ |
| (Ia-1.224) | —OCH$_2$CH$_2$OC$_2$H$_5$ | 1,2,3,4-tetrahydro-isoquinolin-2-yl | NH$_2$ | Al(O-i-Pr)$_3$ | HOCH$_2$CH$_2$OC$_2$H$_5$ |
| (Ia-1.225) | —OCH$_2$CH$_2$OC$_2$H$_5$ | 1,2,3,4-tetrahydro-napht-1-yl-amino | NH$_2$ | Al(O-i-Pr)$_3$ | HOCH$_2$CH$_2$OC$_2$H$_5$ |
| (Ia-1.226) | —OCH$_2$CH$_2$OC$_2$H$_5$ | (1R)-1,2,3,4-tetrahydro-napht-1-yl-amino | NH$_2$ | Al(O-i-Pr)$_3$ | HOCH$_2$CH$_2$OC$_2$H$_5$ |
| (Ia-1.227) | —OCH$_2$CH$_2$OC$_2$H$_5$ | (1S)-1,2,3,4-tetrahydro-napht-1-yl-amino | NH$_2$ | Al(O-i-Pr)$_3$ | HOCH$_2$CH$_2$OC$_2$H$_5$ |
| (Ia-1.228) | —OCH$_2$CH$_2$OC$_2$H$_5$ | (1R,2S)-2,3-dihydro-2,6-dimethyl-1H-inden-1yl-amino | NH$_2$ | Al(O-i-Pr)$_3$ | HOCH$_2$CH$_2$OC$_2$H$_5$ |
| (Ia-1.229) | —OCH$_2$CH$_2$OC$_2$H$_5$ | (1S,2R)-2,3-dihydro-2,4,6-trimethyl-1H-inden-1yl-amino | NH$_2$ | Al(O-i-Pr)$_3$ | HOCH$_2$CH$_2$OC$_2$H$_5$ |
| (Ia-1.230) | —OCH$_2$CH$_2$OC$_2$H$_5$ | (1R,2R)-2,3-dihydro-2,6-dimethyl-1H-inden-1yl-amino | NH$_2$ | Al(O-i-Pr)$_3$ | HOCH$_2$CH$_2$OC$_2$H$_5$ |

TABLE II-continued

Compounds of formula (Ia-1)

(Ia-1)

| Cpd. no. | Y | NR$^1$R$^2$ | NR$^3$R$^4$ | Al-source | Solvent |
|---|---|---|---|---|---|
| (Ia-1.231) | —OCH$_2$CH$_2$OC$_2$H$_5$ | (1S,2S)-2,3-dihydro-2,6-dimethyl-1H-inden-1yl-amino | NH$_2$ | Al(O-i-Pr)$_3$ | HOCH$_2$CH$_2$OC$_2$H$_5$ |
| (Ia-1.232) | —OCH$_2$CH$_2$OC$_2$H$_5$ | (1R,2S)-2,3-dihydro-2-methyl-1H-inden-1yl-amino | NH$_2$ | Al(O-i-Pr)$_3$ | HOCH$_2$CH$_2$OC$_2$H$_5$ |
| (Ia-1.233) | —OCH$_2$CH$_2$OC$_2$H$_5$ | (1R,2R)-2,3-dihydro-2-methyl-1H-inden-1yl-amino | NH$_2$ | Al(O-i-Pr)$_3$ | HOCH$_2$CH$_2$OC$_2$H$_5$ |
| (Ia-1.234) | —OCH$_2$CH$_2$OC$_2$H$_5$ | (1R,2S)-2,3-dihydro-2,4,6-trimethyl-1H-inden-1yl-amino | NH$_2$ | Al(O-i-Pr)$_3$ | HOCH$_2$CH$_2$OC$_2$H$_5$ |
| (Ia-1.235) | —OCH$_2$CH$_2$OC$_2$H$_5$ | (1S,2R)-2,3-dihydro-2,6-methyl-1H-inden-1yl-amino | NH$_2$ | Al(O-i-Pr)$_3$ | HOCH$_2$CH$_2$OC$_2$H$_5$ |
| (Ia-1.236) | —OCH$_2$CH$_2$OC$_2$H$_5$ | (3RS,4RS)-3-methyl-3,4-dihydro-2H-chromen-4-yl-amino | NH$_2$ | Al(O-i-Pr)$_3$ | HOCH$_2$CH$_2$OC$_2$H$_5$ |
| (Ia-1.237) | —OCH$_2$CH$_2$OC$_2$H$_5$ | (3R,4R)-3-methyl-3,4-dihydro-2H-chromen-4-yl-amino | NH$_2$ | Al(O-i-Pr)$_3$ | HOCH$_2$CH$_2$OC$_2$H$_5$ |
| (Ia-1.238) | —OCH$_2$CH$_2$OC$_2$H$_5$ | (3S,4S)-3-methyl-3,4-dihydro-2H-chromen-4-yl-amino | NH$_2$ | Al(O-i-Pr)$_3$ | HOCH$_2$CH$_2$OC$_2$H$_5$ |
| (Ia-1.239) | —OCH$_2$CH$_2$OC$_2$H$_5$ | 1-cyclopropylethyl-amino | NH$_2$ | Al(O-i-Pr)$_3$ | HOCH$_2$CH$_2$OC$_2$H$_5$ |
| (Ia-1.240) | —OCH$_2$CH$_2$OC$_2$H$_5$ | (1R)-cyclopropylethyl-amino | NH$_2$ | Al(O-i-Pr)$_3$ | HOCH$_2$CH$_2$OC$_2$H$_5$ |
| (Ia-1.241) | —OCH$_2$CH$_2$OC$_2$H$_5$ | (1S)-cyclopropylethyl-amino | NH$_2$ | Al(O-i-Pr)$_3$ | HOCH$_2$CH$_2$OC$_2$H$_5$ |
| (Ia-1.242) | —OCH$_2$CH$_2$OC$_2$H$_5$ | 1-(4-chlorphenyl)eth-1-yl-amino | NH$_2$ | Al(O-i-Pr)$_3$ | HOCH$_2$CH$_2$OC$_2$H$_5$ |
| (Ia-1.243) | —OCH$_2$CH$_2$OC$_2$H$_5$ | (1R)-(4-chlorphenyl)eth-1-yl-amino | NH$_2$ | Al(O-i-Pr)$_3$ | HOCH$_2$CH$_2$OC$_2$H$_5$ |
| (Ia-1.244) | —OCH$_2$CH$_2$OC$_2$H$_5$ | (1S)-(4-chlorphenyl)eth-1-yl-amino | NH$_2$ | Al(O-i-Pr)$_3$ | HOCH$_2$CH$_2$OC$_2$H$_5$ |
| (Ia-1.245) | —OCH$_2$CH$_2$OC$_2$H$_5$ | 1-methyl-2-(3,5-dimethylphenyloxy)eth-2-yl-amino | NH$_2$ | Al(O-i-Pr)$_3$ | HOCH$_2$CH$_2$OC$_2$H$_5$ |
| (Ia-1.246) | —OCH$_2$CH$_2$OC$_2$H$_5$ | (1R)-1-methyl-2-(3,5-dimethylphenyloxy)eth-2-yl-amino | NH$_2$ | Al(O-i-Pr)$_3$ | HOCH$_2$CH$_2$OC$_2$H$_5$ |
| (Ia-1.247) | —OCH$_2$CH$_2$OC$_2$H$_5$ | (1S)-1-methyl-2-(3,5-dimethylphenyloxy)eth-2-yl-amino | NH$_2$ | Al(O-i-Pr)$_3$ | HOCH$_2$CH$_2$OC$_2$H$_5$ |
| (Ia-1.248) | —OCH$_2$CH$_2$OC$_2$H$_5$ | 1,1-dicyclopropylmethyl-amino | NH$_2$ | Al(O-i-Pr)$_3$ | HOCH$_2$CH$_2$OC$_2$H$_5$ |
| (Ia-1.249) | —OCH$_2$CH$_2$OC$_2$H$_5$ | pent-3-ylamino | NH$_2$ | Al(O-i-Pr)$_3$ | HOCH$_2$CH$_2$OC$_2$H$_5$ |
| (Ia-1.250) | —OCH$_2$CH$_2$OC$_2$H$_5$ | 1-cyclobutyl-2-phenyleth-1-yl-amino | NH$_2$ | Al(O-i-Pr)$_3$ | HOCH$_2$CH$_2$OC$_2$H$_5$ |
| (Ia-1.251) | —OCH$_2$CH$_2$OC$_2$H$_5$ | (1R)-cyclobutyl-2-phenyleth-1-yl-amino | NH$_2$ | Al(O-i-Pr)$_3$ | HOCH$_2$CH$_2$OC$_2$H$_5$ |
| (Ia-1.252) | —OCH$_2$CH$_2$OC$_2$H$_5$ | (1S)-cyclobutyl-2-phenyleth-1-yl-amino | NH$_2$ | Al(O-i-Pr)$_3$ | HOCH$_2$CH$_2$OC$_2$H$_5$ |
| (Ia-1.253) | —OCH$_2$CH$_2$OC$_2$H$_5$ | (1R,2R)-2,3-dihydro-2,4,6-trimethyl-1H-inden-1yl-amino | NH$_2$ | Al(O-i-Pr)$_3$ | HOCH$_2$CH$_2$OC$_2$H$_5$ |
| (Ia-1.254) | —OCH$_2$CH$_2$OC$_2$H$_5$ | (1S,2S)-2,3-dihydro-2,4,6-trimethyl-1H-inden-1yl-amino | NH$_2$ | Al(O-i-Pr)$_3$ | HOCH$_2$CH$_2$OC$_2$H$_5$ |
| (Ia-1.255) | —OCH$_2$CH$_2$OC$_2$H$_5$ | (1S,2R)-2,3-dihydro-2-methyl-1H-inden-1yl-amino | NH$_2$ | Al(O-i-Pr)$_3$ | HOCH$_2$CH$_2$OC$_2$H$_5$ |
| (Ia-1.256) | —OCH$_2$CH$_2$OC$_2$H$_5$ | (1S,2S)-2,3-dihydro-2-methyl-1H-inden-1yl-amino | NH$_2$ | Al(O-i-Pr)$_3$ | HOCH$_2$CH$_2$OC$_2$H$_5$ |
| (Ia-1.257) | —OCH(CH$_3$)C$_2$H$_5$ | morpholin-yl | NHBz | Al(O-i-Bu)$_3$ | HOCH(CH$_3$)C$_2$H$_5$ |
| (Ia-1.258) | —OCH(CH$_3$)C$_2$H$_5$ | benzylamino | NHBz | Al(O-i-Bu)$_3$ | HOCH(CH$_3$)C$_2$H$_5$ |
| (Ia-1.259) | —OCH(CH$_3$)C$_2$H$_5$ | cyclohexylamino | NHBz | Al(O-i-Bu)$_3$ | HOCH(CH$_3$)C$_2$H$_5$ |
| (Ia-1.260) | —OCH(CH$_3$)C$_2$H$_5$ | 2,3-dihydro-6-methyl-1H-inden-1yl-amino | NHBz | Al(O-i-Bu)$_3$ | HOCH(CH$_3$)C$_2$H$_5$ |
| (Ia-1.261) | —OCH(CH$_3$)C$_2$H$_5$ | (1R)-2,3-dihydro-6-methyl-1H-inden-1yl-amino | NHBz | Al(O-i-Bu)$_3$ | HOCH(CH$_3$)C$_2$H$_5$ |
| (Ia-1.262) | —OCH(CH$_3$)C$_2$H$_5$ | (1S)-2,3-dihydro-6-methyl-1H-inden-1yl-amino | NHBz | Al(O-i-Bu)$_3$ | HOCH(CH$_3$)C$_2$H$_5$ |
| (Ia-1.263) | —OCH(CH$_3$)C$_2$H$_5$ | 1,2,3,4-tetrahydro-quinolin-1-yl | NHBz | Al(O-i-Bu)$_3$ | HOCH(CH$_3$)C$_2$H$_5$ |
| (Ia-1.264) | —OCH(CH$_3$)C$_2$H$_5$ | 1,2,3,4-tetrahydro-isoquinolin-2-yl | NHBz | Al(O-i-Bu)$_3$ | HOCH(CH$_3$)C$_2$H$_5$ |
| (Ia-1.265) | —OCH(CH$_3$)C$_2$H$_5$ | 1,2,3,4-tetrahydro-napht-1-yl-amino | NHBz | Al(O-i-Bu)$_3$ | HOCH(CH$_3$)C$_2$H$_5$ |
| (Ia-1.266) | —OCH(CH$_3$)C$_2$H$_5$ | (1R)-1,2,3,4-tetrahydro-napht-1-yl-amino | NHBz | Al(O-i-Bu)$_3$ | HOCH(CH$_3$)C$_2$H$_5$ |
| (Ia-1.267) | —OCH(CH$_3$)C$_2$H$_5$ | (1S)-1,2,3,4-tetrahydro-napht-1-yl-amino | NHBz | Al(O-i-Bu)$_3$ | HOCH(CH$_3$)C$_2$H$_5$ |
| (Ia-1.268) | —OCH(CH$_3$)C$_2$H$_5$ | (1R,2S)-2,3-dihydro-2,6-dimethyl-1H-inden-1yl-amino | NHBz | Al(O-i-Bu)$_3$ | HOCH(CH$_3$)C$_2$H$_5$ |
| (Ia-1.269) | —OCH(CH$_3$)C$_2$H$_5$ | (1S,2R)-2,3-dihydro-2,4,6-trimethyl-1H-inden-1yl-amino | NHBz | Al(O-i-Bu)$_3$ | HOCH(CH$_3$)C$_2$H$_5$ |
| (Ia-1.270) | —OCH(CH$_3$)C$_2$H$_5$ | (1R,2R)-2,3-dihydro-2,6-dimethyl-1H-inden-1yl-amino | NHBz | Al(O-i-Bu)$_3$ | HOCH(CH$_3$)C$_2$H$_5$ |
| (Ia-1.271) | —OCH(CH$_3$)C$_2$H$_5$ | (1S,2S)-2,3-dihydro-2,6-dimethyl-1H-inden-1yl-amino | NHBz | Al(O-i-Bu)$_3$ | HOCH(CH$_3$)C$_2$H$_5$ |
| (Ia-1.272) | —OCH(CH$_3$)C$_2$H$_5$ | (1R,2S)-2,3-dihydro-2-methyl-1H-inden-1yl-amino | NHBz | Al(O-i-Bu)$_3$ | HOCH(CH$_3$)C$_2$H$_5$ |
| (Ia-1.273) | —OCH(CH$_3$)C$_2$H$_5$ | (1R,2R)-2,3-dihydro-2-methyl-1H-inden-1yl-amino | NHBz | Al(O-i-Bu)$_3$ | HOCH(CH$_3$)C$_2$H$_5$ |
| (Ia-1.274) | —OCH(CH$_3$)C$_2$H$_5$ | (1R,2S)-2,3-dihydro-2,4,6-trimethyl-1H-inden-1yl-amino | NHBz | Al(O-i-Bu)$_3$ | HOCH(CH$_3$)C$_2$H$_5$ |
| (Ia-1.275) | —OCH(CH$_3$)C$_2$H$_5$ | (1S,2R)-2,3-dihydro-2,6-methyl-1H-inden-1yl-amino | NHBz | Al(O-i-Bu)$_3$ | HOCH(CH$_3$)C$_2$H$_5$ |
| (Ia-1.276) | —OCH(CH$_3$)C$_2$H$_5$ | (3RS,4RS)-3-methyl-3,4-dihydro-2H-chromen-4-yl-amino | NHBz | Al(O-i-Bu)$_3$ | HOCH(CH$_3$)C$_2$H$_5$ |
| (Ia-1.277) | —OCH(CH$_3$)C$_2$H$_5$ | (3R,4R)-3-methyl-3,4-dihydro-2H-chromen-4-yl-amino | NHBz | Al(O-i-Bu)$_3$ | HOCH(CH$_3$)C$_2$H$_5$ |
| (Ia-1.278) | —OCH(CH$_3$)C$_2$H$_5$ | (3S,4S)-3-methyl-3,4-dihydro-2H-chromen-4-yl-amino | NHBz | Al(O-i-Bu)$_3$ | HOCH(CH$_3$)C$_2$H$_5$ |
| (Ia-1.279) | —OCH(CH$_3$)C$_2$H$_5$ | 1-cyclopropylethyl-amino | NHBz | Al(O-i-Bu)$_3$ | HOCH(CH$_3$)C$_2$H$_5$ |
| (Ia-1.280) | —OCH(CH$_3$)C$_2$H$_5$ | (1R)-cyclopropylethyl-amino | NHBz | Al(O-i-Bu)$_3$ | HOCH(CH$_3$)C$_2$H$_5$ |
| (Ia-1.281) | —OCH(CH$_3$)C$_2$H$_5$ | (1S)-cyclopropylethyl-amino | NHBz | Al(O-i-Bu)$_3$ | HOCH(CH$_3$)C$_2$H$_5$ |
| (Ia-1.282) | —OCH(CH$_3$)C$_2$H$_5$ | 1-(4-chlorphenyl)eth-1-yl-amino | NHBz | Al(O-i-Bu)$_3$ | HOCH(CH$_3$)C$_2$H$_5$ |
| (Ia-1.283) | —OCH(CH$_3$)C$_2$H$_5$ | (1R)-(4-chlorphenyl)eth-1-yl-amino | NHBz | Al(O-i-Bu)$_3$ | HOCH(CH$_3$)C$_2$H$_5$ |
| (Ia-1.284) | —OCH(CH$_3$)C$_2$H$_5$ | (1S)-(4-chlorphenyl)eth-1-yl-amino | NHBz | Al(O-i-Bu)$_3$ | HOCH(CH$_3$)C$_2$H$_5$ |
| (Ia-1.285) | —OCH(CH$_3$)C$_2$H$_5$ | 1-methyl-2-(3,5-dimethylphenyloxy)eth-1-yl-amino | NHBz | Al(O-i-Bu)$_3$ | HOCH(CH$_3$)C$_2$H$_5$ |
| (Ia-1.286) | —OCH(CH$_3$)C$_2$H$_5$ | (1R)-1-methyl-2-(3,5-dimethylphenyloxy)eth-1-yl-amino | NHBz | Al(O-i-Bu)$_3$ | HOCH(CH$_3$)C$_2$H$_5$ |
| (Ia-1.287) | —OCH(CH$_3$)C$_2$H$_5$ | (1S)-1-methyl-2-(3,5-dimethylphenyloxy)eth-1-yl-amino | NHBz | Al(O-i-Bu)$_3$ | HOCH(CH$_3$)C$_2$H$_5$ |
| (Ia-1.288) | —OCH(CH$_3$)C$_2$H$_5$ | 1,1-dicyclopropylmethyl-amino | NHBz | Al(O-i-Bu)$_3$ | HOCH(CH$_3$)C$_2$H$_5$ |
| (Ia-1.289) | —OCH(CH$_3$)C$_2$H$_5$ | pent-3-ylamino | NHBz | Al(O-i-Bu)$_3$ | HOCH(CH$_3$)C$_2$H$_5$ |
| (Ia-1.290) | —OCH(CH$_3$)C$_2$H$_5$ | 1-cyclobutyl-2-phenyleth-1-yl-amino | NHBz | Al(O-i-Bu)$_3$ | HOCH(CH$_3$)C$_2$H$_5$ |
| (Ia-1.291) | —OCH(CH$_3$)C$_2$H$_5$ | (1R)-cyclobutyl-2-phenyleth-1-yl-amino | NHBz | Al(O-i-Bu)$_3$ | HOCH(CH$_3$)C$_2$H$_5$ |
| (Ia-1.292) | —OCH(CH$_3$)C$_2$H$_5$ | (1S)-cyclobutyl-2-phenyleth-1-yl-amino | NHBz | Al(O-i-Bu)$_3$ | HOCH(CH$_3$)C$_2$H$_5$ |
| (Ia-1.293) | —OCH(CH$_3$)C$_2$H$_5$ | (3S,4R)-3-methyl-3,4-dihydro-2H-chromen-4-yl-amino | NHBz | Al(O-i-Bu)$_3$ | HOCH(CH$_3$)C$_2$H$_5$ |
| (Ia-1.294) | —OCH(CH$_3$)C$_2$H$_5$ | (3R,4S)-3-methyl-3,4-dihydro-2H-chromen-4-yl-amino | NHBz | Al(O-i-Bu)$_3$ | HOCH(CH$_3$)C$_2$H$_5$ |
| (Ia-1.295) | —OCH$_2$CH$_2$OC$_2$H$_5$ | (3S,4R)-3-methyl-3,4-dihydro-2H-chromen-4-yl-amino | NH$_2$ | Al(O-i-Pr)$_3$ | HOCH$_2$CH$_2$OC$_2$H$_5$ |

TABLE II-continued

Compounds of formula (Ia-1)

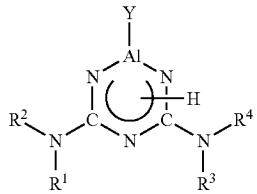

(Ia-1)

| Cpd. no. | Y | $NR^1R^2$ | $NR^3R^4$ | Al-source | Solvent |
|---|---|---|---|---|---|
| (Ia-1.296) | —OCH$_2$CH$_2$OC$_2$H$_5$ | (3R,4S)-3-methyl-3,4-dihydro-2H-chromen-4-yl-amino | NH$_2$ | Al(O-i-Pr)$_3$ | HOCH$_2$CH$_2$OC$_2$H$_5$ |
| (Ia-1.297) | —O-i-Pr | (3S,4R)-3-methyl-3,4-dihydro-2H-chromen-4-yl-amino | NH$_2$ | Al(O-i-Pr)$_3$ | (CH$_3$)$_2$CHOH |
| (Ia-1.298) | —O-i-Pr | (3R,4S)-3-methyl-3,4-dihydro-2H-chromen-4-yl-amino | NH$_2$ | Al(O-i-Pr)$_3$ | (CH$_3$)$_2$CHOH |

Reaction Conditions as to Table II:
1) Reaction temperature of 90 to 100° C.
2) Al-source used in an amount of 1 to 2 eq based on amine
3) cyanoguanidine used in an amount of 1 to 2 eq based on amine Abbreviations as to Table II:
—O-i-Pr = Isopropoxy
    Bz = benzyl
  NHBz = benzylamino
  NBz$_2$ = dibenzylamino

The invention claimed is:

1. A compound of formula (Ia), the formula (Ia) being represented by:

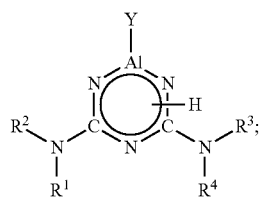

(Ia)

wherein:
R$^1$ and R$^2$ are defined as follows:
R$^1$ is:
(C$_1$-C$_{18}$)alkyl, (C$_2$-C$_{18}$)alkenyl, or (C$_2$-C$_{18}$)alkenyl; or
a group of the formula A$^1$; and
R$^2$ is:
H, (C$_1$-C$_{18}$)alkenyl, (C$_2$-C$_{18}$)alkenyl or (C$_2$-C$_{18}$)alkynyl; or
a group of the formula A$^2$; or
R$^1$ and R$^2$ together with the N-atom, linked to each other form a N-heterocyclic ring having 3 to 7 ring atoms and optionally having one or more additional hetero atoms selected from the group consisting of N, O, and S;
wherein:
R$^3$ and R$^4$ are defined as follows:
R$^3$ is:
H, (C$_1$ C$_{18}$)alkyl, (C$_2$-C$_{18}$)alkenyl, or (C$_2$-C$_{18}$) alkynyl; or
a group of the formula A$^3$; and
R$^4$ is:
H(C$_1$-C$_{18}$)alkyl, (C$_2$-C$_{18}$)alkenyl, or (C$_2$-C$_{18}$) alkynyl; or
a group of the formula A$^4$; or R$^3$ and R$^4$ together with the N-atom linked to each other form a N-heterocyclic ring having 3 to 7 ring atoms and optionally having one or more additional hetero atoms selected from the group consisting of N, O, and S; and wheren:
A$^1$, A$^2$, A$^3$, and A$^4$, independently of one another, are (C$_{3-C9}$)cycloalkyl, (C$_4$-C$_9$)cycloalkenyl, (C$_7$-C$_9$)cycloalkynyl, aryl, or heterocyclyl as a basic cyclic moiety;

wherein:
Y is selected from the group consisting of:
(iv) (C$_1$-C$_4$)alkoxy, (C$_1$-C$_4$)haloalkoxy, (C$_1$-C$_4$)alkoxy, (C1-C$_4$)alkoxy, and (C$_1$-C$_4$)alkylthio.

2. A process for preparing a compound of formula (Ia) or a salt thereof according to claim 1, where the formula (Ia) is represented by:

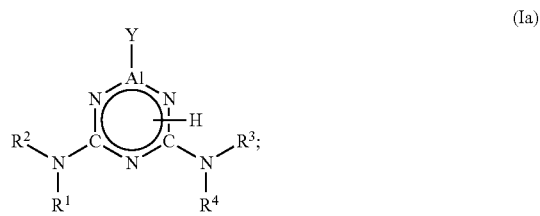

(Ia)

in which R$^1$ to R$^4$ and Y are as defined in claim 1 for formula (Ia);

wherein the method comprises:
reacting a compound (an amine) of the formula (II) or a salt thereof, with a compound of the formula (IIIa) or a salt thereof, and an aluminium(III) source, in the presence of a protic additive or solvent;

wherein the formula (II) is represented by:

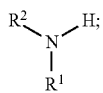  (II)

in which $R^1$ and $R^2$ are defined as in the compound of formula (Ia) to be prepared;

wherein the formula (IIIa) is represented by:

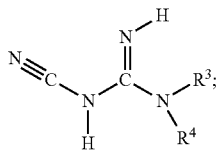  (IIIa)

in which $R^3$ and $R^4$ are defined as in the compound of formula (Ia) to be prepared;

wherein the aluminium(III) source is selected from:
(i) aluminium salts of the formula (IV):

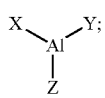  (IV)

which:
Y is as defined in the compound of formula (Ia) to be prepared; and
X and Z are the same as Y; and
wherein the protic additive or solvent is X—H, Y—H, or Z—H;
wherein each of X, Y, and Z are defined as set forth in formula (IV).

* * * * *